US011319555B2

(12) United States Patent
Guilak et al.

(10) Patent No.: US 11,319,555 B2
(45) Date of Patent: May 3, 2022

(54) COMPOSITIONS, SYSTEMS AND METHODS FOR CELL THERAPY

(71) Applicant: Duke University, Durham, NC (US)

(72) Inventors: Farshid Guilak, Durham, NC (US); Jonathan M. Brunger, Durham, NC (US); Charles A. Gersbach, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/528,296

(22) PCT Filed: Nov. 20, 2015

(86) PCT No.: PCT/US2015/062024
§ 371 (c)(1),
(2) Date: May 19, 2017

(87) PCT Pub. No.: WO2016/081924
PCT Pub. Date: May 26, 2016

(65) Prior Publication Data
US 2018/0201951 A1 Jul. 19, 2018

Related U.S. Application Data

(60) Provisional application No. 62/082,315, filed on Nov. 20, 2014.

(51) Int. Cl.
| C12N 15/85 | (2006.01) |
| C12N 15/11 | (2006.01) |
| A61P 25/28 | (2006.01) |
| A61K 35/28 | (2015.01) |
| A61K 38/17 | (2006.01) |
| A61K 48/00 | (2006.01) |

(52) U.S. Cl.
CPC .............. *C12N 15/85* (2013.01); *A61K 35/28* (2013.01); *A61K 38/1793* (2013.01); *A61K 48/005* (2013.01); *A61P 25/28* (2018.01); *C12N 15/111* (2013.01); *C12N 2310/20* (2017.05); *C12N 2320/30* (2013.01)

(58) Field of Classification Search
None
See application file for complete search history.

(56) References Cited

U.S. PATENT DOCUMENTS

| 5,593,972 | A | 1/1997 | Weiner et al. |
| 5,773,700 | A | 6/1998 | Van Grinsven et al. |
| 5,962,428 | A | 10/1999 | Carrano et al. |
| 6,127,176 | A | 10/2000 | Stark et al. |
| 9,738,879 | B2 | 8/2017 | Gersbach et al. |
| 2004/0175727 | A1 | 9/2004 | Draghia-Akli et al. |
| 2008/0292593 | A1 | 11/2008 | Passini et al. |
| 2010/0255572 | A1 | 10/2010 | Schmidt et al. |
| 2011/0197290 | A1 | 8/2011 | Fahrenkrug et al. |
| 2011/0301073 | A1 | 12/2011 | Gregory et al. |
| 2013/0274129 | A1 | 10/2013 | Katzen et al. |
| 2014/0234975 | A1 | 8/2014 | Silva et al. |
| 2014/0273226 | A1* | 9/2014 | Wu ........................ C12N 15/907 435/455 |
| 2015/0079064 | A1 | 3/2015 | Gersbach et al. |
| 2015/0159178 | A1 | 6/2015 | Green et al. |
| 2017/0067078 | A1* | 3/2017 | Frendewey .......... C12N 15/907 |

FOREIGN PATENT DOCUMENTS

| CA | 2749305 | 7/2010 |
| WO | WO 1993/024640 | 12/1993 |
| WO | WO 1994/016737 | 8/1994 |
| WO | WO 2001/083783 | 11/2001 |
| WO | WO 2008/006028 | 1/2008 |
| WO | WO 2011/036640 | 3/2011 |
| WO | WO 2011/154427 | 12/2011 |
| WO | WO 2013/163628 | 10/2013 |

OTHER PUBLICATIONS

Luo et al., Stable Enhanced Green Fluorescent Protein Expression After Differentiation and Transplantation of Reporter Human Induced Pluripotent Stem Cells Generated by AAVS1 Transcription Activator-Like; Stem Cells Translational Medicine 2014;3:821-835.*
Zou et al., Cell Stem Cell 5, 97-110, Jul. 2, 2009.*
HEK 293 cells—Wikipedia; pp. 1-4; downloaded Mar. 11, 2020.*
Li et al., Optimization of Genome Engineering Approaches with the CRISPR/Cas9 System PLOS ONE |Aug. 2014 | vol. 9 | Issue 8 | e105779 pp. 1-10.*
Chen et al Comparison of Exogenous Promoter Activity at the ROSA26 Locus Using a PhiC31 Integrase Mediated Cassette Exchange Approach in Mouse ES Cells PLoS ONE Aug. 2011 | vol. 6 | Issue 8 | e23376 pp. 1-8.*
Rojas-Fernandez et al., Rapid generation of endogenously driven transcriptional reporters in cells through CRISPR/Cas9 Scientific Reports, Apr. 29, 2015; pp. 1-6.*
GONDA-DISSERTATION-2014.pdf (4.717Mb) Genetically Reprogramming Immune Modulatory Activity in Cancer Cells using TALE and CRISPR/Cas9 Technologies View/Open; pp. 1-233.*
U.S. Appl. No. 61/831,481, filed Jun. 5, 2013.
U.S. Appl. No. 61/839,127, filed Jun. 25, 2013.
U.S. Appl. No. 61/967,466, filed Mar. 19, 2014.
PCT/US2014/041190, Jun. 5, 2014, WO2014/197748, Dec. 11, 2014.
U.S. Appl. No. 14/895,316, filed Dec. 2, 2015, 2016/0201089, Jul. 14, 2016.
U.S. Appl. No. 15/991,333, filed May 29, 2018.

(Continued)

*Primary Examiner* — Maria G Leavitt

(57) ABSTRACT

Disclosed herein are compositions and methods for cell therapy comprising an engineered cell. The present invention is directed to a composition for treating a subject having or suspected of having a disease, the composition comprising a modified cell comprising a modified endogenous gene, wherein an endogenous gene or fragment thereof is replaced with a transgene using a CRISPR/Cas9 system to generate the modified endogenous gene, the modified cell having an altered response to a cell signal or stimulus.

4 Claims, 38 Drawing Sheets

Specification includes a Sequence Listing.

(56) References Cited

OTHER PUBLICATIONS

Aartsma-Rus et al., "Antisense-mediated exon skipping: a versatile tool with therapeutic and research applications," RNA 13, 2007, 1609-1624.

Aartsma-Rus et al., "Exploring the frontiers of therapeutic exon skipping for Duchenne muscular dystrophy by double targeting within one or multiple exons," Mol Ther, 2006, 14:401-407.

Aartsma-Rus et al., "Theoretic applicability of antisense-mediated exon skipping for Duchenne muscular dystrophy mutations," Hum Mutat, 2009, 30:293-299.

Adler et al., "Nonviral direct conversion of primary mouse embryonic fibroblasts to neuronal cells," Molecular therapy, 2012 Nucleic acids 1, e32.

Aigner et al., "Cartilage tissue engineering with novel nonwoven structured biomaterial based on hyaluronic acid benzyl ester," Journal ofbiomedical materials research 42, 1998, pp. 172-181.

Aiuti et al., "Lentiviral hematopoietic stem cell gene therapy in patients with Wiskott-Aldrich syndrome," Science, 2013, 341(6148): 1233151.

Akizuki et al., "Tensile properties of human knee joint cartilage: I. Influence of ionic conditions, weightbearing, and fibrillation on the tensile modulus," Journal of orthopaedic research: official publication of the Orthopaedic Research Society 4, 1986, 379-392.

Amin Yavari et al., "Fatigue behavior of porous biomaterials manufactured using selective laser melting," Materials Science and Engineering: C 33, 2013, 4849-4858.

Anders et al., "Differential expression analysis for sequence count data," Genome biology 11, 2010, R106.

Anguela et al., "Robust ZFN-mediated genome editing in adult hemophilic mice," Blood, 2013, 122:3283-3287.

Aoki et al., "Bodywide skipping of exons 45-55 in dystrophic mdx52 mice by systemic antisense delivery," Proc Natl Acad Sci USA, 2012, 109:13763-13768.

Atala et al., "Engineering complex tissues," Science translational medicine 4, 2012, 160rv112.

Ateshian, "The role of interstitial fluid pressurization in articular cartilage lubrication," Journal of biomechanics 42, 2009, 1163-1176.

Athanasiou et al., "Comparative study of the intrinsic mechanical properties of the human acetabular and femoral head cartilage," Journal of orthopaedic research: official publication of the Orthopaedic Research Society 12, 1994, 340-349.

Athanasiou et al., "Interspecies comparisons of in situ intrinsic mechanical properties of distal femoral cartilage," Journal of orthopaedic research: official publication of the Orthopaedic Research Society 9, 1991, 330-340.

Ballock et al., "Regulation of the expression of the type-II collagen gene in periosteum-derived cells by three members of the transforming growth factor-beta superfamily," Journal of orthopaedic research: official publication of the Orthopaedic Research Society 15, 1997, 463-467.

Banno et al., "Effects of tumor necrosis factor-alpha (TNF alpha) in epidermal keratinocytes revealed using global transcriptional profiling," The Journal of biological chemistry 279, 2004, 32633-32642.

Barde et al., "Efficient control of gene expression in the hematopoietic system using a single Tet-on inducible lentiviral vector," Molecular therapy: the journal of the American Society of Gene Therapy 13, 2006, 382-390.

Bartsevich et al., "Engineered zinc finger proteins for controlling stem cell fate," Stem Cells 21, 2003, 632-637.

Basile et al., "Freeze-dried tendon allografts as tissue-engineering scaffolds for Gdf5 gene delivery," Molecular therapy : the journal of the American Society of Gene Therapy 16, 2008, 466-473.

Bauermeister et al., "Distinct regulation of IL-8 and MCP-1 by LPS and interferon-gamma-treated human peritoneal macrophages," Nephrology, dialysis, transplantation: official publication of the European Dialysis and Transplant Association—European Renal Association 13, 1998, 1412-1419.

Beerli et al., "Chemically regulated zinc finger transcription factors," J Biol Chern, 2000, 275(42): p. 32617-27.

Beerli et al., "Engineering polydactyl zinc-finger transcription factors," Nat Biotechnol 20, 2002, 135-141.

Beerli et al., "Positive and negative regulation of endogenous genes by designed transcription factors," Proc Natl Acad Sci U S A 97, 2000, 1495-1500.

Beerli et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.

Beltran et al., "Re-activation of a dormant tumor suppressor gene maspinby designed transcription factors," Oncogene 26, 2007, 2791-2798.

Benedetti et al., "Repair or Replace? Exploiting Novel Gene and Cell Therapy Strategies for Muscular Dystrophies," FEBS Journal (2013).

Berghella et al., "Reversible immortalization of human myogenic cells by site-specific excision of a retrovirally transferred oncogene," Human gene therapy 10, 1999, 1607-1617.

Bhakta et al., "Highly active zinc-finger nucleases by extended modular assembly," Genome Res, 2013, 530-538.

Bhattacharyya et al., "Domains, motifs, and scaffolds: the role of modular interactions in the evolution and wiring of cell signaling circuits," Annual review of biochemistry 75, 2006, 655-680.

Bian et al., "Dynamic compressive loading enhances cartilage matrix synthesis and distribution and suppresses hypertrophy in hMSC-laden hyaluronic acid hydrogels," Tissue engineering Part A 18, 2012, 715-724.

Bian et al., "Hydrogels that mimic developmentally relevant matrix and N-cadherin interactions enhance MSC chondro genesis," Proceedings of the National Academy of Sciences of the United States of America 110, 2013, 10117-10122.

Bidou, L. et al., "Sense from nonsense: therapies for premature stop codon diseases," Trends in Molecular Medicine 18, 2012, 679-688.

Biffi et al., "Lentiviral hematopoietic stemcell gene therapy benefits metachromatic leukodystrophy," Science 341, 2013, 1233158.

Bitton, "The economic burden of osteoarthritis," The American journal of managed care 15, 2009, S230-235.

Blancafort et al., "Scanning the human genome with combinatorial transcription factor libraries," Nat Biotechnol 21, 2003, 269-274.

Bloquel et al., "Gene therapy of collagen-induced arthritis by electrotransfer of human tumor necrosis factor-alpha soluble receptor I variants," Human gene therapy 15, 2004, 189-201.

Boch et al., "Breaking the code of DNA binding specificity of TAL-type III effectors," Science 326, 2009, 1509.

Boekhoudt et al., "Communication between NF-kappa B and Sp1 controls histone acetylation within the proximal promoter of the monocyte chemoattractant protein 1 gene," Journal of immunology 170, 2003, 4139-4147.

Bonadio et al., "Localized, direct plasmid gene delivery in vivo: prolonged therapy results in reproducible tissue regeneration," Nature medicine 5, 1999, 753-759.

Bonaldo et al., "Cellular and molecular mechanisms of muscle atrophy," Disease models & mechanisms 6, 2013, 25-39.

Bondeson et al., "Adenoviral gene transfer of the endogenous inhibitor IkappaBalpha into human osteoarthritis synovial fibroblasts demonstrates that several matrix metalloproteinases and aggrecanases are nuclear factor-kappaB-dependent," The Journal of rheumatology 34, 2007, 523-533.

Bowles etak, "Phase 1 Gene Therapy for Duchenne Muscular Dystrophy Using a Translation Optimized AAV Vector," Molecular Therapy 20, 2012, 443-455.

Brunet et al., "Chromosomal translocations induced at specific loci in human stem cells," Proc Natl Acad Sci USA, 2009, 106:10620-10625.

Buler et al. "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, 2012, vol. 287, No. 3, pp. 1847-1860.

(56) References Cited

OTHER PUBLICATIONS

Bultmann et al., "Targeted transcriptional activation of silent oct4 pluripotency gene by combining designer TALEs and inhibition of epigenetic modifiers," Nucleic Acids Res 40, 2012, 5368-5377.
Butler et al., "Functional tissue engineering: the role of biomechanics," Journal of biomechanical engineering 122, 2000, 570-575.
Caplan, "Review: mesenchymal stem cells: cell-based reconstructive therapy in orthopedics," Tissue engineering 11, 2005, 1198-1211.
Carey et al., "Reprogramming of murine and human somatic cells using a single polycistronic vector," Proc. Natl. Acad. Sci., 2009, 106:157-162.
Carroll, "Genome engineering with zinc-finger nucleases," Genetics 188, 2011, 773-782.
Cerletti et al., "Highly efficient, functional engraftment of skeletal muscle stem cells in dystrophic muscles," Cell 134, 2008, 37-47.
Cermak et al., "Efficient design and assembly of custom TALEN and other TAL effector-based constructs for DNA targeting," Nucleic Acids Res, 2011, 39(12): 1-11.
Chao et al., "Engineering cartilage and bone using human mesenchymal stem cells," Journal of orthopaedic science: official journal of the Japanese Orthopaedic Association 12, 2007, 398-404.
Chapdelaine et al., "Meganucleases can restore the reading frame of a mutual dystrophin," Gene therapy 17, 2010, 846-858.
Cheng et al., "Multiplexed activation of endogenous genes by CRISPR-on, an RNA-guided transcriptional activator system," Cell Res, 2013, 23(10): p. 1163-1171.
Cho et al., "Analysis of off-target effects of CRISPR/Cas-derived RNA-guided endonucleases and nickases," Genome Res, 2014, 24:132-141.
Cho et al., "Targeted genome engineering in human cells with the Cas9 RNA-guided endonuclease," Nat Biotechnol 31, 2013, 230-232.
Choy et al., "The problem of choice: current biologic agents and future prospects in RA," Nature reviews Rheumatology 9, 2013, 154-163.
Christian et al., "Targeting DNA double-strand breaks with TAL effector nucleases," Genetics 186, 2010, 757-761.
Cirak et al., "Exon skipping and dystrophin restoration in patients with Duchenne muscular dystrophy after systemic phosphorodiamidate morpholino oligomer treatment: anopen-label, phase 2, dose-escalation study," Lancet 378, 2011, 595-605.
Cohen et al., "Psoriasis associated with ulcerative colitis and Crohn's disease," Journal of the European Academy of Dermatology and Venereology 23, 2009, 561-565.
Congetai., "Multiplex Genome Engineering Using CRISPR/Cas Systems," Science 339, 2013, 819-823.
Cornu et al., "DNA-binding specificity is a major determinant of the activity and toxicity of zinc-finger nucleases," MolTher, 2008, 16:352-358.
Cornu et al., "Quantification of zinc finger nuclease-associated toxicity," Meth Mol Biol, 2010, 649:237-245.
Corsi et al., "Regenerative medicine in orthopaedic surgery," Journal of orthopaedic research: official publication of the Orthopaedic Research Society 25, 2007, 1261-1268.
Cradick et al., "CRISPR/Cas9 systems targeting beta-globin and CCR5 genes have substantial off-target activity," Nucleic Acids Res, 2013, 41(20): p. 9584-92.
Craft et al., "Generationof articular chondrocytes from human pluripotent stem cells," Nature biotechnology 33, 2015, 638-645.
Croes et al., "Proinflammatory Mediators Enhance the Osteogenesis of Human Mesenchymal Stem Cells after Lineage Commitment," PloS one 10, 2015, e0132781.
Cucchiarini et al., "Direct rAAV SOX9 administration for durable articular cartilage repair with delayed terminal differentiation and hypertrophy in vivo," Journal of molecular medicine 91, 2013, 625-636.
Dang et al., "Natural polymers for gene delivery and tissue engineering," Advanced drug delivery reviews 58, 2006, 487-499.

Darabi et al., "Human ES-and iPS-derived myogenic progenitors restore dystrophin and improve contractility upon transplantation in dystrophic mice," Cell Stem Cell 10, 2012, 610-619.
Daya et al., "Gene therapy using adeno-associated virus vectors," Clinical microbiology reviews 21, 2008, 583-593.
Deng et al., "Transcriptional regulation of increased CCL2 expression in pulmonary fibrosis involves nuclear factor-kappaB and activator protein-1," The international journal of biochemistry & cell biology 45, 2013, 1366-1376.
Dezawa et al., "Bone marrow stromal cells generate muscle cells and repair muscle degeneration," Science Signaling 309, 2005, 314.
DiCarlo et al., "Biomaterial effects in articular cartilage tissue engineering using poly glycolic acid, a novel marine origin biomaterial, IGF-I, and TGF-beta 1," Proceedings ofthe Institution of Mechanical Engineers Part H, Journal of engineering in medicine 223, 2009, 63-73.
Diekman et al., "Cartilage tissue engineering using differentiated and purified induced pluripotent stem cells," Proc. Natl. Acad. Sci., 2012, 109:19172-19177.
Diekman et al., "Chondrogenesis of adult stem cells from adipose tissue and bone marrow: inductionby growth factors and cartilage-derived matrix," Tissue engineering Part A 16, 2010, 523-533.
Ding et al., "A TALEN Genome-Editing System for Generating Human Stem Cell-Based Disease Models," 2013, Cell Stem Cell 12, 238-251.
Ding et al., "Enhanced efficiency of human pluripotent stem cell genome editing through replacing TALENs with CRISPRs," Cell Stem Cell, 2013, 12:393-394.
Dissen et al., "In vivo manipulation of gene expression in non-human primates using lentiviral vectors as delivery vehicles," Methods 49, 2009, 70-77.
Doyle et al., "TAL Effector-Nucleotide Targeter (TALE-NT) 2.0: tools for TAL effector design and target prediction," Nucleic Acids Res 40, 2012, W117-122.
Doyon et al., "Enhancing zinc-finger-nuclease activity with improved obligate heterodimeric architectures," Nat Methods 8, 2010, 74-79.
Duan et al., "Circular intermediates of recombinant adeno-associated virus have defined structural characteristics responsible for long-term episo mal persistence in muscle tissue," Journal of virology 72, 1998, 8568-8577.
Dull et al., "A third-generation lentivirus vector with a conditional packaging system," Journal of virology 72, 1998, 8463-8471.
Edelstein et al. Gene therapy clinical trials worldwide 1989-2004—an overview. J. Gene Med., 2004, vol. 6, pp. 597-602.
Elliott et al., "Tensile properties of articular cartilage are altered by meniscectomy in a canine model of osteoarthritis," Journal of orthopaedic research: official publication of the Orthopaedic Research Society 17, 1999, 503-508.
Engler et al., "Matrix elasticity directs stem cell lineage specification," Cell 126, 2006, 677-689.
Erickson et al., "High mesenchymal stem cell seeding densities in hyaluronic acid hydrogels produce engineered cartilage with native tissue properties," Acta biomaterialia 8, 2012, 3027-3034.
Estes et al., "Isolation of adipose-derived stem cells and their induction to a chondro genic phenotype," Nature protocols 5, 2010, 1294-1311.
Esvelt et al., "Orthogonal Cas9 proteins for RNA-guided gene regulationand editing," Nature Methods, 2013, 10(11):1116-21.
Evans et al., "Arthritis gene therapy and its tortuous path into the clinic," Translational research: the journal of laboratory and clinical medicine 161, 2013, 205-216.
Farinelli et al., "Lentiviral vectors for the treatment of primary immunodeficiencies," J Inherit Metab Dis, 2014, 37:525-533.
Farndale et al., "Improved quantitation and discrimination of sulphated glycosaminoglycans by use of dimethylmethylene blue," Biochimica etbiophysica acta 883, 1986, 173-177.
Farzadfard et al., "Tunable and Multifunctional Eukaryotic Transcription Factors Based on CRISPR/Cas," ACS Synth Biol, 2013, 604-613.
Fernandes et al., "The role of cytokines in osteoarthritis pathophysiology," Biorheology 39, 2002, 237-246.

(56) References Cited

OTHER PUBLICATIONS

Fishbein et al., "Adenoviral vector tethering to metal surfaces via hydrolyzable cross-linkers for the modulation of vector release and transduction," Biomaterials 34, 2013, 6938-6948.
Flanigan et al., "Mutational spectrum of DMD mutations in dystrophinopathy patients: application of modern diagnostic techniques to a large cohort," Human mutation 30, 2009, 30(12): 1657-1666.
Fonfara et al., "Phylogeny of Cas9 determines functional exchangeability of dual-RNA and Cas9 among orthologous type II CRISPR-Cas systems," Nucleic Acids Res, 2014, 42(4): 2577-2590.
Fu et al., "High-frequency off-target mutagenesis induced by CRISPR-Cas nucleases in human cells," Nat Biotechnol, 2013, 31(9): p. 822-6.
Fu et al., "Improving CRISPR-Cas nuclease specificity using truncated guide RNAs," 2014, Nat Biotechnol 32, 279-284.
Furman et al., "Targeting pro-inflammatory cytokines following joint injury: acute intra-articular inhibition of interleukin-1 following knee injury prevents post-traumatic arthritis," Arthritis research & therapy 16, 2014, R134.
Gaj et al., "Targeted gene knockout by direct delivery of zinc-finger nuclease proteins," Nature Methods, 2012, 9(8): 805-807.
Gaj et al., "ZFN, TALEN, and CRISPR/Cas-based methods for genome engineering," Trends Biotechnol, 2013, 31:397-405.
Gao et al., "Stem cells for tissue engineering of articular cartilage," Proceedings of the Institution of Mechanical Engineers Part H, Journal of engineering in medicine 221, 2007, 441-450.
Garaulet et al., "IL10 released by a new inflammation-regulated lentiviral system efficiently attenuates zymosan-induced arthritis," Molecular therapy: the journal of the American Society of Gene Therapy 21, 2013, 119-130.
Gardner et al., "Construction of a genetic toggle switch in *Escherichia coli*," Nature 403, 2000, 339-342.
Garg et al., "Engineering synthetic TAL effectors with orthogonal target sites," Nucleic Acids Res, 2012, 40(15): 7584-7595.
Garrigues et al., "Use of an insulating mask for controlling anisotropy in multilayer electrospun scaffolds for tissue engineering," J Mater Chem 20, 2010, 8962-8968.
GenBank accession No. AK019325 (2010).
GenBank accession No. BB730912 (2001).
GenBank accession No. BC010291 (2006).
GenBank accession No. BC026642.1 (2007).
GenBank accession No. BI143915 (2001).
GenBank accession No. NM_020562 (2004).
Gendron et al., "Proteolytic activities of human ADAMTS-5: comparative studies with ADAMTS-4," The Journal of biological chemistry 282, 2007, 18294-18306.
Georgopoulos et al., "Transmembrane TNF is sufficient to induce localized tissue toxicity and chronic inflammatory arthritis in transgenic mice," Journal of inflammation 46, 1996, 86-97.
Gersbach et al., "Biomaterial-mediated retroviral gene transfer using self-assembled monolayers," Biomaterials 28, 2007, 5121-5127.
Gersbach et al., "Genetic engineering for skeletal regenerative medicine," Annual review of biomedical engineering 9, 2007, 87-119.
Gersbach et al., "In vitro and in vivo osteoblastic differentiation of BMP-2- and Runx2-engineered skeletal myoblasts," Journal of cellular biochemistry 100, 2007, 1324-1336.
Gersbach et al., "Targeted plasmid integration into the human genome by an engineered zinc-finger recombinase," Nucleic Acids Res, 2011, 39(17):7868-7878.
Gerstenfeld et al., "Impaired fracture healing in the absence of TNF-alpha signaling: the role of TNF-alpha in endochondral cartilage resorption," Journal of bone and mineral research: the official journal of the American Society for Bone and Mineral Research 18, 2003, 1584-1592.
Gertz et al., "Transposase mediated construction of RNA-seq libraries," Genome Res 22, 2012, 134-141.

Giacca et al., "Virus-mediated gene delivery for human gene therapy," Journal of controlled release: official journal of the Controlled Release Society 161, 2012, 377-388.
Ginn et al., "Gene therapy clinical trials worldwide to 2012—an update," The journal of gene medicine 15, 2013, 65-77.
Glass et al., "Tissue-engineered cartilage with inducible and tunable immunomodulatory properties," Biomaterials 35, 2014, 5921-5931.
Glasson et al., "Deletion of active ADAMTS5 prevents cartilage degradation in a murine model of osteoarthritis," Nature, 31 2005, 434(7033):644-648.
Goemans et al., "Systemic administration of PRO051 in Duchenne's muscular dystrophy," The New England journal of medicine 364, 2011, 1513-1522.
Goldring, "Chondrogenesis, chondrocyte differentiation and articular cartilage metabolism in health and osteoarthritis," Therapeutic advances in musculoskeletal disease 4, 2012, 269-285.
Goodrich et al., "Optimization of scAAVIL-1ra In Vitro and In Vivo to Deliver High Levels of Therapeutic Protein for Treatment of Osteoarthritis," Molecular therapy Nucleic acids 2, 2013, e70.
Gopinath et al., "Stem cell review series: aging of the skeletal muscle stem cell niche," Aging cell 7, 2008, 590-598.
Gorman et al., "Treatment of ankylosing spondylitis by inhibition of tumor necrosis factor alpha," The New England journal of medicine 346, 2002, 1349-1356.
Gou et al., "A novel approach for the construction of multiple shRNA expression vectors," J Gene Med, 2007, 9(9): p. 751-63.
Gouze et al., "In vivo gene delivery to synoviumby lentiviral vectors," Molecular therapy: the journal of the American Society of Gene Therapy 5, 2002, 397-404.
Gouze et al., "Lentiviral-mediated gene delivery to synovium potent intra-articular expression with amplification by inflammation," Molecular therapy: the journal of the American Society of Gene Therapy 7, 2003, 460-466.
Gouze et al., "Transgene persistence and cell turnover in the diarthrodial joint: implications for gene therapy of chronic joint diseases," Molecular therapy: the journal of the American Society of Gene Therapy 15, 2007, 1114-1120.
Grandaliano et al., "Gamma interferon stimulates monocyte chemotactic protein (MCP-1) in human mesangial cells," The Journal of laboratory and clinical medicine 123, 1994, 282-289.
Grant et al., "Col2-GFP reporter marks chondrocyte lineage and chondrogenesis during mouse skeletal development," Developmental Dynamics, 2000, 218:394-400.
Graslund et al., "Exploring strategies for the design of artificial transcription factors: targeting sites proximal to known regulatory regions for the induction of γ-globin expression and the treatment of sickle cell disease," J Biol Chem, 2005, 280(5):3707-3714.
Greber et al., "Intronically encoded siRNAs improve dynamic range of mammalian gene regulation systems and toggle switch," Nucleic acids research 36, 2008, e101.
Gregorevic et al., "Systemic delivery of genes to striated muscles using adeno-associated viral vectors," Nat Med, 2004, 10(8):828-834.
Grimm et al., "Fatality in mice due to oversaturation of cellular microRNA/short hairpin RNA pathways," Nature 441, 2006, 537-541.
Guo et al., "Directed evolution of an enhanced and highly efficient FokI cleavage domain for zinc finger nucleases," J Mol Biol, 2010, 400, 96-107.
Guschin et al., "A rapid and general assay for monitoring endogenous gene modification," Methods Mol Biol 649, 2010, 247-256.
Hao et al., "The stability of mRNA influences the temporal order of the induction of genes encoding inflammatory molecules," Nat Immunol., 2009, 10(3):281-288.
Hedbom et al., "Molecular aspects of pathogenesis in osteoarthritis: the role of inflammation," Cellular and molecular life sciences: CMLS 59, 2002, 45-53.
Heidens et al., "Catabolic factors and osteoarthritis-conditioned medium inhibit chondrogenesis of human mesenchymal stem cells," Tissue engineering Part A 18, 2012, 45-54.
Helmick et al., "Estimates of the prevalence of arthritis and other rheumatic conditions in the United States. Part I," Arthritis and rheumatism 58, 2008, 15-25.

(56) References Cited

OTHER PUBLICATIONS

Hockemeyer et al., "Efficient targeting of expressed and silent genes in human ESCs and iPSCs using zinc-finger nucleases," Nat Biotechnol, 2009, 27(9): p. 851-7.
Hockemeyer et al., "Genetic engineering of human ES and iPS cells using TALE nucleases," Nat Biotechnol 29, 2011, 731-734.
Hoffman et al., "Dystrophin: the protein product of the Duchenne muscular dystrophy locus," Cell, 1987, 51:919-928.
Holt et al., "Human hematopoietic stem/progenitor cells modified by zinc-finger nucleases targeted to CCR5 control HIV-1 in vivo," Nat Biotechnol, 2010, 28(8):839-847.
Hotta et al., "Isolation of human iPS cells using EOS lentiviral vectors to select for pluripotency," Nature methods 6, 2009, 370-376.
Hou et al., "Efficient genome engineering in human pluripotent stem cells using Cas9 from Neisseria meningitidis," Proc Nad Acad Sci USA, 2013, 110:15644-15649.
Hou et al., "Identification of a NF-kappaB site in the negative regulatory element (epsilon-NRAII) of human epsilon-globin gene and its binding protein NF-kappaB p50 inthe nuclei of K562 cells," Cell research 12, 2002, 79-82.
Hsu et al., "Development and applications of CRISPR-Cas9 for genome engineering," Cell 157, 2014, 1262-1278.
Hsu et al., "Dissecting Neural Function Using Targeted Genome Engineering Technologies", ACS Chem. Neurosci., 2012, pp. 603-610.
Hsu et al., "DNA targeting specificity of RNA-guided Cas9 nucleases," Nature Biotechnology 31, 2013, 827-832.
Hu et al., "Development of adenovirus immobilization strategies for in situ gene therapy," The journal of gene medicine 10, 2008, 1102-1112.
Hu et al., "Digoxigenin modification of adenovirus to spatially control gene delivery from chitosan surfaces," Journal of controlled release : official journal of the Controlled Release Society 135, 2009, 250-258.
Hu et al., "Localized viral vector delivery to enhance in situ regenerative gene therapy," Gene therapy 14, 2007, 891-901.
Hu et al., "The use of reactive polymer coatings to facilitate gene delivery from poly (epsilon-caprolactone) scaffolds," Biomaterials 30, 2009, 5785-5792.
Humbert et al., "Targeted gene therapies: tools, applications, optimization", Critical Reviews in Biochemistry and Molecular Biology, CRC Press, vol. 47, No. 3, 2012, pp. 264-281.
Hwang et al., "Efficient in vivo genome editing using RNA-Nucleases," Nat Biotechnol, 2013, 31(3):p. 227-9.
Hwang et al., "Regulation of osteogenic and chondrogenic differentiation of mesenchymal stemcells in PEG-ECM hydrogels," Cell and tissue research 344, 2011, 499-509.
Jang et al., "Engineering bio material systems to enhance viral vector gene delivery," Molecular therapy: the journal of the American Society of Gene Therapy 19, 2011, 1407-1415.
Jinek et al., "A programmable dual-RNA-guided DNA endonuclease in adaptive bacterial immunity," Science 337, 2012, 816-821.
Jinek et al., "RNA-pro grammed genome editing in human cells. eLife 2," e00471, 2013.
Jinek et al., "Structures of Cas9 endonucleases reveal RNA-mediated conformational activation," Science, 2014, 343(6176): 1247997.
Johnson et al., "A stem cell-based approach to cartilage repair," Science 336, 2012, 717-721.
Joung et al., "TALENs: a widely applicable technology for targeted genome editing," Nature Reviews Molecular Cell Biology 14, 2013, 49-55.
Jurvelin et al., "Optical and mechanical determination of Poisson's ratio of adult bovine humeral articular cartilage," Journal of biomechanics 30, 1997, 235-241.
Kapoor et al., "Role of proinflammatory cytokines in the pathophysiology of osteoarthritis," Nature reviews Rheumatology 7, 2011, 33-42.
Kay et al., "Intra-articular gene delivery and expression of interleukin-IRa mediated by self-complementary adeno-associated virus," The journal of gene medicine 11, 2009, 605-614.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns et al., "Cas9 effector-mediated regulation of transcription and differentiation in human pluripotent stem cells," Development, 2014, 141(1): p. 219-23.
Keffer et al., "Transgenic mice expressing human tumour necrosis factor: a predictive genetic model of arthritis," EMBO J., 1991, 10(13):4025-4031.
Khoury et al., "Inflammation-inducible anti-TNF gene expression mediated by intra-articular injection of serotype 5 adeno-associated virus reduces arthritis," The journal of gene medicine 9, 2007, 596-604.
Kim et al., "Fibrous hyaluronic acid hydrogels that direct MSC chondro genesis through mechanical and adhesive cues," Biomaterials 34, 2013, 5571-5580.
Kim et al., "Generation of human induced pluripotent stem cells from osteoarthritis patient-derived synovial cells," Arthritis and rheumatism 63, 2011, 3010-3021.
Kim et al., "Surrogate reporters for enrichment of cells with nuclease-induced mutations," Nat Methods, 2011, 8:941-943.
Kim et al., "TALENs and ZFNs are associated with different mutation signatures," Nat Methods, 2013, 10(3):185.
Kim et al., "Transient exposure to TGF-beta3 improves the functional chondrogenesis of MSC-laden hyaluronic acid hydrogels," Journal of the mechanical behavior of biomedical materials 11, 2012, 92-101.
Kimmerling et al., "Sustained intra-articular delivery of IL-1RA fromathermally-responsive elastin-like polypeptide as a therapy for post-traumatic arthritis," European cells & materials 29, 2015, 124-139; discussion 139-140.
Kimura et al., "Cell-lineage regulated myogenesis for dystrophin replacement: a novel therapeutic approach for treatment of muscular dystrophy," Hum Mol Genet 17, 2008, 2507-2517.
Kiskinis et al., "Pathways disrupted in human ALS motor neurons identified through genetic correction of mutant SOD1," Cell stem cell 14, 2014, 781-795.
Klein-Marcuschamer et al., "De novo metabolic engineering and the promise of synthetic DNA," Advances in biochemical engineering/biotechnology 120, 2010, 101-131.
Kobayashi et al., "Programmable cells: interfacing natural and engineered gene networks," Proceedings of the National Academy of Sciences of the United States of America 101, 2004, 8414-8419.
Kobayashi et al., "Transcriptional induction of ADAMTS5 by an NF-kappaB family member RelA/p65 in chondrocytes during osteoarthritis development," The Journal of biological chemistry, 2013.
Kock et al., "Tissue engineering of functional articular cartilage: the current status," Cell and tissue research 347, 2012, 613-627.
Konermann et al., "Optical control of mammalian endogenous transcription and epigenetic states," Nature, 2013, 500(7463): p. 472-6.
Konieczny et al., "Gene and cell-mediated therapies for muscular dystrophy," Muscle Nerve, 2013, 47:649-663.
Kramer et al. "An engineered epigenetic transgene switch in mammalian cells," Nature biotechnology 22, 2004, 867-870.
Kramer et al., "Embryonic stem cell-derived chondro genic differentiation in vitro: activation by BMP-2 and BMP-4," Mechanisms of development 92, 2000, 193-205.
Kretlow et al., "Injectable matrices and scaffolds for drug delivery in tissue engineering," Advanced drug delivery reviews 59, 2007, 263-273.
Kubokawa et al., "Molecular characterization of the 5'-UTR of retinal dystrophin reveals a cryptic intron that regulates translational activity," Molecular Vision, 2010, vol. 16, pp. 2590-2597.
Kumar et al., "Systematic determination of the packaging limit of lentiviral vectors," Human gene therapy, 2001, 12:1893-1905.
Kyte et al., "A Simple Method for Displaying the Hydropathic Character of a Protein," J. Mol. Biol., 1982, 157:105-132.

(56) References Cited

OTHER PUBLICATIONS

Labow et al., "Absence of IL-1 signaling and reduced inflammatory response in IL-1 type I receptor-deficient mice," Journal of immunology 159, 1997, 2452-2461.
Langmead et al., "Ultrafast and memory-efficient alignment of short DNA sequences to the human genome," Genome biology 10, 2009, R25.
Larson et al., "CRISPR interference (CRISPRi) for sequence-editing control of gene expression," Nat Protoc, 2013, 8(11): p. 2180-96.
Latta-Mahieu et al., "Gene transfer of a chimeric trans-activator is immunogenic and results in short-lived transgene expression," Human Gene Therapy, 2002, vol. 13, No. 13, pp. 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lau et al., "Overexpression of lysyl oxidase to increase matrix crosslinking and improve tissue strength in dermal wound healing," Annals of biomedical engineering 34, 2006, 1239-1246.
LeBaron et al., "Ex vivo synthesis of articular cartilage," Biomaterials 21, 2000, 2575-2587.
Lee et al., "Early induction of a prechondrogenic population allows efficient generation of stable chondrocytes from humaninduced pluripotent stemcells," FASEB journal: official publication of the Federationof American Societies for Experimental Biology 29, 2015, 3399-3410.
Lee et al., "Regeneration of the articular surface of the rabbit synovial joint by cell homing: a proof of concept study," Lancet 376, 2010, 440-448.
Lee et al., "Targeted chromosomal deletions in human cells using zinc finger nucleases," Genome research 20, 2010, 81-89.
Lei et al., "Cell-controlled and spatially arrayed gene delivery from fibrin hydrogels," Biomaterials 30, 2009, 3790-3799.
Leonard et al., "Role of transforming growth factor-beta in chondrogenic pattern formation in the embryonic limb: stimulation of mesenchymal condensation and fibronectin gene expression by exogenenous TGF-beta and evidence for endogenous TGF-beta-like activity," Developmental biology 145, 1991, 99-109.
LeRoux et al., "Compressive and shear properties of alginate gel: effects of sodium ions and alginate concentration," Journal ofbiomedical materials research 47, 1999, 46-53.
Levorson et al., "Fabrication and characterization of multiscale electrospun scaffolds for cartilage regeneration," Biomedical materials 8, 2013, 014103.
Li etal, "Invivo genome editing restores haemostasis ina mouse model of haemophilia," Nature 475, 2011, 217-221.
Li et al., "Marginal level dystrophin expression improves clinical outcome ina strain of dystrophin/utrophin double knockout mice," PLoS One, 2010, 5:e15286.
Li et al., "Modularly assembled designer TAL effector nucleases for targeted gene knockout and gene replacement in eukaryotes," Nucleic Acids Research, 2011, vol. 39, No. 14, pp. 6315-6325.
Li et al., "TNF-α regulates early differentiation of C2C12 myoblasts in an autocrine fashion," The FASEB Journal 15, 2001, 1413-1415.
Li et al., "Transcription activator-like effector hybrids for conditional control and rewiring of chromosomal transgene expression," Scientific Reports, 2012, 2:897, 7 pages.
Li, "TNF-alpha is a mitogen in skeletal muscle," American journal of physiology Cell physiology 285, 2003, C370-376.
Liang et al., "Engineeringbiological systems with synthetic RNA molecules," Mol Cell 43, 2011, 915-926.
Liao et al., "Sustained viral gene delivery through core-shell fibers," Journal of controlled release: official journal of the Controlled Release Society 139, 2009, 48-55.
Liu et al., "CTGF increases IL-6 expression in human synovial fibroblasts through integrin-dependent signaling pathway," PloS one 7, 2012, e51097.
Liu et al., "Regulation of an endogenous locus using a panel of designed zinc finger proteins targeted to accessible chromatin regions. Activation of vascular endothelial growth factor A," The Journal of biological chemistry 276, 2001, 11323-11334.
Lohmueller et al., "A tunable zinc finger-based framework for Boolean logic computation in mammalian cells," Nucleic Acids Res 40, 2012, 5180-5187.
Long et al., "Prevention of muscular dystrophy in mice by CRISPR/Cas9-mediated editing of germline DNA," Science 345, 2014, 1184-1188.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 20(11):2087-2097.
Lu et al., "The status of exon skipping as a therapeutic approach to duchenne muscular dystrophy," Molecular Therapy 19, 2011, 9-15.
Lund et al. "Promoter-targeted phage display selections with preassembled synthetic zinc finger libraries for endogenous gene regulation" Journal of Molecular Biology, vol. 340, 2004, pp. 599-613.
Luo et al., "Synthetic DNA delivery systems," Nature Biotechnology, 2000, vol. 18, pp. 33-37.
Ma et al., "Transcription activator-like effector nuclease (TALEN)-mediated gene correction in integration-free beta-thalassemia induced pluripotent stemcells," The Journal of biological chemistry 288, 2013, 34671-34679.
Mackay et al., "Chondrogenic differentiation of cultured human mesenchymal stem cells from marrow," Tissue engineering 4, 1998, 415-428.
Madry et al., "Cartilage constructs engineered from chondrocytes overexpressing IGF-I improve the repair of osteochondral defects ina rabbit model," European cells & materials 25, 2013, 229-247.
Madry et al., "TGF-beta-releasing scaffolds for cartilage tissue engineering," Tissue engineering Part B, Reviews, 2013.
Maeder et al., "Robust, synergistic regulation of human gene expression using TALE activators," Nat Methods 10, 2013, 243-245.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, "Targeted DNA demethylation and activation of endogenous genes using programmable TALE-TET1 fusion proteins," Nat Biotechnol, 2013, 31(12): p. 1137-42.
Mali et al., "Cas9 as a versatile tool for engineering biology," Nat Methods, 2013, 10(10): p. 957-63.
Mali et al., "CAS9 transcriptional activators for target specificity screening and paired nickases for cooperative genome engineering," Nat Biotechnol, 2013, 31(9): p. 833-8.
Mali et al., "RNA-guided human genome engineering via Cas9," Science, 2013, 339:823-826.
Mamchaoui et al., "Immortalized pathological human myoblasts: towards a universal tool for the study of neuromuscular disorders," Skelet Muscle 1, 2011, 1-11.
Marchand et al., "Role of the immune system in chronic pain," Nature reviews Neuroscience 6, 2005, 521-532.
Marcu et al., "NF-kappaB signaling: multiple angles to target OA," Current drug targets 11, 2010, 599-613.
Marijnissen et al., "Alginate as a chondrocyte-delivery substance in combination with a non-woven scaffold for cartilage tissue engineering," Biomaterials 23, 2002, 1511-1517.
Mauck et al.," Synergistic action of growth factors and dynamic loading for articular cartilage tissue engineering," Tissue engineering 9, 2003, 597-611.
McNulty et al., "The effects of adipokines on cartilage and meniscus catabolism," Connective tissue research 52, 2011, 523-533.
Mendell et al., "Dystrophin immunity in Duchenne's muscular dystrophy," New England Journal of Medicine 363, 2010, 1429-1437.
Mendenhall et al., "Locus-specific editing of histone modification at endogenous enhancers using programmable TALE-LSD1 fusions," Nat Biotechnol, 2013, 31(12): p. 1133-6.
Mengshol et al., "Interleukin-1 induction of collagenase 3 (matrix metalloproteinase 13) gene expression in chondrocytes requires

(56) References Cited

OTHER PUBLICATIONS p38, c-Jun N-terminal kinase, and nuclear factor kappaB: differential regulation of collagenase 1 and collagenase 3," Arthritis and rheumatism 43, 2000, 801-811.
Mercer et al., "Regulation of Endogenous Human Gene Expression by Ligand-Inducible TALE Transcription Factors," ACS Synth Biol, 2013, 29 pages.
Meszaros et al., "Prospects for treating osteoarthritis: enzyme-protein interactions regulating matrix metalloproteinase activity," Therapeutic advances inchronic disease 3, 2012, 219-229.
Michlewska et al., "Macrophage phagocytosis of apoptotic neutrophils is critically regulated by the opposing actions of pro-inflammatory and anti-inflammatory agents: key role for TNF-alpha," FASEB journal: official publication of the Federation of American Societies for Experimental Biology 23, 2009, 844-854.
Miller et al., "A TALE nuclease architecture for efficient genome editing," Nat Biotechnol 29, 2011, 143-148.
Miller et al., "An improved zinc-finger nuclease architecture for highly specific genome editing," Nature biotechnology 25, 2007, 778-785.
Moffat et al., "Novel nanofiber-based scaffold for rotator cuff repair and augmentation," Tissue engineering Part A 15, 2009, 115-126.
Moscou et al., "A simple cipher governs DNA recognition by TAL effectors," Science 326, 2009, 1501.
Mountziaris et al., "Dose effect of tumor necrosis factor-alpha on in vitro osteogenic differentiation of mesenchymal stem cells on biodegradable polymeric microfiber scaffolds," Biomaterials 31, 2010, 1666-1675.
Moutos et al., "A biomimetic three-dimensional woven composite scaffold for functional tissue engineering of cartilage," Nature materials 6, 2007, 162-167.
Moutos et al., "Functional properties of cell-seeded three-dimensionally woven poly(epsilon-caprolactone) scaffolds for cartilage tissue engineering," Tissue engineering Part A 16, 2010, 1291-1301.
Mow et al., "Biphasic creep and stress relaxation of articular cartilage in compression? Theory and experiments," Journal of biomechanical engineering 102, 1980, 73-84.
Mow et al., "Cartilage and diarthrodial joints as paradigms for hierarchical materials and structures," Biomaterials 13, 1992, 67-97.
Mow et al., "Mechano-electrochemical properties of articular cartilage: their inhomogeneities and anisotropies," Annual review of biomedical engineering 4, 2002, 175-209.
Mozzetta et al., "Regenerative pharmacology in the treatment of genetic diseases: the paradigm of muscular dystrophy," The international journal of biochemistry & cell biology 41, 2009, 701-710.
Mueller et al., "Functional characterization of hypertrophy in chondrogenesis of human mesenchymal stem cells," Arthritis and rheumatism 58, 2008, 1377-1388.
Murphy et al., "The in vitro transcription of the 7SK RNA gene by RNA polymerase III is dependent only on the presence of an upstream promoter," Cell, 1987, 51:81-87.
Mussolino et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Napetschnig et al., "Molecular basis of NF-kappaB signaling," Annual review of biophysics 42, 2013, 443-468.
Negroni et al., "In Vivo Myogenic Potential of Human CD133[+] Muscle-derived Stem Cells: A Quantitative Study," Molecular Therapy 17, 2009, 1771-1778.
Neumann et al., "Chondrogenesis ofhumanbone marrow-derived mesenchymal stemcells is modulated by complex mechanical stimulation and adenoviral-mediated overexpression of bone morphogenetic protein 2," Tissue engineering Part A 19, 2013, 1285-1294.
Nishimasu et al., "Crystal structure of Cas9 in complex with guide RNA and target DNA," Cell, 2014, 156(5): p. 935-49.

Nourbakhsh et al., "Interferon-beta promoters contain a DNA element that acts as a position-independent silencer on the NF-kappaB site," The EMBO journal 12, 1993, 451-459.
Ohshima et al., "Nucleotide sequence of mouse genomic loci including a gene or pseudogene for U6 (4.85S) nuclear RNA," Nucleic Acids Res, 1981, 9:5145-5158.
Ousema et al., "The inhibition by interleukin 1 of MSC chondrogenesis and the development of biomechanical properties in biomimetic 3D woven PCL scaffolds," Biomaterials 33, 2012, 8967-8974.
Ousterout et al., "Correction of dystrophin expression in cells from duehenne muscular dystrophy patients through genomic excision of exon 51 by zinc finger nucleases," Molecular therapy: the journal of the American Society of Gene Therapy 23, 2015, 523-532.
Ousterout et al., "Multiplex CRISPR/Cas9-based genome editing for correction of dystrophin mutations that cause Duchenne muscular dystrophy," Nature communications 6, 2015, 6244.
Ousterout et al., "Reading frame correction by targeted genome editing restores dystrophin expression in cells from Duchenne muscular dystrophy patients," Mol Ther, 2013, 21:1718-1726.
Outani et al., "Induction of chondrogenic cells from dermal fibroblast culture by defined factors does not involve a pluripotent state," Biochemical and biophysical research communications 411, 2011, 607-612.
Padmashali et al., "Engineering fibrinogen-binding VSV-G envelope for spatially- and cell-controlled lentivirus delivery thro ugh fibrin hydrogels," Biomaterials 32, 2011, 3330-3339.
Palacios et al., "TNF/p38alpha/polycomb signaling to Pax7 locus in satellite cells links inflammation to the epigenetic control of muscle regeneration," Cell stem cell 7, 2010, 455-469.
Paller et al., "Etanercept treatment for children and adolescents with plaque psoriasis," The New England journal of medicine 358, 2008, 241-251.
Palmer et al., "Gene-induced chondrogenesis of primary mesenchymal stemcells in vitro," Molecular therapy: the journal of the American Society of Gene Therapy 12, 2005, 219-228.
Palu et al., "In pursuit of new developments for gene therapy of human diseases," J. Biotechnol. vol. 68, 1999, pp. 1-13.
Pannier et al., "Controlled release systems for DNA delivery," Molecular therapy: the journal of the American Society of Gene Therapy 10, 2004, 19-26.
Papayannakos et al., "Understanding lentiviral vector chromatin targeting: working to reduce insertional mutagenic potential for gene therapy," Gene Ther, 2013, 20(6): p. 581-8.
Park et al., "Phenotypic alteration of eukaryotic cells using randomized libraries of artificial transcription factors," Nat Biotechnol 21, 2003, 1208-1214.
Park et al., "The effect of matrix stiffness on the differentiation of mesenchymal stem cells in response to TGF-beta," Biomaterials 32, 2011, 3921-3930.
Parnas et al., "A Genome-wide CRISPR Screen in Primary Immune Cells to Dissect Regulatory Networks," Cell 162, 2015, 675-686.
Pattanayak et al., "High-throughput profiling of off-target DNA cleavage reveals RNA-programmed Cas9 nuclease specificity," Nat Biotechnol, 2013, 31(9): p. 839-43.
Peault et al., "Stemand progenitor cells in skeletal muscle development, maintenance, and therapy," Molecular Therapy 15, 2007, 867-877.
Pei et al., "Bioreactors mediate the effectiveness of tissue engineering scaffolds," FASEB journal: official publication of the Federationof American Societies for Experimental Biology 16, 2002, 1691-1694.
Peng et al., "ESE-1 is a potent repressor of type II collagen gene (COL2A1) transcription in human chondrocytes," Journal of cellular physiology 215, 2008, 562-573.
Peralta Soler et al., "Tissue remodeling during tumor necrosis factor-induced apoptosis in LLC-PK1 renal epithelial cells," The American journal of physiology 270, 1996, F869-879.
Perez et al., "Establishment of HIV-1 resistance in CD4[+] T cells by genome editing using zinc-finger nucleases," Nature biotechnology 26, 2008, 808-816.
Perez-Pinera et al., "Advances in targeted genome editing," Current Opinionin Chemical Biology 16, 2012, 268-277.

(56) References Cited

OTHER PUBLICATIONS

Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nature methods 10, 2013, 973-976.
Perez-Pinera et al., "Synergistic and tunable human gene activation by combinations of synthetic transcription factors," Nat Methods 10, 2013, 239-242.
Perez-Pinera et al., "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III, Abstract 855, Saturday, May 19, 2012.
Persons et al., "Solving the problem of gamma-retroviral vectors containing long terminal repeats," Molecular therapy: the journal of the American Society of Gene Therapy 19, 2011, 229-231.
Persons, "Lentiviral vector gene therapy: effective and safe?" Mol Ther, 2010, 18(5): p. 861-2.
Pfaffl, "A new mathematical model for relative quantification in real-time RT-PCR," Nucleic acids research 29, 2001, e45.
Pfeiffer et al., "The effects of glycosaminoglycan content on the compressive modulus of cartilage engineered in type II collagen scaffolds," Osteoarthritis and cartilage / OARS, Osteoarthritis Research Society 16, 2008, 1237-1244.
Phillips et al., "Engineering graded tissue interfaces," Proceedings of the National Academy of Sciences of the United States of America 105, 2008, 12170-12175.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant et al., "Current status of pharmaceutical and genetic therapeutic approaches to treat DMD," Molecular Therapy 19, 2011, 830-840.
Ping et al., "Nuclear Factor-κB p65 Mediates the Assembly and Activation of the TNF-Responsive Element of the Murine Monocyte Chemoattractant-1 Gene," The Journal of Immunology 162, 1999, 727-734.
Polstein et al., "Light-inducible spatiotemporal control of gene activation by customizable zinc finger transcription factors," J Am Chem Soc, 2012, 134(40): p. 16480-3.
Popplewell et al., "Gene correction of a duchenne muscular dystrophy mutation by meganuclease-enhanced exon knock-in," Hum Gene Ther, 2013, 24:692-701.
Qi et al., "Repurposing CRISPR as anRNA-guided platform for sequence-specific control of gene expression," Cell 152, 2013, 1173-1183.
Ramos-Casals et al., "Autoimmune diseases induced by TNF-targeted therapies," Best practice & research Clinical rheumatology 22, 2008, 847-861.
Ran et al., "Double Nicking by RNA-Guided CRISPR Cas9 for Enhanced Genome Editing Specificity," Cell 154, 2013, 1380-1389.
Rebar et al., "Induction of angiogenesis in a mouse model using engineered transcription factors," Nat Med 8, 2002, 1427-1432.
Rebel et al., "Essential role for the p55 tumor necrosis factor receptor in regulating hematopoiesis at a stem cell level," The Journal of experimental medicine 190, 1999, 1493-1504.
Reed et al., "Composite tissue engineering on polycaprolactone nano fiber scaffolds," Annals of plastic surgery 62, 2009, 505-512.
Reid et al., "Tumor necrosis factor-alpha and muscle wasting: a cellular perspective," Respiratory research 2, 2001, 269-272.
Reyes et al., "Biomolecular surface coating to enhance orthopaedic tissue healing and integration," Biomaterials 28, 2007, 3228-3235.
Reyon et al., "FLASH assembly of TALENs for high-throughput genome editing," Nat Biotechnol 30, 2012, 460-465.
Rezzoug et al., "TNF-alpha is critical to facilitate hemopoietic stem cell engraftment and function," Journal of immunology 180, 2008 49-57.

Rousseau et al., "Endonucleases: tools to correct the dystrophin gene" The Journal of Gene Medicine, 2011, vol. 13, pp. 522-537.
Rowland et al., "Factors influencing the long-term behavior of extracellular matrix-derived scaffolds for musculoskeletal soft tissue repair," Journal of long-term effects of medical implants 22, 2012, 181-193.
Rowland et al., "The effects of crosslinking of scaffolds engineered from cartilage ECM on the chondro genic differentiation of MSCs," Biomaterials 34, 2013, 5802-5812.
Ruder et al., "Synthetic biology moving into the clinic," Science, 2011, 333(6047):1248-1252.
Saha et al., "Technical challenges in using human induced pluripotent stem cells to model disease," Cell stem cell 5, 2009, 584-595.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon et al., "Production and titration of lentiviral vectors," Current protocols in neuroscience, 2006, Chapter 4, Unit 4.21.1-4.21.24.
Sambrook et al., Molecular Cloning and Laboratory manual, Second Ed., Cold Spring Harbor (1989).
Samulski, "Expanding the AAV package," Nature biotechnology 18, 2000, 497-498.
Sands et al., "Infliximab maintenance therapy for fistulizing Crohn's disease," The New England journal of medicine 350, 2004, 876-885.
Schambach et al., "Biosafety features of lentiviral vectors," Human gene therapy 24, 2013, 132-142.
Schambach et al., "Clinical application of lentiviral vectors—concepts and practice," Current gene therapy 8, 2008, 474-482.
Schmid-Burgk et al., "A ligation-independent cloning technique for high-throughput assembly of transcription activator-like effector genes," Nat Biotechnol 31, 2012, 76-81.
Schneider et al., "NIH Image to ImageJ: 25 years of image analysis," Nature methods 9, 2012, 671-675.
Scholze et al., "TAL effectors are remote controls for gene activation," Current Opinion in Microbiology, vol. 14, 2011, pp. 47-53.
Schultz et al., "Recombinant adeno-associated virus transduction and integration," Molecular Therapy 16, 2008, 1189-1199.
Schwank et al., "Functional repair of CFTR by CRISPR/Cas9 in intestinal stem cell organoids of cystic fibrosis patients," Cell stem cell 13, 2013, 653-658.
Scott et al., "The links between joint damage and disability in rheumatoid arthritis," Rheumatology, 2000, 39(2):122-132.
Scott et al., "Tumor necrosis factor inhibitors for rheumatoid arthritis," The New England journal of medicine 355, 2006, 704-712.
Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifying agents in anti-cancer therapy," Biochimie, 2012, vol. 94, pp. 2264-2279.
Serra et al., "Expression of a truncated, kinase-defective TGF-beta type II receptor in mouse skeletal tissue promotes terminal chondrocyte differentiation and osteoarthritis," The Journal of cell biology 139, 1997, 541-552.
Seto et al., "Gene Replacement Therapies for Duchenne Muscular Dystrophy Using Adeno-Associated Viral Vectors," Current Gene Therapy, 2012, 12:139-151.
Setton et al., "Mechanical properties of canine articular cartilage are significantly altered following transection of the anterior cruciate ligament," Journal of orthopaedic research: official publication of the Orthopaedic Research Society 12, 1994, 451-463.
Setton et al., "The biphasic poroviscoelastic behavior of articular cartilage: role of the surface zone in governing the compressive behavior," Journal of biomechanics 26, 1993, 581-592.
Seyedin et al., "Cartilage-inducing factor-A. Apparent identity to transforming growth factor-beta," The Journal of biological chemistry 261, 1986, 5693-5695.
Shalem et al., "Genome-scale CRISPR-Cas9 knockout screening in human cells," Science 343, 2014, 84-87.

(56) References Cited

OTHER PUBLICATIONS

Sharma et al., "Efficiency of nonho mologous DNA end joining varies among somatic tissues, despite similarity in mechanism," Cellular and Molecular Life Science 68, 2011, 661-676.
Shea et al., "DNA delivery frompolymer matrices for tissue engineering," Nature biotechnology 17, 1999, 551-554.
Shinetai., "Lentivirus delivery by adsorption to tissue engineering scaffolds," Journal of biomedical materials research Part A 93, 2010, 1252-1259.
Shin et al., "Lentivirus immobilization to nanoparticles for enhanced and localized delivery from hydrogels," Molecular therapy: the journal of the American Society of Gene Therapy 18, 2010, 700-706.
Shinetai., "Phosphatidylserine immobilization of lentivirus for localized gene transfer," Biomaterials 31, 2010, 4353-4359.
Silva et al., "Meganucleases and other tools for targeted genome engineering: perspectives and challenges for gene therapy," Current gene therapy, 2011, 11:11-27.
Smith et al., "Tissue-engineering strategies for the tendon/ligament-to-bone insertion," Connective tissue research 53, 2012, 95-105.
Smith et al., "Whole-genome sequencing analysis reveals high specificity of CRISPR/Cas9 and TALEN-based genome editing in human iPSCs," Cell stem cell 15, 2014, 12-13.
Soldner et al., "Generation of isogenic pluripotent stem cells differing exclusively at two early onset Parkinson point mutations," Cell 146, 2011, 318-331.
Şöllü et al., "Autonomous zinc-finger nuclease pairs for targeted chromosomal deletion," Nucleic acids research 38, 2010, 8269-8276.
Soltz et al., "Interstitial fluid pressurization during confined compression cyclical loading of articular cartilage," Annals of biomedical engineering 28, 2000, 150-159.
Song et al., "Dnase-seq: a high-resolution technique for mapping active gene regulatory elements across the genome from mammalian cells," Cold Spring Harbor protocols 2010, pdb prot5384.
Song et al., "Open chromatin defined by DNaseI and FAIRE identifies regulatory elements that shape cell-type identify," Genome Res 21, 2011, 1757-1767.
Spiller et al., "Hydrogels for the repair of articular cartilage defects," Tissue engineering Part B, Reviews 17, 2011, 281-299.
Stahl et al., "Encoding Cell-Instructive Cues to PEG-Based Hydrogels via Triple Helical Peptide Assembly," Soft matter 8, 2012, 10409-10418.
Stanton et al., "ADAMTS5 is the major aggrecanase in mouse cartilage in vivo and in vitro," Nature 434, 2005, 648-652.
Steinert et al., "Enhanced in vitro chondrogenesis of primary mesenchymal stem cells by combined gene transfer," Tissue engineering Part A 15, 2009, 1127-1139.
Stern-Straeter et al., "Advances in skeletal muscle tissue engineering," In vivo 21, 2007, 435-444.
Sun et al., "Optimized TAL effector nucleases (TALENs) for use in treatment of sickle cell disease," Molecular bioSystems 8, 2012, 1255-1263.
Suzuki et al., "Targeted gene correction minimally impacts whole-genome mutational load in human-disease-specific induced pluripotent stem cell clones," Cell stem cell 15, 2014, 31-36.
Szulc et al., "A versatile tool for conditional gene expression and knockdown," Nature methods 3, 2006, 109-116.
Szyf, "Epigenetics, DNA methylation, and chromatin modifying drugs," Annual Review of Pharmacology and Toxicology, 2009, vol. 49, pp. 243-263.
Taniguchi-Ikeda et al., "Pathogenic exon-trapping by SVA retro transposon and rescue in Fukuyama muscular dystrophy," Nature 478, 2011, 127-131.
Taxonera et al., "Infliximab maintenance therapy is associated with decreases in direct resource use in patients with luminal or fistulizing Crohn's disease," Journal of clinical gastroenterology 43, 2009, 950-956.
Tebas et al., "Gene editing of CCR5 in autologous CD4 T cells of persons infected with HIV," N Engl J Med, 2014, 370:901-910.

Tedesco et al., "Repairing skeletal muscle: regenerative potential of skeletal muscle stemcells," J Clin Invest, 2010, 120:11-19.
Tedesco et al., "Stem Cell-Mediated Transfer of a Human Artificial Chromosome Ameliorates Muscular Dystrophy," Science Translational Medicine 3, 96ra78-96ra78, 2011.
Tedesco et al., "Transplantation of Genetically Corrected Human iPSC-Derived Progenitors in Mice with Limb-Girdle Muscular Dystrophy," Science Translational Medicine 4, 140ra189, 2012.
Teferedegne et al., "Mechanism of action of a distal NF-kappaB-dependent enhancer," Molecular and cellular biology 26, 2006, 5759-5770.
Tsai et al., "Dimeric CRISPR RNA-guided FokI nucleases for highly specific genome editing," Nature biotechnology 32, 2014, 569-576.
Tyring et al., "Etanercept and clinical outcomes, fatigue, and depression in psoriasis: double-blind placebo-controlled randomised phase III trial," Lancet 367, 2006, 29-35.
Urnov et al., "Highly efficient endogenous human gene correction using designed zinc-finger nucleases," Nature 435, 2005, 646-651.
Urnov et al.,"Genome editing with engineered zinc finger nucleases," Nat Rev Genet, 2010, 11(9):636-646.
Valonen et al., "In vitro generation of mechanically functional cartilage grafts based on adult human stem cells and 3D-woven poly(epsilon-caprolactone) scaffolds," Biomaterials 31, 2010, 2193-2200.
Van de Loo et al., "An inflammation-inducible adenoviral expression system for local treatment of the arthritic joint," Gene therapy 11, 2004, 581-590.
Van Putten et al., "Low dystrophin levels in heart can delay heart failure in mdx mice," J Mol Cell Cardiol, 2014, 69C:17-23.
Van Putten et al., "Low dystrophin levels increase survival and improve muscle pathology and function in dystrophin/utrophin double-knockout mice," FASEB J, 2013, 27:2484-2495.
Venkatesan et al., "SOX9 gene transfer via safe, stable, replication-defective recombinant adeno-associated virus vectors as a novel, powerful tool to enhance the chondro genic potential of human mesenchymal stemcells," Stem cell research& therapy 3, 2012, 22.
Veres et al., "Low incidence of off-target mutations in individual CRISPR-Cas9 and TALEN targeted human stem cell clones detected by whole-genome sequencing," Cell stem cell 15, 2014, 27-30.
Verma et al. "Gene therapy—promises, problems and prospects," Nature, vol. 389, pp. 239-242, 1997.
Verma et al., "Gene Therapy: Twenty-first century medicine," Annual Review of Biochemistry, vol. 74, 2005, pp. 711-738.
Verma, "Gene Therapy That Works," Science 341, 2013, 853-855.
Vickers et al., "Cross-linking affects cellular condensation and chondrogenesis in type II collagen-GAG scaffolds seeded with bo ne marrow-derived mesenchymal stem cells," Journal of orthopaedic research official publication of the Orthopaedic Research Society 28, 2010, 1184-1192.
Vierbuchen et al., "Direct conversion of fibroblasts to functional neurons by de fined factors," Nature 463, 2010, 1035-1041.
Vunjak-Novakovic et al., "Bioreactor cultivation conditions modulate the composition and mechanical properties of tissue-engineered cartilage," Journal of orthopaedic research: official publication of the Orthopaedic Research Society 17, 1999, 130-138.
Wang et al., "Adeno-associated virus vector carrying human minidystrophin genes effectively ameliorates muscular dystrophy in mdx mouse model," Proc Natl Acad Sci US A. (2000) 97(25):13714-13719.
Wang et al., "Lipopolysaccharide-induced MCP-1 gene expression in rat tubular epithelial cells is nuclear factor-kappaB dependent," Kidney international 57, 2000, 2011-2022.
Wang et al., "Multifunctional chondroitin sulphate for cartilage tissue-biomaterial integration," Nature materials 6, 2007, 385-392.
Wang et al., "One-Step Generation of Mice Carrying Mutations in Multiple Genes by CRISPR-Cas-Mediated Genome Engineering," Cell, 2013, 153(4): p. 910-8.
Watson et al., "scAAV-mediated gene transfer of interleukin-1-receptor antagonist to synovium and articular cartilage in large mammalian joints," Gene therapy 20, 2013, 670-677.
Weber et al., "Emergingbiomedical applications of synthetic biology," Nat Rev Genet, 2012, 13(1):21-35.

(56) References Cited

OTHER PUBLICATIONS

Weber et al., "Synthetic gene networks in mammalian cells," Current opinion inbiotechnology 21, 2010, 690-696.
Wehling et al., "Clinical responses to gene therapy injoints of two subjects with rheumatoid arthritis," Human gene therapy 20, 2009, 97-101.
Wehling et al., "Interleukin-lbeta and tumor necrosis factor alpha inhibit chondro genesis by human mesenchymal stem cells through NF-kappaB-dependent pathways," Arthritis and rheumatism 60, 2009, 801-812.
Weimer et al., "Benefits of recombinant adeno-associated virus (rAAV)-mediated insulinlike growth factor I (IGF-I) overexpression for the long-term reconstruction of human osteoarthritic cartilage by modulation of the IGF-I axis," Molecular medicine (Cambridge, Mass) 18, 2012, 346-358.
Wein et al., "Efficient bypass of mutations in dysferlin deficient patient cells by antisense-induced exon skipping," Hum Mutat 31, 2010, 136-142.
Weisel, "The mechanical properties of fibrin for basic scientists and clinicians," Biophysical chemistry 112, 2004, 267-276.
Welch et al., "PTC124 targets genetic disorders caused by nonsense mutations," Nature 447, 2007, 87-91.
Willard et al., "Use of cartilage derived from murine induced pluripotent stem cells for osteoarthritis drug screening," Arthritis & rheumatology, 2014, 66(11):3062-72.
Wiznerowicz et al., "Conditional suppression of cellular genes: lentivirus vector-mediated drug-inducible RNA interference," Journal ofvirology 77, 2003, 8957-8961.
Wiznerowicz et al., "Harnessing HIV for therapy, basic research and biotechnology," Trends in biotechnology 23, 2005, 42-47.
Woessner, "The determination of hydroxyproline in tissue and protein samples containing small proportions of this imino acid," Archives of biochemistry and biophysics 93, 1961, 440-447.
Wroblewska et al., "Mammalian synthetic circuits with RNA binding proteins for RNA-only delivery," Nature biotechnology 33, 2015, 839-841.
Wu et al., "Electrosprayed core-shell microspheres for protein delivery," Chemical communications (Cambridge, England) 46, 2010, 4743-4745.
Wuertz et al., "Inflammatory and catabolic signalling in intervertebral discs: the roles of NF-kappaB and MAP kinases," European cells & materials 23, 2012, 103-119; discussion 119-120.
Xie et al., "Multi-input RNAi-based logic circuit for identification of specific cancer cells," Science 333, 2011, 1307-1311.
Xu et al., "In vitro expansion of adipose-derived adult stromal cells in hypoxia enhances early chondro genesis," Tissue engineering 13, 2007, 2981-2993.
Yamashita et al., "Statin treatment rescues FGFR3 skeletal dysplasia phenotypes," Nature 513, 2014, 507-511.
Yan et al., "Drugging the undruggable: transcription therapy for cancer," Biochim Biophys Acta, 2013, 1835(1):76-85.
Yang et al., "Compound screening platform using human induced pluripotent stem cells to identify small molecules that promote chondrogenesis," Protein & cell 3, 2012, 934-942.
Yang et al., "Targeted and genome-wide sequencing reveal single nucleotide variations impacting specificity of Cas9 in human stem cells," Nature communications 5, 2014, 5507.
Yang, "Optimization of scarless human stem cell genome editing," Nucleic Acids Res, 2013, 41:9049-9061.
Yaszemski et al., Tissue engineering and novel delivery systems, 2004 (New York: Marcel Dekker).
Yin et al., "Genome editing with Cas9 in adult mice corrects a disease mutation and phenotype," Nature biotechnology 32, 2014, 551-553.
Yusa et al., "Targeted gene correction of ayantitrypsin deficiency in induced pluripotent stem cells," Nature 478, 2011, 391-394.
Zagury et al., "Toward a new generation of vaccines: The anti-cytokine therapeutic vaccines," Proceedings of the National Academy of Sciences of the United States of America, 2001, vol. 98, No. 14, pp. 8024-8029.
Zhang et al. "Efficient construction of sequence-specific TAL effectors for modulating mammalian transcription," Nat Biotechnol 29, 2011, 149-153.
Zhong et al., "Fractured polymer/silica fiber surface studied by tapping mode atomic force microscopy," Surface Science Letters 290, 1993, L688-L692.
Zhu et al., "Cellular senescence in human myoblasts is overcome by human telomerase reverse transcriptase and cyclin-dependent kinase 4: consequences in aging muscle and therapeutic strategies for muscular dystrophies," Aging cell 6, 2007, 515-523.
Zou et al., "Site-specific gene correction of a point mutation in human iPS cells derived from an adult patient with sickle cell disease," Blood 118, 2011, 4599-4608.
Zufferey et al., "Self-inactivating lentivirus vector for safe and efficient in vivo gene delivery," Journal of virology 72, 1998, 9873-9880.
International Search Report and Written Opinion for Application No. PCT/US14/41190 dated Dec. 17, 2014 (14 pages).
International Search Report and Written Opinion for Application No. PCT/US2015/062024 dated Feb. 12, 2016 (13 pages).

* cited by examiner

COMPOSITIONS, SYSTEMS AND METHODS FOR CELL THERAPY

CROSS-REFERENCE TO RELATED APPLICATIONS

This application is a national stage filing under 35 U.S.C. 371 of International Patent Application No. PCT/US2015/062024, which claims priority to U.S. Provisional Application No. 62/082,315, filed Nov. 20, 2014, which is incorporated herein by reference in its entirety.

SEQUENCE LISTING

The instant application includes a Sequence Listing which has been submitted electronically in ASCII format and is hereby incorporated by reference in its entirety. Said ASCII copy, created on Dec. 23, 2015, is named 028193-9207-WO00_Sequence_Listing.txt and is 8,906 bytes in size.

TECHNICAL FIELD

The present disclosure is directed to compositions and methods for cell therapy comprising an engineered cell.

BACKGROUND

Immunotherapy and regenerative medicine provides the exciting potential for cell-based therapies to treat many diseases and restore damaged tissues, but the inability to precisely control cell function has limited the ultimate success of this field. For over 40 years, gene therapy has been proposed as an approach to cure genetic diseases by adding functional copies of genes to the cells of patients with defined genetic mutations. However, this field has been limited by the available technologies for adding extra genetic material to human genomes. In recent years, the advent of synthetic biology has led to the development of technologies for precisely controlling gene networks that determine cell behavior. Several new technologies have emerged for manipulating genes in their native genomic context by engineering synthetic transcription factors that can be targeted to any DNA sequence. This includes new technologies that have enabled targeted human gene activation and repression, including the engineering of transcription factors based on zinc finger proteins, TALEs, and the CRISPR/Cas9 system. There remains a need for the ability to precisely regulate any gene as it occurs naturally in the genome, such as the rewiring of genetic circuits, as a means to address a variety of diseases and disorders while circumventing some of the traditional challenges of gene therapy.

SUMMARY

The present invention is directed to a composition for treating a subject having or suspected of having a disease, the composition comprising a modified cell comprising a modified endogenous gene, wherein an endogenous gene or fragment thereof is replaced with a transgene using a CRISPR/Cas9 system to generate the modified endogenous gene, the modified cell having an altered response to a cell signal or stimulus.

The present invention is directed to a composition for treating a subject having or suspected of having a disease or disorder, the composition comprising a modified cell comprising a modified endogenous gene, wherein an endogenous gene or fragment thereof comprises a signal peptide and the signal peptide is deleted or knocked out using a CRISPR/Cas9 system to generate the modified endogenous gene, the modified cell having an altered response to a cell signal or stimulus.

The present invention is directed to a method of preventing, treating or ameliorating a disease in a subject, the method comprising administering to the subject a therapeutically effective amount of the disclosed composition.

The present invention is directed to a method of generating a modified cell comprising a modified endogenous gene, the modified cell having an altered response to a cell signal or stimulus, the method comprising replacing an endogenous gene or fragment thereof with a transgene using a CRISPR/Cas9 system to generate the modified endogenous gene.

The present invention is directed to a method of generating a modified cell comprising a modified endogenous gene comprising a signal peptide, the modified cell having an altered response to a cell signal or stimulus, the method comprising deleting or knocking out the signal peptide using a CRISPR/Cas9 system to generate the modified endogenous gene.

BRIEF DESCRIPTION OF THE DRAWINGS

FIG. 7A shows the double-stranded DNA (dsDNA) content. FIG. 7B shows the sulfated glycosaminoglycan (sGAG) per DNA. FIG. 7C shows the total collagen per DNA. FIG. 7D shows the total sGAG per aggregate. FIG. 7E shows the total collagen per aggregate.

Bars represent group means±SEM (n=6). *p<0.05 between Il1r1+/− and other genotypes. Groups not sharing the same letter are statistically different (p<0.05). FIG. 7F shows the representative images from safranin-O/fast green/hematoxylin staining of 10 μm sections of engineered cartilage treated with or without 1 ng/ml of IL-1 for 72 hours. Scale bar=500 μm.

FIG. 8A shows the specific MMP activity (n=7). RFU indicates relative fluorescence units. FIG. 8B shows the concentration of sGAG measured in culture media (n=6). FIG. 8C shows the PGE2 concentration (n=4). FIG. 8D shows the Total nitric oxide concentrations (n=4). Bars represent group means±SEM. Groups not sharing the same letter are statistically different (p<0.05).

FIG. 9A shows in wild-type (WT) cells, TNF-α signaling through its type 1 receptor initiates a cascade leading to nuclear translocation and increased transcriptional activity of NF-κB, activating an inflammatory transcriptional program. One gene rapidly and highly upregulated by cytokine-induced NF-κB activity is Ccl2 (shown in orange). FIG. 9B shows that a CRISPR/Cas9 RNA-guided nuclease (not depicted) generates a double strand break in the endogenous chromosomal locus near the start codon for Ccl2. Provision of a targeting vector with a transgene flanked by regions homologous to the Ccl2 locus promotes the use of this template for repair of the damaged allele in a subset of cells. FIG. 9C shows that such alleles would then be activated by TNF-α, which would now drive expression of the soluble TNF type 1 receptor (sTNFR1). FIG. 9D shows that upon antagonism of TNF-α in the microenvironment, signal transduction through the membrane receptor would halt, NF-κB would remain sequestered in the cytoplasm, and expression of the sTNFR1 transgene would autonomously decay upon resolution of the local inflammation.

FIG. 14A shows Daily sTNFR1 secretion before and after cytokine stimulation. sTNFR1 levels measured in culture media conditioned for 24 hrs prior to (D0) and after (D1) cytokine treatment. On D1, cytokine was withdrawn from all samples, and media were collected at 24 hr intervals for the subsequent three days. FIG. 14B shows sTNFR1 secretion after iterative cytokine stimulation. Ccl2-sTNFR1 engineered cells were treated with cytokine, and 24 hrs later, media were collected. Cytokine was then withdrawn for 3 days prior to a second and then third stimulation to probe the kinetics of 24-hr sTNFR1 secretion after iterative stimulations. FIG. 14C shows IL1ra secretion after iterative cytokine stimulation. The same experiment as described in FIG. 14B was performed using Ccl2-Il1ra engineered cells, and ELISA was performed on samples to determine protein levels of Il1ra secreted into the culture media. Data labels indicate group average values. Bars represent the mean±SEM (n=3).

DETAILED DESCRIPTION

Figure 1:
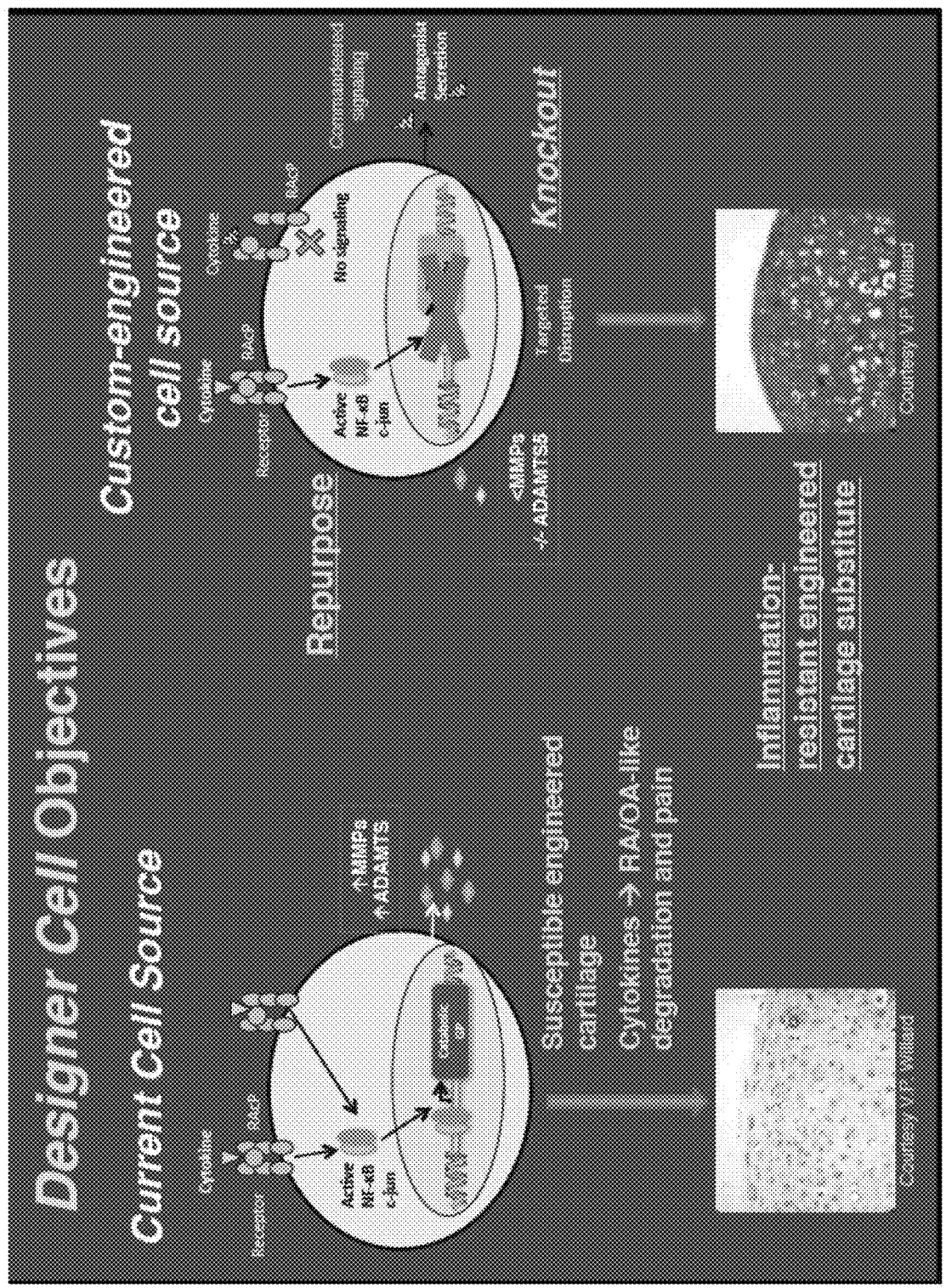
FIG. 1 shows a schematic of designer cell objectives.

The present disclosure provides compositions, systems and methods for cell therapy comprising an engineered or modified cell. In particular, target cells are engineered with gene regulatory factors to enhance the therapeutic effect of various therapies, such as stem cell therapies, for tissue regeneration and treatment of a variety of acute and chronic diseases and cancer. The modified cell may be implanted into tissue and provide self-regulated, feedback control of a therapy, such as anti-cytokine therapy, to the body of a subject. The modified cell may be engineered to delete pathological cell outputs, possess a synthetic input-output gene regulatory system, and/or rewire cells to produce therapeutic molecules in response to pathological signals.

The present disclosure provides an innovative method to rewire cellular gene circuits and created a synthetic transcriptional system in a manner that allows for the creation of unique and customized cells that can sense and respond to their environment in a pre-programmed way, such as dynamically responding to physiological signals. This distinct application of rewiring gene networks in mammalian genomes and cells may control any input-output relationships in cells. The cell's own machinery is reprogrammed to detect subtle, dynamic cues within the body to actively regulate cell response. Using target cells, such as induced pluripotent stem cells, intrinsic signaling pathways may be rewired to virtually "hijack" pathologic signaling cascades (e.g., inflammation) to stimulate controlled therapeutic responses (e.g., anti-inflammatory molecules), thus creating possibilities for safer and more effective treatments for a wide variety of diseases. This self-regulated system could be used in controlling tissue growth or regeneration, mediating tissue repair, or acting as an in situ factory for therapeutic protein delivery. The engineered, self-regulating cells may be used to control the magnitude and duration of biologic therapy for chronic diseases, guide the regeneration of damaged tissues, or produce easily measurable in vivo biomarkers, in which the synthetic transcriptional system can be used to drive expression of reporter molecules.

The compositions and methods that comprise the modified cells, as described herein, provides: (1) Broad applicability—any input and output can be targeted for rewiring; similarly, any therapeutic transgene can be delivered via the synthetic transcriptional system; (2) Specificity—by using gene-editing nucleases, precise modification of the cell's DNA can be performed at a particular site; (3) Flexibility— using cells, such as iPSCs, allow studies to address diseases associated with a variety of other types of tissues or organs.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Cell therapy" as used herein refers to a therapy in which cellular material is injected into a patient. The cellular material may be intact, living cells. For example, T cells capable of fighting cancer cells via cell-mediated immunity may be injected in the course of immunotherapy. Cell therapy is also called cellular therapy or cytotherapy.

"Chronic disease" as used refers to a long-lasting condition that can be controlled but not cured.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Endogenous gene" as used herein refers to a gene that originates from within an organism, tissue, or cell. An endogenous gene is native to a cell, which is in its normal genomic and chromatin context, and which is not heterologous to the cell. Such cellular genes include, e.g., animal genes, plant genes, bacterial genes, protozoal genes, fungal genes, mitochondrial genes, and chloroplastic genes.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance tissue repair by changing the gene of interest.

The term "heterologous" as used herein refers to nucleic acid comprising two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. Similarly, a heterologous protein indicates that the protein comprises two or more subsequences that are not found in the same relationship to each other in nature (e.g., a "fusion protein," where the two subsequences are encoded by a single nucleic acid sequence).

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a CRISPR/Cas9-based systems, then the cellular machinery may repair the break by homologous recombination, which is enhanced several orders of magnitude in the presence of DNA cleavage. When the homologous DNA piece is absent, non-homologous end joining may take place instead.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Immunotherapy" as used herein refers to the treatment of disease by inducing, enhancing, or suppressing an immune response. Immunotherapies designed to elicit or amplify an immune response are classified as activation immunotherapies, while immunotherapies that reduce or suppress are classified as suppression immunotherapies.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Nuclease mediated NHEJ" as used herein refers to NHEJ that is initiated after a nuclease, such as a Cas9, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain. With respect to fusion polypeptides, the terms "operatively linked" and "operably linked" can refer to the fact that each of the components performs the same function in linkage to the other component as it would if it were not so linked.

"Induced pluripotent stem cells" or "iPSCs" as used interchangeably herein refers to a type of pluripotent stem cell that can be artificially derived from a non-pluripotent cell, typically an adult somatic cell, by inducing a "forced" expression of certain genes and transcription factors.

A "progenitor cell" as used herein refers to a biological cell that, like a stem cell, has a tendency to differentiate into a specific type of cell, but is already more specific than a stem cell. While stem cells can replicate indefinitely, progenitor cells can divide only a limited number of times.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

"Site-specific nuclease" as used herein refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), and CRISPR/Cas9-based systems.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be an endogenous gene involved in a disease and/or cellular pathway.

"Target region" as used herein refers to the region of the target gene to which the site-specific nuclease is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Stem cells" as used herein refers to an undifferentiated cell of a multicellular organism that is capable of giving rise to indefinitely more cells of the same type, and from which certain other kinds of cell arise by differentiation. Stem cells can differentiate into specialized cells and can divide (through mitosis) to produce more stem cells. They are found in multicellular organisms. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing adult tissues. In a developing embryo, stem cells can differentiate into all the specialized cells, such as ectoderm, endoderm and mesoderm, but also maintain the normal turnover of regenerative organs, such as blood, skin, or intestinal tissues.

"Suicide gene" as used herein refers to a gene that will cause a cell to kill itself through apoptosis. Activation of these genes may be due to many processes, but the main cellular "switch" to induce apoptosis is the p53 protein. Stimulation or introduction (through gene therapy) of suicide genes may be used to treat cancer or other proliferative diseases by making cancer cells more vulnerable, more sensitive to chemotherapy. Parts of genes expressed in cancer cells are attached to other genes for enzymes not found in mammals that can convert a harmless substance into one that is toxic to the tumor. The suicide genes that mediate this sensitivity may encode for viral or bacterial enzymes that convert an inactive drug into toxic antimetabolites that inhibit the synthesis of nucleic acid.

"T cell" or "T lymphocyte" as used interchangeably herein refers to a cell derived from thymus among lymphocytes involved in an immune response.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid.

2. COMPOSITIONS FOR CELL THERAPY

Provided herein are compositions for use in cell therapy. The compositions include a modified cell having a modified endogenous gene. The modified cells may be engineered or modified ex vivo with engineered transcriptional regulators or other genome engineering tools, such as site specific nucleases, targeted to one or more specific endogenous genes of interest or target genes. The modified cells may have synthetic activators or repressors of genes that control stem cell survival, proliferation, engraftment, migration, homing, and/or response to endogenous inflammatory, immunomodulatory, or morphogenetic signals. For example, stem cells may be reprogrammed through genome engineering for autonomously regulated anti-cytokine therapy. In some embodiments, the modified cells may have a reprogrammed checkpoint inhibitor signaling pathway.

The site-specific nuclease may bind and cleave a target endogenous gene or locus in the genome of a cell. For example, the target endogenous gene or locus may be Ccl2, ADAMTS-5 or IL1r1 gene. The modification may be by delivery of nucleic acids encoding the gene-modifying agent, including viral transduction or transfection of plasmid DNA or mRNA, or by direct treatment with the zinc finger protein, TALE protein, or CRISPR/Cas9 protein:RNA complex. In some embodiments, the CRISPR/Cas9-based system, as described below, may be used to introduce site-specific double strand breaks at targeted genomic loci to modify the endogenous gene. In some embodiments, the coding region of the endogenous gene is replaced with the coding region of a transgene using the CRISPR/Cas9-based system to generate the modified endogenous gene. In some embodiments, the endogenous gene or fragment thereof is deleted or knocked out using the CRISPR/Cas9-based system to generate the modified endogenous gene.

The modified cell may be engineered to delete pathological cell outputs. Functional deficiencies or complete knock-out are generated of the proteins encoded by the targeted endogenous gene in cells, such as stem cells. In some embodiments, the chromosomal loci of genes involved in the inflammatory response of cells are targeted.

The modified cell may be engineered to possess a synthetic input-output gene regulatory system. Synthetic, self-regulating transcriptional system is generated that is activated by a specific input, e.g., inflammatory cytokines, insulin, glucose, etc., or any other cellular feedback system, natural, and artificial. In some embodiments, the synthetic, self-regulating transcriptional system is activated by inflammatory cytokines. Starting with iPSCs, an artificial promoter driving co-expression of luciferase, as well as synthetic transcription factors designed to confer important engineering controls to the system may be engineered. The artificial promoter may include tandem repeats of known binding sites of endogenous transcription factors involved in driving inflammatory transcriptional programs, such as members of the rel/NF-κB family. Moreover, binding sites recognized by the synthetic transcription factors allow fine-tuning of the sensitivity, dynamic range, temporal responsiveness, and memory of the transcriptional control system. A sensitive luciferase-based assay may be used to iteratively tune each of these critical design parameters for optimal performance of the cellular response.

The modified cell may be engineered to rewire cells to produce therapeutic molecules in response to pathological signals. In some embodiments, the therapeutic molecule may be an anti-inflammatory, anti-cytokine, pro-anabolic, or analgesic molecule. For example, the therapeutic molecule may be encoded by a gene whose product affects the inflammatory pathway and/or affects the activity or the pathways of signalling of cytokines.

3. ALTERED RESPONSE TO CELL SIGNAL OR STIMULUS

The modified cell has an altered response to cell signal or stimulus. Using induced pluripotent stem cells, intrinsic signaling pathways may be rewired to virtually "hijack" pathologic signaling cascades, for example, inflammation, to stimulate controlled therapeutic responses, for example, anti-inflammatory molecules, creating possibilities for safer and more effective treatments for a wide variety of diseases. In some embodiments, normal cellular responses may be reprogrammed not only to control the differentiation state of these cells, but also to rewire the genetic circuitry of the cells to define novel input-output relationships.

In some embodiments, the altered response to the cell signal or stimulus may involve the activation of the transgene which activates or downregulates a signaling pathway in response to the cell signal or stimulus as compared to the response to the cell signal or stimulus by the unmodified endogenous gene. For example, the activation of the transcription factor may activate an anti-inflammatory response while the unmodified endogenous gene may activate an inflammatory response. The inflammatory cell signaling network may be either disrupted or reprogrammed in order to generate engineered tissues capable of modulating an effective response against pro-inflammatory cytokines.

In some embodiments, the altered response to the cell signal or stimulus may involve the functional deficiency or complete knock-out of the protein encoded by the target endogenous gene or fragment thereof. The altered response proteins may be a decrease in responsiveness of the modified endogenous gene to the cell signal or stimuli compared to an unmodified endogenous gene.

a) Cell Signal or Stimulus

The compositions may be used to design synthetic, self-regulating transcriptional system that is activated by a specific input, e.g., inflammatory cytokines, insulin, glucose, etc., or any other cellular feedback system, natural, and artificial. For example, the cell signal or stimulus ("the input stimulus") may be any chemical or mechanical signal, such as soluble factors, cell-cell, or cell-matrix interactions; inflammatory stimulus such as stimulation with various concentrations and durations of TNF. Cell signaling that is redirected may be used to rewire the genetic program activated by any stimulus, i.e., physical signals, hormones, growth factors, inflammatory or anti-inflammatory cytokines, transcription factors, etc.

b) Cytokine-Inducible

The modified cells may include a feedback control system for cell-based delivery of inhibitors of tumor necrosis factor alpha (TNF), a pro-inflammatory cytokine that plays a key role in a number of autoimmune disorders, particularly rheumatoid arthritis. Modified cells may be generated that respond directly to harmful inflammatory cues by automatically producing anti-inflammatory molecules to treat autoimmune diseases, such as rheumatoid arthritis. This disease is characterized by painful flares that are mediated by inflammatory cytokines and ultimately lead to destruction of the joint, including the articular cartilage. Current therapies for this disease involve high and unregulated doses of anti-cytokine therapies, which are associated with significant side effects and risks. The development of modified cells may regenerate articular cartilage, while intrinsically protecting against inflammation-mediated degradation.

A promoter of an endogenous gene may be utilized in the modified cells to regulate anti-cytokine therapy in an autonomous, real-time fashion. Features making an endogenous locus a suitable candidate for this endeavor include the following: (1) The co-opted gene must be cytokine-inducible. (2) Basal expression from the endogenous gene must be low to prevent unwanted expression of anti-cytokine therapy. Furthermore, low basal expression is required to permit detection of increased local cytokine levels by engineered cells. (3) Expression kinetics of the gene must be sufficient to generate a rapid response such that the inflammatory program is reversible by production of anti-cytokine therapy. (4) Cytokine-induced gene expression must persist for an adequate period of time to ensure the response is sufficiently robust to combat persistent inflammatory cues. (5) The gene should be induced by a variety of cell types in response to inflammatory cues. (6) Disruption of at least one allele of this gene ought to have no negative consequences on overall cellular function.

For example, pluripotent stem cells may be modified with the prescribed feature of inflammatory cytokine resistance by performing targeted addition of therapeutic transgenes to the cytokine-responsive Ccl2 locus. Transgene expression from engineered cells may be feedback-controlled with rapid on/off dynamics and may be adequate to mitigate the inflammatory effects of physiologic concentrations of both IL-1α and TNF-α in the context of precursor cells cultured in monolayer as well as in engineered tissues such as cartilage.

Modified cells may provide autonomous and dynamically regulated production of therapeutic molecules in response to a pre-programmed biological signal. In some embodiments, mammalian stem cells are modified to provide feedback control for self-regulated delivery of an inhibitor of the pro-inflammatory cytokine, tumor necrosis factor alpha (TNF), as a therapy for rheumatoid arthritis, a progressive autoimmune disease that leads to painful joint destruction and disability. This system is advantageous for being a self-regulating drug delivery system, as anti-TNF therapies are highly effective in many patients but are administered through regular injections at very high doses, increasing susceptibility to infections as well as the risk of cardiovascular disease, hepatitis, and cancer. In this regard, the composition comprising the modified cell may include a drug delivery system that biologically senses TNF levels and responds dynamically with appropriate levels of a TNF inhibitor for the treatment of rheumatoid arthritis and other autoimmune diseases. A tissue implant comprised of the composition of modified cells custom-designed with a precisely engineered, feedback-controlled gene circuit may control production of an anti-inflammatory therapy to rapidly and automatically protect the joint (and the whole body) from TNF-mediated damage.

4. ENDOGENOUS TARGET GENE

The modified cell includes a modified endogenous gene, wherein an endogenous gene or fragment thereof is replaced with a transgene using a CRISPR/Cas9 system to generate the modified endogenous gene that are functional deficiencies or complete knock-out of the proteins coded by the targeted genes in the cells. Endogenous target genes include, but are not limited to, a variety of growth factor, inflammatory mediators, and transcription factors, including but not limited to genes encoding Ccl2, VEGF-A, IL-2, IFN, IL-1Ra, IL-1R2, IL-6, IL-17, IL1r1, telomerase, TNF, IFN, p21, TNFR1, CTLA4, PD-1, certain metalloproteinases (MMPs), such as MMP2, MMP9, and MMP13, ADAMTS, such as aggrecanase (ADAMTS5) and other genes in the inflammatory, pain, or catabolic pathways.

The endogenous target gene may be a gene that is activated by a cytokine, such as TNF. There are three broad groups based on gene induction profiles: class I, II, and III genes (Hao and Baltimore, Nat Immunol. (2009) 10:281-288). Class I genes responded to TNF early, and transcripts decayed quickly irrespective of resolution of the inflammatory assault. Examples of Class I genes include Atf3, Axud1, Btg2, c-Fos, c-Jun, Cxcl1, Cxcl2, Edn1, Ereg, Fos, Gadd45b, Ier2, Ier3, Ifrd1, Il1b, Il6, Irf1, Junb, Lif, Nfkbia, Nfkbiz, Ptgs2, Slc25a25, Sqstm1, Tieg, Tnf, Tnfaip3, and Zfp36. Class II genes responded as late-early mediators and were characterized by a robust response with levels of expression that persisted above baseline only if inflammatory stimuli were also sustained. Upon withdrawal of stimulant, expression of class II genes declined significantly but remained elevated over basal expression. Examples of Class II genes include Birc2, Ccl2, Ccl20, Ccl7, Cebpd, Ch25h, CSF1, Cx3cl1, Cxcl10, Cxcl5, Gch, Icam1, Ifi47, Ifngr2, Mmp10, Nfkbie, Npal1, p21, Relb, Ripk2, Rnd1, S1pr3, Stx11, Tgtp, T1r2, Tmem140, Tnfaip2, Tnfrsf6, and Vcam1. Class III genes were more gradually induced by TNF stimulation and generally continued to accumulate throughout the course of experiments (24 hr), even if TNF was removed. Examples of Class III genes include 1110004C05Rik (GenBank accession number BC010291), Abca1, AI561871 (GenBank accession number BI143915), AI882074 (GenBank accession number BB730912), Arts1, AW049765 (GenBank accession number BC026642.1), C3, Casp4, Ccl5, Ccl9, Cdsn, Enpp2, Gbp2, H2-D1, H2-K, H2-L, Ifit1, Ii, Il13ra1, Il1rl1, Lcn2, Lhfpl2, LOC677168 (GenBank accession number AK019325), Mmp13, Mmp3, Mt2, Naf1, Ppicap, Prnd, Psmb10, Saa3, Serpina3g, Serpinf1, Sod3, Stat1, Tapbp, U90926 (GenBank accession number NM_020562), and Ubd. The modulation of these genes may enhance the angiogenic, immunomodulatory, and proliferative potential of the implanted modified cells.

Biological systems often function reliably in diverse environments despite internal or external perturbations. This behavior is often characterized as "robustness." Much of this robustness can be attributed to the control of gene expression through complex cellular networks. These networks are known to consist of various regulatory modules, including feedback and feed-forward regulation and cell-cell communication. With these basic regulatory modules and motifs, researchers are now constructing artificial networks that mimic nature to gain fundamental biological insight and understanding. In addition, other artificial networks that are engineered with novel functions will serve as building blocks for future practical applications. These efforts form the foundation of the recent emergence of synthetic biology. These artificial networks are interchangeably called "synthetic gene circuits" or "engineered gene circuits." The modified cells may have engineered switches, oscillators logic gates, metabolic control, reengineered translational machinery, population control and pattern formation using natural or synthetic cell-cell communication, reengineered viral genome, and hierarchically complex circuits built upon smaller, well-characterized functional modules. In some embodiments, the target endogenous gene may be any gene that is involved in a complex cellular network.

The endogenous target gene may be gene involved in checkpoint signaling pathway, such as an inhibitory checkpoint molecule. Examples include, but are not limited to, A2AR (Adenosine A2A receptor), B7-H3 (also called CD276), B7-H4 (also called VTCN1), BTLA (B and T Lymphocyte Attenuator; also called CD272), CTLA-4 (Cytotoxic T-Lymphocyte-Associated protein 4; also called CD152), IDO (Indoleamine 2,3-dioxygenase) KIR (Killer-cell Immunoglobulin-like Receptor), LAG3 (Lymphocyte Activation Gene-3), PD-1 (Programmed Death 1 (PD-1) receptor), TIM-3 (T-cell Immunoglobulin domain and Mucin domain 3), and VISTA (V-domain Ig suppressor of T cell activation).

By targeting the transgenes to the start codon of the endogenous target gene, many of the endogenous regulatory features associated with endogenous target gene expression are preserved, including the distal and proximal regulatory regions. As such, the re-purposed endogenous target gene promoter may endow engineered cells with the capacity to substantially upregulate transgene expression in an inducible manner. This upregulation may be both dose- and time-dependent and transient in nature.

(1) Ccl2 or ADAMTS-5

Figure 3:
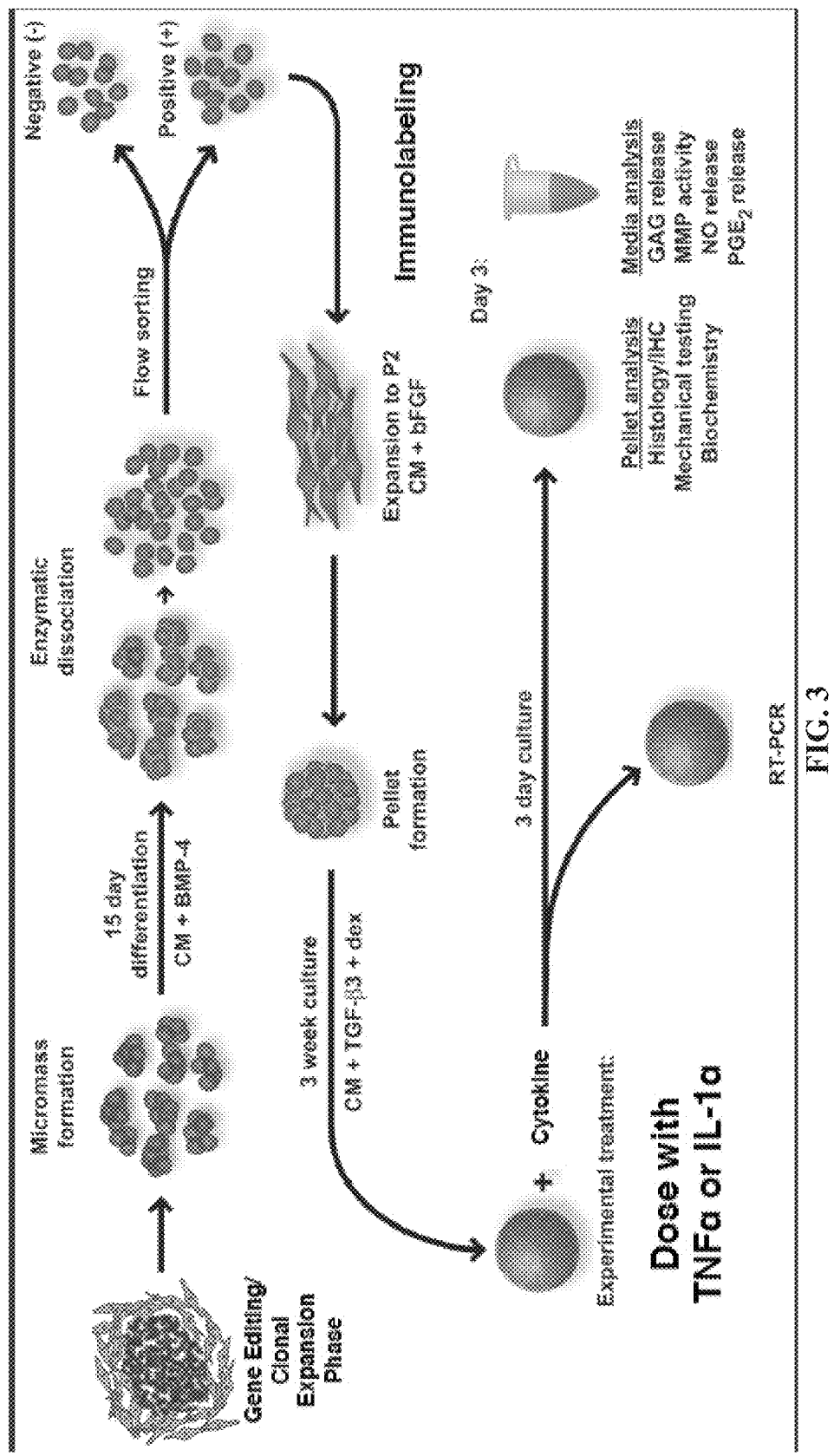
FIG. 3 shows an experimental overview.

The CRISPR/Cas9 system may be used to produce stem cells with programmed responses to inflammatory signaling. In these iPSCs, pro-inflammatory cytokine receptors may be kept intact; however, targeted gene addition to a highly responsive, inflammation-inducible locus may be performed in order to re-purpose a constituent of the inflammatory transcriptional program. An endogenous, inflammation-inducible gene may be co-opted to engineer stem cells capable of auto-regulating the production of biologic therapies that effectively counteract degeneration incited by pro-inflammatory cytokines. In some embodiments, the IL-1- and TNF-regulated chemokine (C-C motif) ligand 2 (Ccl2) gene may be co-opted by replacing the components of the Ccl2 protein coding sequence with that of the cytokine antagonists IL-1 receptor antagonist (Il1ra) or the type I soluble TNF receptor (sTNFR1) (see FIG. 3). In some embodiments, ADAMTS-5 may be co-opted by replacing the components of the ADAMTS-5 protein coding sequence with that of the cytokine antagonists IL-1 receptor antagonist (Il1ra) or the type I soluble TNF receptor (sTNFR1).

Engineered cells may express the endogenous promoter-transgene construct, such as a Ccl2-driven transgene construct, in a cytokine-inducible manner. Cells may autonomously regulate transgene expression in accordance with the degree of inflammation they detected: upon withdrawal of cytokine, Ccl2-driven transgene expression may attenuate the cytokine assault and may lead to decay in expression. Cartilage tissue engineered from these reprogrammed cells may be capable of protecting itself from in vitro treatment of IL-1 and TNF-α that proved sufficient to degrade cartilage generated from control cells.

Ccl2 may be a target locus for controlling transgene expression because of its temporal pattern associated with its cytokine-inducible expression profile. Ccl2 was a gene behaving with rapid induction kinetics similar to group I genes, whereas it displayed an expression profile after the immediate early phase of induction more akin to a group II gene, whose persistence depended on continued exposure to inflammatory cues. By targeting the transgenes to the Ccl2 start codon, many of the endogenous regulatory features associated with Ccl2 expression are preserved, including the distal and proximal regulatory regions encompassing two NF-κB regulatory elements as well as the SP1 and AP-1 binding sites. As such, the re-purposed Ccl2 promoter may endow engineered cells with the capacity to substantially upregulate transgene expression in an inflammation-inducible manner. This upregulation may be both dose- and time-dependent and transient in nature.

In some embodiments, the response of the modified cells may be based on their differentiation status, lineage commitment or cell number. By performing targeted integration to the Ccl2 locus, the transcriptional circuitry associated with inflammatory signaling is rewired in iPSCs. Tissues derived from engineered cells were capable of combating the degenerative effects of cytokine treatment. Genome engineering facilitated the rewiring of endogenous cell circuits in order to define novel input/output relationships between inflammatory mediators and their antagonists, achieving therapeutic benefit coupled to a rapidly responding, auto-regulated system. Gene-edited iPSCs may be differentiated toward the chondrocyte lineage and endowed with the ability to autonomously regulate the production of anti-cytokine therapy at levels adequate to confer tissue-level protection against physiologic and supra-physiologic concentrations of cytokine.

(2) Il1r1

Figure 4:
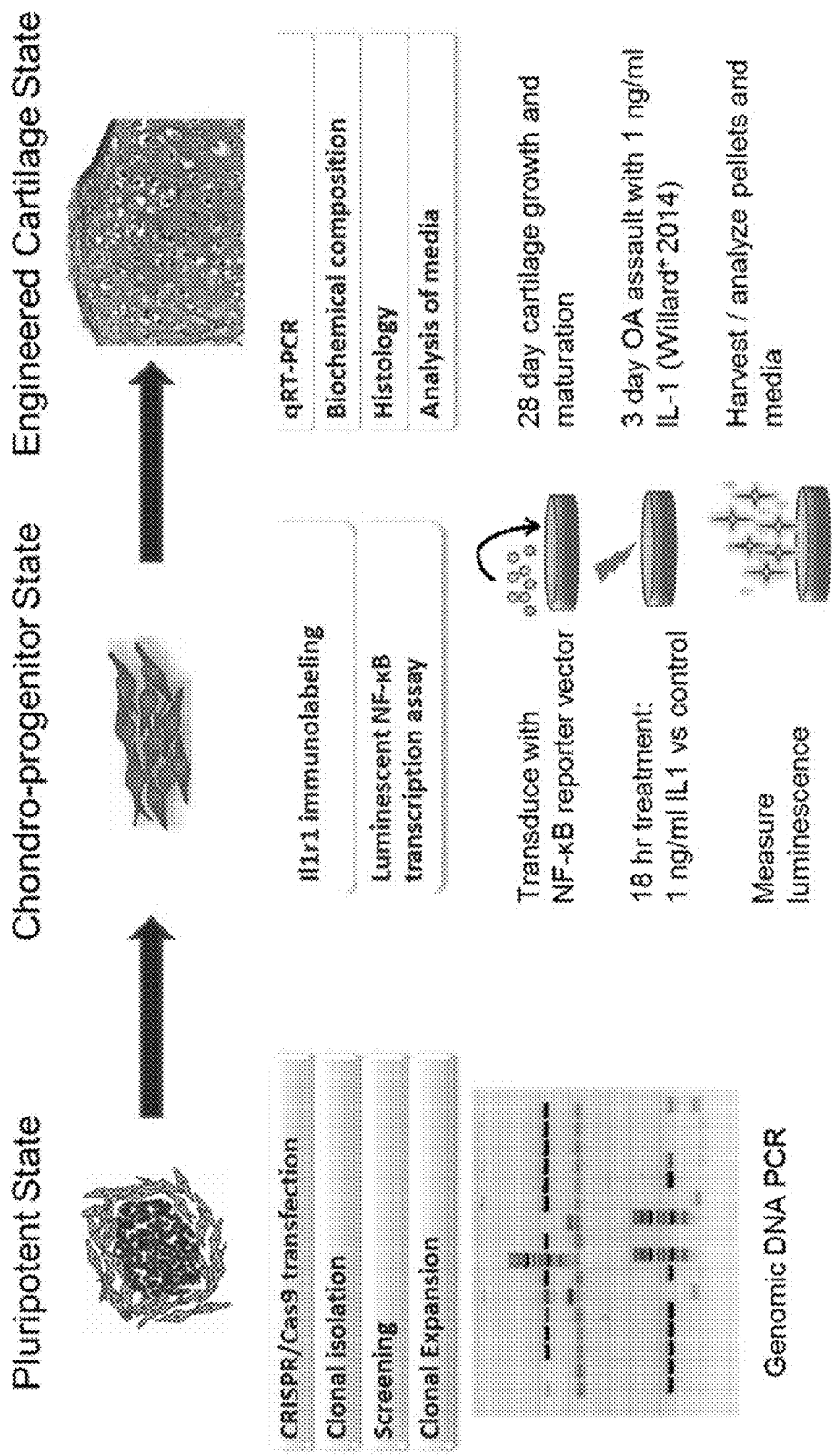
FIG. 4 shows an experimental overview.

Modified cells may have a prescribed feature of resistance to interleukin-1 (IL-1) signaling. The CRISPR/Cas9-based system may include Cas9 and at least one gRNA to target the Il1r1 gene (see FIG. 4). In some embodiments, the target region may be within or in proximity of exon 2 and the IL1r1 gene may be modified by deleting the signal peptide. For example, targeted deletion of the IL-1 type I receptor (Il1r1) signal peptide sequence may be implemented in induced pluripotent stem cells (iPSCs). The cartilage derived from stem cells with targeted disruption of the Il1r1 gene may resist degradation driven by IL-1.

5. TRANSGENES

The modified endogenous gene or fragment thereof may be replaced with a transgene. In some embodiments, the coding region of the endogenous gene is replaced with the coding region of the transgene and the coding region of the transgene is operably linked to the promoter of the endogenous gene. This type of system may integrate multiple biological inputs to various preprogrammed responses by directly targeting transgenes to inducible, endogenous loci using the efficient and highly specific CRISPR/Cas9 genome engineering technology. In this manner, the limitations associated with predicting regulatory features in a genetic locus such as distal enhancers are avoided as the coding region of the endogenous gene is replaced. In addition, this approach abrogates the need to consider limitations on packaging efficiency, as the entire regulatory region need not be packaged in a gene delivery vector. Moreover, by performing targeted integration, this strategy absolves concerns associated with random, uncontrolled insertion of provirus within the host genome. The transgene or output may be a therapeutic growth factor, a transcriptional regulator, an extracellular matrix (ECM) protein, an anti-inflammatory protein, or a biomarker used to monitor treatment efficacy or disease progression. For example, the transgene may be sTNFR1, IL-1Ra, IL6, IkB-alph, IL-10, a suicide gene, or a matrix degrading enzyme, such as a matrix metalloproteinase (MMP).

6. CRISPR SYSTEM

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the sgRNA, and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9: crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The S. pyogenes CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the Streptococcus pyogenes Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from Neisseria meningitidis (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

7. CRISPR/CAS9-BASED SYSTEM

An engineered form of the Type II effector system of Streptococcus pyogenes was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general. Provided herein are CRISPR/Cas9-based engineered systems for use in genome editing. The CRISPR/Cas9-based engineered systems may be designed to target any gene, including genes involved in a genetic disease, aging, tissue regeneration, or wound healing. The CRISPR/Cas9-based systems may include a Cas9 protein or Cas9 fusion protein and at least one gRNA. The Cas9 fusion protein may, for example, include a domain that has a different activity that what is endogenous to Cas9, such as a transactivation domain.

a) Cas9

The CRISPR/Cas9-based system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as Streptococcus pyogenes. The Cas9 protein may be mutated so that the nuclease activity is inactivated. An inactivated Cas9 protein from Streptococcus pyogenes (iCas9, also referred to as "dCas9") with no endonuclease activity has been recently targeted to genes in bacteria, yeast, and human cells by gRNAs to silence gene expression through steric hindrance. As used herein, "iCas9" and "dCas9" both refer to a Cas9 protein that has the amino acid substitutions D10A and H840A and has its nuclease activity inactivated.

b) Cas9 Fusion Protein

The CRISPR/Cas9-based system may include a fusion protein. The fusion protein may comprise two heterologous polypeptide domains, wherein the first polypeptide domain comprises a Cas protein and the second polypeptide domain has nuclease activity that is different from the nuclease activity of the Cas9 protein. The fusion protein may include a Cas9 protein or a mutated Cas9 protein, as described above, fused to a second polypeptide domain that has nuclease activity. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

c) gRNA

The gRNA provides the targeting of the CRISPR/Cas9-based system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA: tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The "target region", "target sequence" or "protospacer" as used interchangeably herein refers to the region of the target gene to which the CRISPR/Cas9-based system targets. The CRISPR/Cas9-based system may include at least one gRNA, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide.

The gRNA may target any nucleic acid sequence such as an endogenous gene, as discussed above. The CRISPR/Cas9-based system may use gRNA of varying sequences and lengths. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

The gRNA may comprise a complementary polynucleotide sequence of the target DNA sequence followed by a PAM sequence. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The PAM sequence may be "NGG", where "N" can be any nucleotide. The gRNA may target at least one of the promoter region, the enhancer region or the transcribed region of the target gene. The gRNA may include a nucleic acid sequence of at least one of SEQ ID NOs: sgRNA_Il1r1-4: GCTTCTGTGTTGAAGACTCA (SEQ ID NO: 45), sgRNA_Il1r1-6: GTAGCTGTGGGCCCACAACC (SEQ ID NO: 46), sgRNA_Ccl2-4: GCTCTTCCTCCACCAC-CATGC (SEQ ID NO: 47).

8. MULTIPLEX CRISPR/CAS9-BASED SYSTEM

A multiplex CRISPR/Cas9-Based System which includes a CRISPR/CRISPR-associated (Cas) 9-based system, such as Cas9 or dCas9, and multiple gRNAs may be used to target one or more endogenous genes. This platform utilizes a convenient Golden Gate cloning method to rapidly incorporate up to four independent sgRNA expression cassettes into a single lentiviral vector. In some embodiments, the platform is incorporated into adeno-associated virus vectors or an integrase-deficient lentivirus vector. Each sgRNA was efficiently expressed and could mediate multiplex gene editing at diverse loci in immortalized and primary human cell lines.

The multiplex CRISPR/Cas9-Based System allows efficient multiplex gene editing for simultaneously inactivating multiple genes. The CRISPR/Cas9 system can simultaneously target multiple distinct genomic loci by co-expressing a single Cas9 protein with two or more sgRNAs, making this system uniquely suited for multiplex gene editing or synergistic activation applications. The CRISPR/Cas9 system greatly expedites the process of molecular targeting to new sites by simply modifying the expressed sgRNA molecule. The single lentiviral vector may be combined with methods for achieving inducible control of these components, either by chemical or optogenetic regulation, to facilitate investigation of the dynamics of gene regulation in both time and space.

a) Modified Lentiviral Vector

The multiplex CRISPR/Cas9-based system includes a modified lentiviral vector. The modified lentiviral vector includes a first polynucleotide sequence encoding a Cas9 fusion protein and a second polynucleotide sequence encoding at least one sgRNA. The first polynucleotide sequence may be operably linked to a promoter. The promoter may be a constitutive promoter, an inducible promoter, a repressible promoter, or a regulatable promoter.

The second polynucleotide sequence encodes at least 1 sgRNA. For example, the second polynucleotide sequence may encode at least 1 sgRNA, at least 2 sgRNAs, at least 3 sgRNAs, at least 4 sgRNAs, at least 5 sgRNAs, at least 6 sgRNAs, at least 7 sgRNAs, at least 8 sgRNAs, at least 9 sgRNAs, at least 10 sgRNAs, at least 11 sgRNA, at least 12 sgRNAs, at least 13 sgRNAs, at least 14 sgRNAs, at least 15 sgRNAs, at least 16 sgRNAs, at least 17 sgRNAs, at least 18 sgRNAs, at least 19 sgRNAs, at least 20 sgRNAs, at least 25 sgRNA, at least 30 sgRNAs, at least 35 sgRNAs, at least 40 sgRNAs, at least 45 sgRNAs, or at least 50 sgRNAs. The second polynucleotide sequence may encode between 1 sgRNA and 50 sgRNAs, between 1 sgRNA and 45 sgRNAs, between 1 sgRNA and 40 sgRNAs, between 1 sgRNA and 35 sgRNAs, between 1 sgRNA and 30 sgRNAs, between 1 sgRNA and 25 different sgRNAs, between 1 sgRNA and 20 sgRNAs, between 1 sgRNA and 16 sgRNAs, between 1 sgRNA and 8 different sgRNAs, between 4 different sgRNAs and 50 different sgRNAs, between 4 different sgRNAs and 45 different sgRNAs, between 4 different sgRNAs and 40 different sgRNAs, between 4 different sgRNAs and 35 different sgRNAs, between 4 different sgRNAs and 30 different sgRNAs, between 4 different sgRNAs and 25 different sgRNAs, between 4 different sgRNAs and 20 different sgRNAs, between 4 different sgRNAs and 16 different sgRNAs, between 4 different sgRNAs and 8 different sgRNAs, between 8 different sgRNAs and 50 different sgRNAs, between 8 different sgRNAs and 45 different sgRNAs, between 8 different sgRNAs and 40 different sgRNAs, between 8 different sgRNAs and 35 different sgRNAs, between 8 different sgRNAs and 30 different sgRNAs, between 8 different sgRNAs and 25 different sgRNAs, between 8 different sgRNAs and 20 different sgRNAs, between 8 different sgRNAs and 16 different sgRNAs, between 16 different sgRNAs and 50 different sgRNAs, between 16 different sgRNAs and 45 different sgRNAs, between 16 different sgRNAs and 40 different sgRNAs, between 16 different sgRNAs and 35 different sgRNAs, between 16 different sgRNAs and 30 different sgRNAs, between 16 different sgRNAs and 25 different sgRNAs, or between 16 different sgRNAs and 20 different sgRNAs. Each of the polynucleotide sequences encoding the different sgRNAs may be operably linked to a promoter. The promoters that are operably linked to the different sgRNAs may be the same promoter. The promoters that are operably linked to the different sgRNAs may be different promoters. The promoter may be a constitutive promoter, an inducible promoter, a repressible promoter, or a regulatable promoter.

At least one sgRNA may bind to a target gene or loci. If more than one sgRNA is included, each of the sgRNAs binds to a different target region within one target loci or each of the sgRNA binds to a different target region within different gene loci. The fusion protein may include Cas9 protein or iCas9-VP64 protein. The fusion protein may include a VP64 domain, a p300 domain, or a KRAB domain.

b) Adeno-Associated Virus Vectors

AAV may be used to deliver CRISPRs to the cell using various construct configurations. For example, AAV may deliver Cas9 and gRNA expression cassettes on separate vectors. Alternatively, if the small Cas9 proteins, derived from species such as *Staphylococcus aureus* or *Neisseria meningitidis*, are used then both the Cas9 and up to two gRNA expression cassettes may be combined in a single AAV vector within the 4.7 kb packaging limit.

The composition, as described above, includes a modified adeno-associated virus (AAV) vector. The modified AAV vector may be capable of delivering and expressing the site-specific nuclease in the cell of a mammal. For example, the modified AAV vector may be an AAV-SASTG vector (Piacentino et al. (2012) Human Gene Therapy 23:635-646). The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

9. METHODS OF GENERATING THE MODIFIED CELL

Also provided herein is a method of generating the modified cell. The method comprises administering a CRISPR/Cas 9 system to the target cell, as described above. Use of the CRISPR/Cas 9 system to deliver the site-specific nuclease to the cell may delete or replace the endogenous gene or fragment thereof thus generating the modified endogenous gene. The site-specific nuclease may be used to introduce site-specific double strand breaks at targeted genomic loci. Site-specific double-strand breaks are created when the site-specific nuclease binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to generating the modified cell with a site-specific nuclease without a repair template. The disclosed site-specific nucleases may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active site-specific nucleases with an efficient gene editing method for generating the modified cell. The method may involve homology-directed repair or non-homologous end joining.

10. METHODS OF TREATING A DISEASE

The present disclosure is directed to a method of treating a subject in need thereof. The method comprises administering to subject the composition for cell therapy, as described above. The subject may have diseases include a variety of acute and chronic diseases including but not limited to genetic, degenerative, or autoimmune diseases and obesity related conditions. Diseases include acute and chronic immune and autoimmune pathologies, such as, but not limited to, rheumatoid arthritis (RA), juvenile chronic arthritis (JCA), tissue ischemia, thyroiditis, graft versus host disease (GVHD), scleroderma, diabetes mellitus, Graves' disease, disc degeneration and low back pain, allergy, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation; infections, including, but not limited to, sepsis syndrome, cachexia, circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) (including symptoms of cachexia, autoimmune disorders, AIDS dementia complex and infections); inflammatory diseases, such as chronic inflammatory pathologies, including chronic inflammatory pathologies such as, but not limited to, sarcoidosis, chronic inflammatory bowel disease, ulcerative colitis, osteogenesis imperfecta, and Crohn's pathology or disease; vascular inflammatory pathologies, such as, but not limited to, disseminated intravascular coagulation, atherosclerosis, Kawasaki's pathology and vasculitis syndromes, such as, but not limited to, polyarteritis *nodosa*, Wegener's granulomatosis, Henoch-Schonlein purpura, giant cell arthritis and microscopic vasculitis of the kidneys; chronic active hepatitis; Sjogren's syndrome; spondyloarthropathies, such as ankylosing spondylitis, psoriatic arthritis and spondylitis, enteropathic arthritis and spondylitis, reactive arthritis and arthritis associated with inflammatory bowel disease; and uveitis; neurodegenerative diseases, including, but not limited to, demyelinating diseases, such as multiple sclerosis and acute transverse myelitis; myasthenia gravis; extrapyramidal and cerebellar disorders, such as lesions of the corticospinal system; disorders of the basal ganglia or cerebellar disorders; hyperkinetic movement disorders, such as Huntington's chorea and senile chorea; drug-induced movement disorders, such as those induced by drugs which block central nervous system (CNS) dopamine receptors; hypokinetic movement disorders, such as Parkinson's disease; progressive supranuclear palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoprotienemia, ataxia, telangiectasia, and mitochondrial multisystem disorder); disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's syndrome in middle age; diffuse Lewy body disease; senile dementia of Lewy body type; Wernicke-Korsakoff syndrome; chronic alcoholism; primary biliary cirrhosis; cryptogenic fibrosing alveolitis and other fibrotic lung diseases; hemolytic anemia; Creutzfeldt-Jakob disease; subacute sclerosing panencephalitis, Hallervorden-Spatz disease; and dementia pugilistica, or any subset thereof; and malignant pathologies involving TNF-secreting tumors or other malignancies involving TNF, such as, but not limited to, leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)).

i) Chronic inflammatory Disease

Chronic inflammatory diseases such as arthritis are characterized by aberrant activity of cytokines such as tumor necrosis factor-α (TNF-α) and interleukin-1 (IL-1). These pro-inflammatory mediators are expressed by a wide variety of cells in musculoskeletal tissues, including myotubes, satellite cells, chondrocytes, synovial fibroblasts, osteoblasts, and resident as well as infiltrating innate immune cells. These cell types are also capable of responding to TNF-α and IL-1α through canonical signaling via their cognate cell surface receptors. In healthy tissue, appropriate signaling of TNF-α and IL-1 contributes to organ and tissue homeostasis. In this state, these mediators promote tissue remodeling, orchestrate phagocytosis of cellular debris and immunogenic substrates, and coordinate transitions between niche stem cell quiescence and proliferation/differentiation programs. TNF-α has also been shown to enhance stem cell differentiation in a variety of efforts to enhance MSC osteogenesis. However, in chronic diseases, elevated levels of these pro-inflammatory cytokines can lead directly to pain, cytotoxicity, accelerated tissue catabolism or wasting, and exhaustion of resident stem cell niches.

A regenerative medicine approach may be used to treat chronic inflammatory diseases by generating custom-designed cells that can execute real-time, programmed responses to environmental cues, including pro-inflammatory cytokines. Modified cells, such as stem cells, may be generated with the ability to antagonize IL-1- and TNFα-mediated inflammation in an auto-regulated, feedback-controlled manner. Targeted gene addition of IL-1 and TNF antagonists may be performed at the Ccl2 locus to confer cytokine-activated and feedback-controlled expression of biologic therapies. Genome-edited stem cells may be used to engineer articular cartilage tissue to establish the efficacy of self-regulated therapy toward protection of tissues against cytokine-induced degeneration. This approach of repurposing normally degradative signaling pathways may facilitate transient production of cytokine antagonists and permit effective treatment of chronic diseases while overcoming limitations associated with delivery of large drug doses or constitutive overexpression of biologic compounds.

A therapeutic molecule may be any number of exogenous anti-cytokine therapies that effectively counteract the negative sequelae of TNF-α and IL-1 dysregulation. For example, therapeutic molecules may include competitive antagonists such as IL-1 receptor antagonist (IL-1Ra, anakinra), which alleviate symptoms of rheumatoid arthritis and the onset of post-traumatic arthritis; anti-TNF therapies, such as the soluble type 2 TNF receptor (etanercept) and monoclonal antibodies to TNF-α (adalimumab, infliximab), which have demonstrated efficacy toward offsetting pain associated with chronic and rheumatic diseases, including arthritis, ankylosing spondylitis, Crohn disease, plaque psoriasis, and ulcerative colitis; type I soluble TNFR receptor (sTNFR1), which generally provided in the context of relatively high or unregulated doses.

11. METHODS OF CANCER THERAPY

The compositions may be used in methods of cancer therapy where the immune system is used to treat cancer. Immunotherapies fall into three main groups: cellular, antibody and cytokine. They exploit the fact that cancer cells often have subtly different molecules on their surface that can be detected by the immune system. These molecules, known as cancer antigens, are most commonly proteins, but also include molecules such as carbohydrates. Immunotherapy is used to provoke the immune system into attacking the tumor cells by using these antigens as targets.

The compositions may be used in cellular therapies, also known as cancer vaccines, usually involve the removal of immune cells from the blood or from a tumor. Immune cells specific for the tumor may be modified, cultured and returned to the patient where the immune cells attack the cancer. Cell types that can be used in this way are natural killer cells, lymphokine-activated killer cells, cytotoxic T cells and dendritic cells.

Interleukin-2 and interferon-α are examples of cytokines, proteins that regulate and coordinate the behavior of the immune system. They have the ability to enhance anti-tumor activity and thus can be used as cancer treatments. Interferon-α is used in the treatment of hairy-cell leukemia, AIDS-related Kaposi's sarcoma, follicular lymphoma, chronic myeloid leukemia and malignant melanoma. Interleukin-2 is used in the treatment of malignant melanoma and renal cell carcinoma.

Dendritic cell therapy provokes anti-tumor responses by causing dendritic cells to present tumor antigens. Dendritic cells present antigens to lymphocytes, which activates them, priming them to kill other cells that present the antigen. In cancer treatment they aid cancer antigen targeting. One method of inducing dendritic cells to present tumor antigens is by vaccination with short peptides (small parts of protein that correspond to the protein antigens on cancer cells). These peptides on their own do not stimulate a strong immune response and may be given in combination with adjuvants (highly immunogenic substances). This provokes a strong response, while also producing a (sometimes) robust anti-tumor response by the immune system. Other adjuvants include proteins or other chemicals that attract and/or activate dendritic cells, such as granulocyte macrophage colony-stimulating factor (GM-CSF). Dendritic cells can also be activated within the body (in vivo) by making tumor cells express (GM-CSF). This can be achieved by either genetically engineering tumor cells that produce GM-CSF or by infecting tumor cells with an oncolytic virus that expresses GM-CSF.

Another strategy is to remove dendritic cells from the blood of a patient and activate them outside the body (ex vivo). The dendritic cells are activated in the presence of tumor antigens, which may be a single tumor-specific peptide/protein or a tumor cell lysate (a solution of broken down tumor cells). These activated dendritic cells are put back into the body where they provoke an immune response to the cancer cells. Adjuvants are sometimes used systemically to increase the anti-tumor response provided by ex vivo activated dendritic cells. More modern dendritic cell therapies include the use of antibodies that bind to receptors on the surface of dendritic cells. Antigens can be added to the antibody and can induce the dendritic cells to mature and provide immunity to the tumor. Dendritic cell receptors such as TLR3, TLR7, TLR8 or CD40 have been used as targets by antibodies to produce immune responses.

Cytokines are a broad group of proteins produced by many types of cells present within a tumor. They have the ability to modulate immune responses. The tumor often employs it to allow it to grow and manipulate the immune response. These immune-modulating effects allow them to be used as drugs to provoke an immune response. Two commonly used groups of cytokines are interferons and interleukins.

Interferons are cytokines produced by the immune system. They are usually involved in anti-viral response, but also have use for cancer. The three groups of interferons (IFNs) are type I (IFNα and IFNβ), type II (IFNγ) and type III (IFNλ). IFNα has been approved for use in hairy-cell leukemia, AIDS-related Kaposi's sarcoma, follicular lymphoma, chronic myeloid leukemia and melanoma. Type I and II IFNs have been researched extensively and although both types promote anti-tumor immune system effects, only type I IFNs have been shown to be clinically effective. IFNλ shows promise for its anti-tumor effects in animal models.

Interleukins are a group of cytokines with a wide array of immune system effects. Interleukin-2 is used in the treatment of malignant melanoma and renal cell carcinoma. In normal physiology it promotes both effector T cells and T-regulatory cells, but its exact mechanism in the treatment of cancer is unknown.

12. METHODS OF REGENERATIVE THERAPY USING CELL THERAPY

Regenerative medicine provides the exciting potential for cell-based therapies to treat many diseases and restore damaged tissues using engineered cells for musculoskeletal applications. Modified cells derived from a myriad of adult tissues and differentiated down a lineage of choice may be tailored at the scale of the genome with application-dependent features. The compositions described here have broad applicability in regenerative medicine. For example, the ability to immobilize gene delivery vehicles capable of dictating cell fate and orchestrating ECM deposition may allow future investigators to control the spatial patterning of tissue development. This approach could indeed be applied toward engineering tissues comprised of multiple cell types and organized into regions of varied and distinct ECM constituents, a persistent challenge in the field of orthopaedic tissue engineering. Furthermore, diseases may be treated that involve complex interactions between multiple organ systems, those that drive deterioration of tissues that are not amenable to total replacement, or those in which discrimination between pathologic and healthy tissue/cells may be subtle or require real-time determination for safe and effective alleviation of disease. Such conditions may be most efficiently addressed by cells that can infiltrate, intelligently detect dysfunction, and deploy predefined therapeutic programs to resolve anomalous behavior of endogenous cells or ECM disorganization/degeneration. Employing these and other tools from synthetic biology together under the auspices of a functional cellular and tissue engineering paradigm, which aims to fully characterize and recapitulate features critical for successful cell/tissue replacement, will likely serve to advance the field of regenerative medicine toward the establishment of clinically effective therapies for a host of diseases.

In some embodiments, the site-specific nucleases may be used to generate functional deficiencies or complete knockout of the proteins coded by the targeted genes in human iPSCs. Genetically modified iPSCs may be differentiated into chondrocytes using established techniques. Feedback-controlled gene circuits may be designed to modulate the production of soluble TNF receptors—specifically soluble TNF receptor 1 (sTNFR1), which blocks TNF signaling—in response to dynamic TNF levels. In some embodiments, this process may be performed in induced pluripotent stem cells (iPSCs), which can be expanded indefinitely, thus facilitating the complex genetic manipulations required for genome editing. To produce an implant with long-term in vivo stability, the rewired iPSCs may be differentiated into cartilage cells (chondrocytes), a robust, non-migratory cell that naturally responds to TNF. These cells may be formed into a tissue-engineered cartilage implant (see FIG. 1) that can be implanted in the joint to repair damaged cartilage or subcutaneously to provide self-regulated, systemic anti-TNF.

a) Osteoarthritis

The modified cells may be used in musculoskeletal regenerative medicine applications, such as developing therapies for osteoarthritis. Osteoarthritis (OA) is a progressive disease of synovial joints characterized by the destruction of articular cartilage. Surgical treatment options for focal cartilage defects include arthroscopic debridement, marrow stimulation via microfracture, and autologous transplantation of host tissue or ex vivo expanded autologous chondrocytes. Most of these surgical options lead to the development of a fibrocartilage matrix that serves only as a temporary solution to a complex and demanding biomechanical problem. For larger defects, joint arthroplasty serves as the most promising treatment option. While effective at restoring function to the joint, the need to revise an increasing number of primary arthroplasties means that a more functional, long-term solution is needed.

Inflammation plays a key role in the pathogenesis and progression of osteoarthritis (OA) and may compromise engineered tissue substitutes. Chondrocytes and synovial fibroblasts in OA joints are subjected to increased interleukin (IL)-1, IL-6, IL-17 and tumor necrosis factor (TNF)-α signaling. The activity of these cytokines in OA joints leads to increased production of matrix metalloproteinases (MMPs), aggrecanases, inducible nitric oxide synthase, and prostaglandin E2. These and other factors ultimately lead to suppression of cartilage-specific genes such as COL2A1, downregulation of proteoglycan levels, degeneration of extracellular matrix, and chondrocyte apoptosis. Furthermore, prolonged inflammatory signaling mediated by IL-1α inhibits chondrogenic induction of stem cells and results in degradation of stem cell derived cartilage. The pro-inflammatory environment of the OA joint therefore necessitates a tissue substitute designed to resist inflammation-mediated degradation.

13. TARGET CELLS

The target cells that are used to generate the modified cells may be stem cells, such as embryonic stem cells (ES) and adult stem cells (somatic stem cells or tissue-specific stem cells), induced pluripotent stem cells (iPSCs), progenitor cells, fibroblasts, cardiomyocytes, hepatocytes, chondrocytes, smooth muscle cells, K562 human erythroid leukemia cell line, bone cells, synovial cells, tendon cells, ligament cells, meniscus cells, adipose cells, B-cells, dendritic cells, natural killer cells, or T-cells.

a) Embryonic Stem Cells (ES)

(ES) cells are isolated from the inner cell mass of blastocysts of preimplantation-stage embryos. These cells require specific signals to differentiate to the desired cell type; if simply injected directly, they will differentiate into many different types of cells, resulting in a tumor derived from this abnormal pluripotent cell development (a teratoma). The directed differentiation of ES cells and avoidance of transplant rejection are just two of the hurdles that ES cell researchers still face. With their potential for unlimited expansion and pluripotency, ES cells are a potential source for regenerative medicine and tissue replacement after injury or disease.

b) Adult Stem Cells

Adult stem cells are undifferentiated cells, found throughout the body after development, that multiply by cell division to replenish dying cells and regenerate damaged tissues. Also known as somatic stem cells, they can be found in juvenile as well as adult animals and human bodies. Scientific interest in adult stem cells is centered on their ability to divide or self-renew indefinitely, and generate all the cell types of the organ from which they originate, potentially regenerating the entire organ from a few cells. Unlike embryonic stem cells, the use of human adult stem cells in research and therapy is not considered to be controversial, as they are derived from adult tissue samples rather than human 5 day old embryos generated by IVF (in vitro fertility) clinics designated for scientific research. They have mainly been studied in humans and model organisms such as mice and rat The production of adult stem cells does not require the destruction of an embryo. Additionally, when adult stem cells are obtained from the intended recipient (an autograft) there is no risk of immune rejection. Adult stem cell treatments have been successfully used for many years to treat leukemia and related bone/blood cancers through bone marrow transplants.

i) Hematopoietic Stem Cells

Hematopoietic stem cells are found in the bone marrow and umbilical cord blood and give rise to all the blood cell types.

ii) Mesenchymal Stem Cells (MSCs)

Mesenchymal stem cells (MSCs) are of stromal origin and may differentiate into a variety of tissues and cell types, including: osteoblasts (bone cells), chondrocytes (cartilage cells), myocytes (muscle cells) adipocytes (fat cells). MSCs have been isolated from placenta, adipose tissue, lung, bone marrow and blood, Wharton's jelly from the umbilical cord and teeth (perivascular niche of dental pulp and periodontal ligament). MSCs are attractive for clinical therapy due to their ability to differentiate, provide trophic support, and modulate innate immune response.

iii) Endothelial Stem Cells

Endothelial stem cells are one of the three types of multipotent stem cells found in the bone marrow. They are a rare and controversial group with the ability to differentiate into endothelial cells, the cells that line blood vessels.

iv) Epithelial Stem Cells

Self-renewing tissues, such as the epidermis and hair follicle, continuously generate new cells to replenish the dead squames and hairs, which are sloughed into the environment. Therefore, perhaps the simplest definition of an epithelial stem cell is based on lineage: a stem cell is the cell of origin for terminally differentiated cells in adult tissues. For example, tracing the lineage of a corneocyte or hair cell back to its ultimate source in the adult skin leads to a stem cell. However, because the tools required to perform lineage analysis have not been available until recently, investigators have principally adopted definitions from the hematopoietic system. In particular, stem cells were felt to be self-renewing, multipotent, and clonogenic, similar to stem cells in the hematopoietic system that can regenerate all of the blood lineages from one cell after transplantation. In contrast to the hematopoietic stem cell field, cutaneous epithelial stem cell biologists also relied heavily on quiescence as a major stem cell characteristic.

v) Neural Stem Cells

The existence of stem cells in the adult brain has been postulated following the discovery that the process of neurogenesis, the birth of new neurons, continues into adulthood in rats. The presence of stem cells in the mature primate brain was first reported in 1967. It has since been shown that new neurons are generated in adult mice, songbirds and primates, including humans. Normally, adult neurogenesis is restricted to two areas of the brain—the subventricular zone, which lines the lateral ventricles, and the dentate gyrus of the hippocampal formation. Although the generation of new neurons in the hippocampus is well established, the presence of true self-renewing stem cells there has been debated. Under certain circumstances, such as following tissue damage in ischemia, neurogenesis can be induced in other brain regions, including the neocortex.

Neural stem cells are commonly cultured in vitro as so called neurospheres—floating heterogeneous aggregates of cells, containing a large proportion of stem cells. They can be propagated for extended periods of time and differentiated into both neuronal and glia cells, and therefore behave as stem cells. However, some recent studies suggest that this behavior is induced by the culture conditions in progenitor cells, the progeny of stem cell division that normally undergo a strictly limited number of replication cycles in vivo. Furthermore, neurosphere-derived cells do not behave as stem cells when transplanted back into the brain.

Neural stem cells share many properties with hematopoietic stem cells (HSCs). Remarkably, when injected into the blood, neurosphere-derived cells differentiate into various cell types of the immune system.

vi) Mammary Stem Cells

Mammary stem cells provide the source of cells for growth of the mammary gland during puberty and gestation and play an important role in carcinogenesis of the breast. Mammary stem cells have been isolated from human and mouse tissue as well as from cell lines derived from the mammary gland. Single such cells can give rise to both the luminal and myoepithelial cell types of the gland, and have been shown to have the ability to regenerate the entire organ in mice.

vii) Intestinal Stem Cells

Intestinal stem cells divide continuously throughout life and use a complex genetic program to produce the cells lining the surface of the small and large intestines. Intestinal stem cells reside near the base of the stem cell niche, called the crypts of Lieberkuhn. Intestinal stem cells are probably the source of most cancers of the small intestine and colon.

viii) Olfactory Adult Stem Cells

Olfactory adult stem cells have been successfully harvested from the human olfactory mucosa cells, which are found in the lining of the nose and are involved in the sense of smell. If they are given the right chemical environment these cells have the same ability as embryonic stem cells to develop into many different cell types. Olfactory stem cells hold the potential for therapeutic applications and, in contrast to neural stem cells, can be harvested with ease without harm to the patient. This means they can be easily obtained from all individuals, including older patients who might be most in need of stem cell therapies.

ix) Neural Crest Stem Cells

Hair follicles contain two types of stem cells, one of which appears to represent a remnant of the stem cells of the embryonic neural crest. Similar cells have been found in the gastrointestinal tract, sciatic nerve, cardiac outflow tract and spinal and sympathetic ganglia. These cells can generate neurons, Schwann cells, myofibroblast, chondrocytes and melanocytes.

x) Testicular Cells

Multipotent stem cells with a claimed equivalency to embryonic stem cells have been derived from spermatogonial progenitor cells found in the testicles of laboratory mice. The extracted stem cells are known as human adult germline biggmacc stem cells (GSCs). Multipotent stem cells have also been derived from germ cells found in human testicles.

c) Induced Stem Cells

Induced stem cells (iSC) are stem cells artificially derived from somatic, reproductive, pluripotent or other cell types by deliberate epigenetic reprogramming. They are classified as totipotent (iTC), pluripotent (iPSC) or progenitor (multipotent-iMSC, also called an induced multipotent progenitor cell-iMPC) or unipotent (iUSC) according to their developmental potential and degree of dedifferentiation.

iPSCs are somatic cells that have been genetically reprogrammed to an embryonic stem cell—like state by being forced to express genes important for maintaining the defining properties of embryonic stem cells. Although additional research is needed, iPSCs are already useful tools for drug development and modeling of diseases, and scientists hope to use them in transplantation medicine. In addition, tissues derived from iPSCs will be a nearly identical match to the cell donor and thus probably avoid rejection by the immune system. By studying iPSCs and other types of pluripotent stem cells, researchers may learn how to reprogram cells to repair damaged tissues in the human body.

xi) Lung and Airway Epithelial Cells

Chronic lung diseases such as idiopathic pulmonary fibrosis and cystic fibrosis or chronic obstructive pulmonary disease and asthma are leading causes of morbidity and mortality worldwide with a considerable human, societal, and financial burden. Several protocols have been developed for generation of the most cell types of the respiratory system, which may be useful for deriving patient-specific therapeutic cells.

xii) Reproductive Cells

Some lines of iPSCs have the potentiality to differentiate into male germ cells and oocyte-like cells in an appropriate niche (by culturing in retinoic acid and porcine follicular fluid differentiation medium or seminiferous tubule transplantation). Moreover, iPSC transplantation make a contribution to repairing the testis of infertile mice, demonstrating the potentiality of gamete derivation from iPSCs in vivo and in vitro d) T-Cells T cells are a type of lymphocyte (in turn, a type of white blood cell) that play a central role in cell-mediated immunity. They can be distinguished from other lymphocytes, such as B cells and natural killer cells (NK cells), by the presence of a T-cell receptor (TCR) on the cell surface. They are called T cells because they mature in the thymus (although some also mature in the tonsils). The several subsets of T cells each have a distinct function. The majority of human T cells rearranges their alpha/beta T cell receptors and are termed alpha beta T cells and are part of adaptive immune system. Specialized gamma delta T cells, which comprise a minority of T cells in the human body (more frequent in ruminants), have invariant TCR (with limited diversity), can effectively present antigens to other T cells and are considered to be part of the innate immune system.

The T cell includes any of a CD8-positive T cell (cytotoxic T cell: CTL), a CD4-positive T cell (helper T cell), a suppressor T cell, a regulatory T cell such as a controlling T cell, an effector cell, a naive T cell, a memory T cell, an αβT cell expressing TCR α and β chains, and a γδT cell expressing TCR γ and δ chains. The T cell includes a precursor cell of a T cell in which differentiation into a T cell is directed. Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids. Further, a variety of cell populations containing T cells and derived from hematopoietic cells can be used in the present invention. These cells may have been activated by cytokine such as IL-2 in vivo or ex vivo. As these cells, any of cells collected from a living body, or cells obtained via ex vivo culture, for example, a T cell population obtained by the method of the present invention as it is, or obtained by freeze preservation, can be used.

e) Chimeric Antigen Receptor T-Cells (CAR-T)

Artificial T cell receptors (also known as chimeric T cell receptors, chimeric immunoreceptors, chimeric antigen receptors (CARs)) are engineered receptors, which graft an arbitrary specificity onto an immune effector cell. These receptors may be used to graft the specificity of a monoclonal antibody onto a T cell. CARs may consist of a monoclonal antibody fragment, such as a single-chain variable fragment (scFv), that presents on the outside of T-cell membranes, and is fused to intraceullarly-facing stimulatory molecules. The scFv portion may recognize the tumor target. Upon binding, the intracellular stimulatory portions may initiate a signal to activate the T cell.

Artificial T cell receptors may be used as therapy for cancer using adoptive cell transfer. T cells are removed from a patient and modified so that they express receptors specific to the particular form of cancer. The T cells, which can then recognize and kill the cancer cells, are reintroduced into the patient. Modification of T-cells sourced from donors other than the patient may also be used.

14. METHODS OF DELIVERY

Provided herein is a method for delivering the modified cells. The modified cells may be injected or implanted into a mammal, used exogenously, or developed into tissue engineered constructs. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

Also, provided herein is a method for delivering the CRISPR/Cas9-based system to the target cell. The delivery of the CRISPR/Cas9-based system may be the transfection or electroporation of the CRISPR/Cas9-based system as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000. Upon delivery of the CRISPR/Cas9 system to the tissue, and thereupon the vector into the cells of the mammal, the transfected cells will express the CRISPR/Cas9-based system and/or a site-specific nuclease.

15. CONSTRUCTS AND PLASMIDS

A genetic construct, such as a plasmid, may comprise a nucleic acid that encodes the CRISPR/Cas9-based system, such as the Cas9 protein and Cas9 fusion proteins and/or at least one of the gRNAs. The genetic constructs may encode a modified AAV vector and a nucleic acid sequence that encodes the site-specific nuclease, as disclosed herein. The genetic construct, such as a plasmid, may comprise a nucleic acid that encodes the site-specific nuclease. The genetic constructs may encode a modified lentiviral vector, as disclosed herein. The genetic construct, such as a plasmid, may comprise a nucleic acid that encodes the Cas9-fusion protein and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the Cas9-fusion protein or site-specific nuclease, in the cell of a mammal. The vector may be recombinant. The vector may comprise heterologous nucleic acid encoding the fusion protein, such as the Cas9-fusion protein or site-specific nuclease. The vector may be a plasmid. The vector may be useful for transfecting cells with nucleic acid encoding the Cas9-fusion protein or site-specific nuclease, which the transformed host cell is cultured and maintained under conditions wherein expression of the Cas9-fusion protein or the site-specific nuclease system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based system or the site-specific nuclease and may further comprise an initiation codon, which may be upstream of the CRISPR/Cas9-based system or the site-specific nuclease coding sequence, and a stop codon, which may be downstream of the CRISPR/Cas9-based system or the site-specific nuclease coding sequence. The initiation and termination codon may be in frame with the CRISPR/Cas9-based system or the site-specific nuclease coding sequence. The vector may also comprise a promoter that is operably linked to the CRISPR/Cas9-based system or the site-specific nuclease coding sequence. The promoter operably linked to the CRISPR/Cas9-based system or the site-specific nuclease coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based system or the site-specific nuclease. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cas9-based system, i.e., the Cas9 protein or Cas9 fusion protein coding sequence or sgRNAs, or the site-specific nuclease. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based system, including the nucleic acid sequence encoding the Cas9 protein or Cas9 fusion protein and the nucleic acid sequence encoding at least one gRNA comprising the nucleic acid sequence of at least one of SEQ ID NOs: 45-47.

16. KITS

Provided herein is a kit, which may be used to generate the modified cell. The kit comprises a composition for generating the modified cell, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition for generating the modified cell may include a modified AAV vector and a nucleotide sequence encoding a site-specific nuclease, as described above. The site-specific nuclease may include a ZFN, a TALEN, or CRISPR/Cas9-based system, as described above, that specifically binds and cleaves a mutated gene. The site-specific nuclease, as described above, may be included in the kit to specifically bind and target a particular region in the endogenous gene. The site-specific nuclease may be specific for an endogenous IL1r1 or Ccl2 gene, as described above. The kit may further include donor DNA, a gRNA, or a transgene, as described above.

At least one component may include at least one CRISPR/Cas9-based system, as described above, which specifically targets a gene. The kit may include a Cas9 protein or Cas9 fusion protein, a nucleotide sequence encoding said Cas9 protein or Cas9 fusion protein, and/or at least one gRNA. The CRISPR/Cas9-based system, as described above, may be included in the kit to specifically bind and target a particular target region upstream, within or downstream of the coding region of the target gene. For example, a CRISPR/Cas9-based system may be specific for a promoter region of a target gene or a CRISPR/Cas9-based system may be specific for the coding region, as described above. The kit may include donor DNA, as described above.

17. EXAMPLES

The foregoing may be better understood by reference to the following examples, which are presented for purposes of illustration and are not intended to limit the scope of the invention. The present invention has multiple aspects, illustrated by the following non-limiting examples.

Example 1

Methods—Il1r1

Induced pluripotent stem cells (iPSCs) with specific genomic modifications were engineered with specific genomic alterations that confer resistance to inflammation, e.g., resistance to IL-1, and to validate the potential therapeutic utility of these designer stem cells as a source for cartilage tissue engineering and regenerative medicine. CRISPR/Cas9 nucleases capable of mediating deletion of the signal peptide sequence of the interleukin 1 receptor 1 gene (Il1r1), the ligand-binding receptor responsible for IL-1α recognition and involved for IL-1 signal transduction, were transfected into murine iPSCs to generate murine iPSCs deficient in Il1r1. The ability of the cells to synthesize a cartilaginous extracellular matrix (ECM) and resist the inflammation-mediated catabolism initiated by an IL-1α assault was evaluated. Clones were subsequently isolated. Three of 41 iPSC clones possessed the Il1r1+/− genotype and four possessed the Il1r1−/− genotype. Flow cytometry confirmed Il1r1 loss in Il1r1−/− genotyped cells. IL-1α induced NF-κB transcriptional activity in Il1r1+/+ and Il1r1+/− cells but failed to do so in Il1r1−/− cells. Cartilage engineered from Il1r1−/− clones was resistant to IL-1α-mediated degradation, as indicated by gene expression analyses and the preservation of sulfated glycosaminoglycan in the cartilage extracellular matrix, while cartilage derived from Il1r1+/+ and Il1r1+/− clones demonstrated a significant degradative response to the IL-1-mediated in vitro model of OA, including loss of more than 65% of sGAG compared to controls. Using targeted gene editing nucleases, IL-1-resistant pluripotent cells were engineered, demonstrating that stem cells can be tailored at the genomic scale with features suitable for tissue engineering and regenerative medicine applications.

Induced Pluripotent Stem Cell Derivation and Culture.

Murine induced pluripotent stem cells were derived and cultured as previously described (Diekman et al., (2012) Proc. Natl. Acad. Sci. 109:19172-19177). Briefly, tail fibroblasts from adult C57BL/6 mice were transduced with a lentiviral vector driving doxycycline-inducible expression of Oct4 (Pou5f1), Sox2, Klf4, and c-myc (Carey et al., (2009) Proc. Natl. Acad. Sci. 106:157-162). Pluripotent cells were maintained on mitomycin C-treated mouse embryonic feeders (MEFs; Millipore) in medium comprised of high glucose Dulbecco's modified Eagle's medium (DMEM) supplemented with L-glutamine, sodium pyruvate, 20% fetal bovine serum, 100 nM minimum essential medium non-essential amino acids (NEAA; Gibco), 55 µM β-mercaptoethanol (2-ME; Gibco), and 1,000 units of leukemia inhibitory factor (LIF; Millipore). A Col2a1-GFP reporter construct (Grant et al., (2000) Developmental Dynamics 218:394-400) was transfected into cells by Nucleofection, and a clone stably expressing the reporter upon chondrogenic induction was isolated after G418 selection.

Genome Editing and Clonal Isolation.

A plasmid encoding human codon optimized *Streptococcus pyogenes* Cas9 (hCas9) was as previously described (Mali et al., (2013) Science 339:823-826) (Addgene plasmid #41815). Target sequences flanking exon 2 of Il1r1 and corresponding to 5'-GCTTCTGTGTTGAAGACTCA-3' (SEQ ID NO: 1) and 5'-GTAGCTGTGGGCCCACAACC-3' (SEQ ID NO: 2) were selected to generate the deletion of the Il1r1 signal peptide sequence. To produce single chimeric guide RNA (sgRNA) expression vectors, complementary oligonucleotides containing each of the target sequences were hybridized, phosphorylated, and cloned into an expression vector (Perez-Pinera et al., (2013) Nat. Meth. 10:973-976) (Addgene plasmid #47108) employing an human U6 promoter to drive expression of a chimeric *Streptococcus pyogenes* crRNA/tracrRNA sequence. The gRNA sequences were sgRNA_Il1r1-4: GCTTCTGTGTTGAAGACTCA (SEQ ID NO: 43) and sgRNA_Il1r1-6: GTAGCTGTGGGCCCACAACC (SEQ ID NO: 44). Prior to transfection, iPSCs were trypsinized and subjected to a 30-minute feeder subtraction. Lipofectamine 2000 (Life Technologies) was used following manufacturer's instructions to co-transfect 400 ng of each sgRNA and 800 ng hCas9 into 100,000 iPSCs freshly plated on MEFs in complete, antibiotic-free iPSC medium in a 24-well plate. Cells were then sub-cultured on MEFs prior to single-cell deposition. In preparation for single cell deposition, iPSCs were feeder subtracted prior to overnight culture on 0.1% gelatin. Cells were then trypsinized and subjected to a final feeder subtraction and then suspended in calcium- and magnesium-free PBS, 1 mM EDTA, 25 mM HEPES, and 1% FBS. Individual cells were then deposited into gelatin-coated wells of a 96-well plate. Clones were sub-cultured on gelatin for one additional passage to allow for screening for the appropriate deletion via genomic PCR using the following primer pair: Il1r1 detF-5'-TCATCTCCTGGTTAGT-TATGGTATC-3' (SEQ ID NO: 3) and Il1r1 detR-5'-CCGAGGCCAATGAGATTAAG-3' (SEQ ID NO: 4). A subset of each clone was lysed using QuickExtract (Epicentre) according to the manufacturer's instructions. The cell lysate was then diluted 8-10 fold prior to use as template in a PCR using Q5 polymerase (NEB) according to manufacturer's instruction with the following cycling parameters: 98/30"|98/8"; 68/10"; 72/20"|×40; 72/2'. Clones of interest exhibiting Il1r1+/+, Il1r1+/−, and Il1r1−/− genotypes were passaged on MEFs and culture expanded in preparation for micromass culture.

Micromass Pre-Differentiation Culture.

Induced pluripotent stem cells were subjected to a 15-day, high-density micromass culture to achieve differentiation toward a mesenchymal state. Cells were cultured in serum-free differentiation medium consisting of high glucose DMEM, NEAA, 2-ME, ITS+ (insulin, transferrin, selenium) premix supplement (BD), 25 ng/ml gentamicin, 50 µg/ml L-ascorbic acid-phosphate, and 40 µg/ml L-proline. On days 3-5 only, medium was supplemented with 100 nM dexamethasone (Sigma) and 50 ng/ml murine BMP-4 (R&D Systems). Micromasses were dissociated on day 15 with pronase and type II collagenase in order to attain a single cell suspension, and flow cytometry was used to sort GFP+ cells based on Col2a1 reporter expression. GFP+ cells were plated in monolayer on gelatinized vessels and cultured in differentiation medium supplemented with 4 ng/ml bFGF (Roche) and 10% FBS for 2-3 passages. Cells were subsequently utilized in monolayer assays for functional Il1r1 protein or in cartilage tissue engineering experiments evaluating the utility of these cells as a source for IL-1-protected tissue regeneration.

Flow Cytometry.

Induced pluripotent stem cells and pre-differentiated cells were trypsinized, washed in PBS, and resuspended in PBS with 1% FBS supplemented with 5 µg/ml anti-mouse CD16/32 (Biolegend) to block non-specific immunolabeling. Cells were then immunolabeled with either an Armenian hamster anti-mouse CD121a antibody conjugated to phycoerythrin or an isotype control (Biolegend). Cells were washed three times then subjected to flow cytometry analysis to determine the presence or absence of Il1r1.

NF-κB Activity Assay.

A lentiviral construct containing 5 tandem NF-κB response elements (5'-GGAAATTCCCG-GAAAGTCCCCGGAAATTCCCGGAAAGTCCCCG-GAAATTCCC-3' (SEQ ID NO: 5)) upstream of firefly luciferase was generated by cloning the following sequence upstream of the minimal CMV promoter in pGL3Basic (Promega) and then sub-cloning the cassette into a lentiviral expression vector. Lentivirus was generated by co-transfecting 4 µg of the cloned transfer vector, 3 µg of psPAX2 (Addgene 12260) and 1.2 µg of pMD2G (Addgene #12259) into 293T cells cultured at confluence in the well of a 6-well plate using Lipofectamine 2000. The next day, medium from 293T lentivirus producer cells was changed and conditioned medium containing lentivirus was collected 36 and 60 hours after transfection. The lentiviral supernatant was filtered through 0.45 um cellulose acetate filters and stored at −80° C. until use.

Pre-differentiated cells were transduced by supplementing culture medium 1:1 with viral supernatant as well as 4 µg/ml polybrene and incubating the cells in the presence of the virus overnight. Transduced cells were expanded, passaged, and then treated with IL-1. At the indicated time points, samples were lysed and assayed for luminescence using a Bright Glo luminescence kit according to manufacturer's instructions. Luminescence normalized to background levels of 0 ng/ml IL1 treatment were used to report induction of NF-κB transcriptional activity.

Chondrogenesis in Aggregate Culture System.

Passage 2 pre-differentiated cells were trypsinized and resuspended in differentiation medium supplemented with 100 nM dexamethasone and 10 ng/ml TGF-β3 (R&D Systems) at a density of 1e6 cells/ml. Aggregate cultures were produced by placing 250,000 cells in each well of a round-bottom 96-well plate. Cells were pelleted and cultured for 27 days prior to inducing an inflammatory assault utilizing an established in vitro osteoarthritis model (Willard et al., (2014) Arthritis Rheumatol. 66:3062-3072). At day 27, cells were cultured in differentiation medium supplemented with 1 ng/ml IL-1α and without dexamethasone and TGF-β3. Control aggregates received 0 ng/ml IL-1α. Three days later, aggregate cultures and culture supernatant samples were harvested for gene expression, biochemical, and histological analyses.

Biochemical Analyses.

Samples used for biochemical analyses were harvested, rinsed with DPBS, and stored at −20° C. until testing. Aggregate culture samples were digested in papain (125 µg/ml; Sigma) at 65° C. overnight. Digested samples were then analyzed using the picogreen assay (Life Technologies) to measure double-stranded DNA, the ortho-hydroxyproline assay (Woessner, (1961) Arch. Biochem. Biophys. 93:440-447) for measuring total collagen content, and the dimethylmethylene blue assay (Farndale et al., (1986) Biochim. Biophys. Acta 883:173-177) for measuring the total sulfated glycosaminoglycan content of constructs (n=4-6 per group).

Gene Expression.

Samples for gene expression analysis were harvested, rinsed in DPBS, and frozen at −80° C. until further processing. Total RNA was isolated per manufacturer's recommendations (Norgen Biotek) following tissue homogenization with a pestle. Reverse transcription was performed using the superscript VILO cDNA synthesis kit (Life Technologies) per manufacturer's instructions. Quantitative RT-PCR was performed with n=4 samples per group on a StepOnePlus using Power Sybr (Applied Biosystems, Inc.) per manufacturer's instructions. Fold changes were determined relative to a reference group cultured without IL-1α and by using 18s rRNA as a reference gene. Gene expression was probed using the primer pairs listed in Table 1.

TABLE 1

Primers Pairs used in qRT-PCR gene expression assays.

| Target | | SEQ ID NO: |
|---|---|---|
| Forward Primer | | |
| r18s | 5'-CGGCTACCACATCCAAGGAA-3' | 6 |
| Acan | 5'-GCATGAGAGAGGCGAATGGA-3' | 7 |
| Adamts4 | 5'-GACCTTCCGTGAAGAGCAGTGT-3' | 8 |
| Adamts5 | 5'-GCCCACCCAATGGTAAATCTTT-3' | 9 |
| Ccl2 | 5'-GGCTCAGCCAGATGCAGTTAA-3' | 10 |
| Col2a1 | 5'-TCCAGATGACTTTCCTCCGTCTA-3' | 11 |
| Elf3 | 5'-GGCCCTCATGGCTGCCACCT-3' | 12 |
| IL6 | 5'-GAGGATACCACTCCCAACAGACC-3' | 13 |
| Mmp9 | 5'-CGAACTTCGACACTGACAAGAAGT-3' | 14 |
| Mmp13 | 5'-GGGCTCTGAATGGTTATGACATTC-3' | 15 |
| Reverse Primer | | |
| r18s | 5'-GGGCCTCGAAAGAGTCCTGT-3' | 16 |
| Acan | 5'-CTGATCTCGTAGCGATCTTTCTTCT-3' | 17 |
| Adamts4 | 5'-CCTGGCAGGTGAGTTTGCAT-3' | 18 |
| Adamts5 | 5'-TGACTCCTTTTGCATCAGACTGA-3' | 19 |
| Ccl2 | 5'-CCTACTCATTGGGATCATCTTGCT-3' | 20 |
| Col2a1 | 5'-AGGTAGGCGATGCTGTTCTTACA-3' | 21 |
| Elf3 | 5'-TTGGGATCTTGTCTGAGGTCCTGGA-3' | 22 |
| IL6 | 5'-AAGTGCATCATCGTTGTTCATACA-3' | 23 |
| Mmp9 | 5'-GCACGCTGGAATGATCTAAGC-3' | 24 |
| Mmp13 | 5'-AGCGCTCAGTCTCTTCACCTCTT-3' | 25 |

Histological Processing.

Samples for histology were rinsed in DPBS upon harvest, fixed in 4% paraformaldehyde for 24 hours, paraffin embedded, and sectioned at 10 μm thickness. Samples were stained with Safranin-O/fast green/hematoxylin using standard protocols.

Analyses of Culture Supernatants.

Nitric oxide, Prostaglandin E2, sGAG, MMP activities were measured in medium samples (n=4) collected after IL-1α treatment as previously described (McNulty et al., (2011) Connective Tissue Research 52:523-533). As with biochemical samples, sGAG in medium samples was assessed using the DMMB assay. MMP activity was assessed after activating latent MMPs in supernates with p-APMA. Total specific MMP activity was measured as the difference in fluorescence arising from cleavage of a quenched fluorogenic substrate (DAB-Gly-Pro-Leu-Gly-Met-Arg-Gly-Lys-Flu, Sigma) in samples incubated with a broad-spectrum MMP inhibitor GM6001 and a scrambled negative control peptide (EMD Biosciences Inc.). NO and PGE2 were assayed using commercially available kits (R&D Systems) following manufacturer's instructions.

Statistical Analyses.

Statistical analysis was performed in the Statistica 7 software package using ANOVA with Fisher's protected least significance difference post-hoc test with $\alpha=0.05$. For qRT-PCR comparisons, fold change values were log-transformed prior to statistical analysis. Average group values and standard errors of the means were calculated in the logarithmic space prior to transforming data to linear values for reporting fold changes.

Example 2

Results—Clonal Isolation and Confirmation of Il1r1 Functional Deficit

Figure 5A:
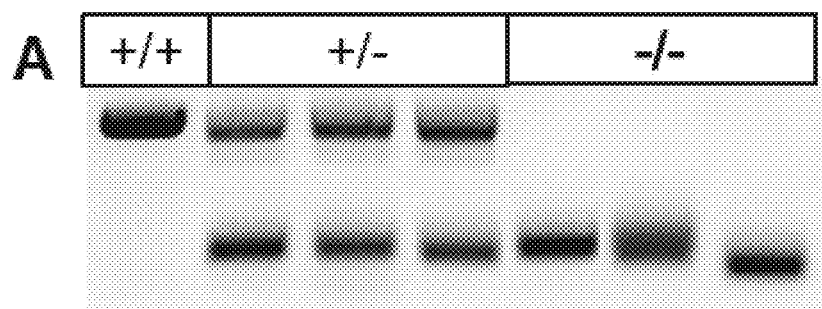
FIG. 5A shows genomic PCR from clones isolated after single-cell deposition. PCR amplicons represent the presence or absence of exon 2 in the Il1r1 locus.
Figure 5B:
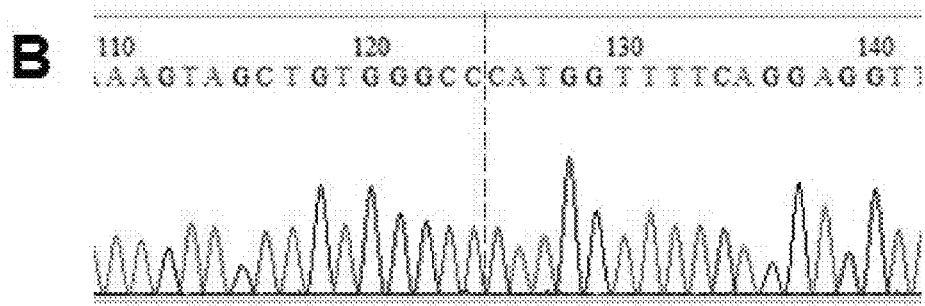
FIG. 5B shows Sanger sequencing from an allele with the CRISPR/Cas9-mediated deletion of exon2 from Il1r1.
Figure 5C:
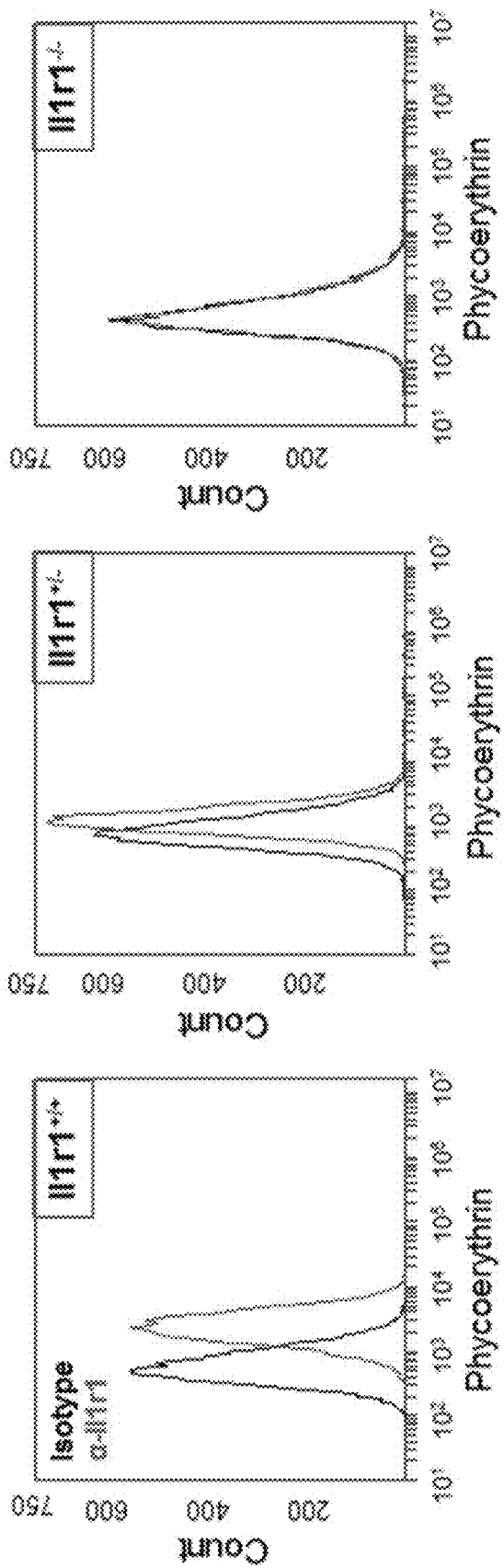
FIG. 5C shows the flow cytometry histograms demonstrating differential levels of Il1r1 surface expression in populations derived from each of the Il1r1+/+, Il1r1+/− and Il1r1−/− genotypes.
Figure 5D:
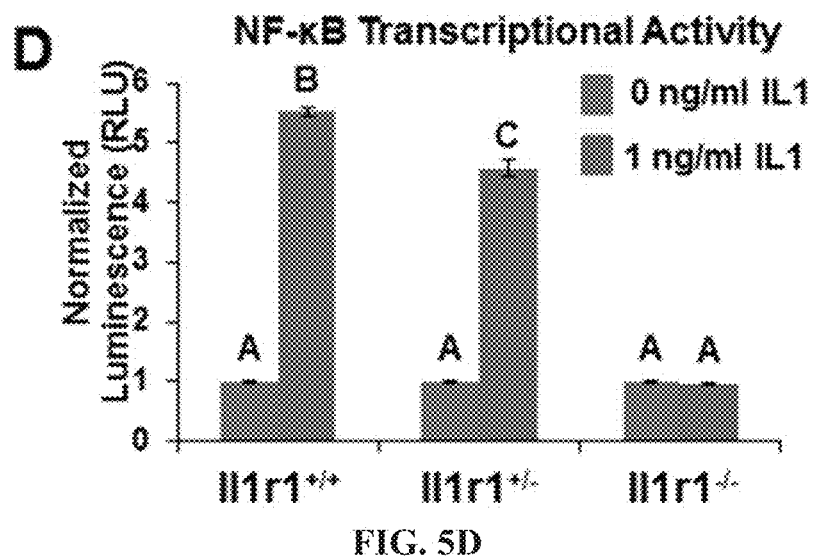
FIG. 5D shows luminescence data characterizing the transcriptional activity of NF-κB in Il1r1+/+, Il1r1+/−, and Il1r1−/− cells after a 24 hour treatment with 1 ng/ml IL-1α. Bars represent group means±SEM (n=4). Groups not sharing the same letter are statistically different ($p<0.05$).
Figure 6A:
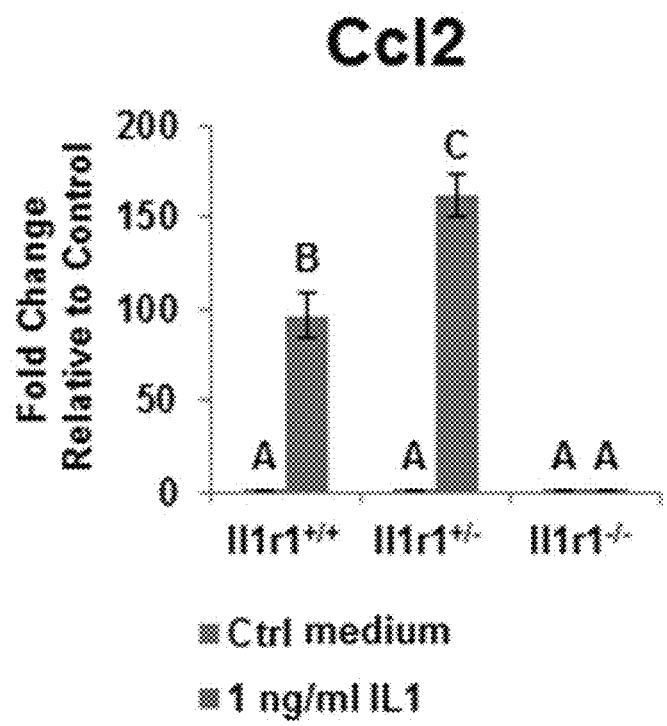
FIGS. 6A-6I show relative gene expression data for Ccl2 (FIG. 6A), Il6 (FIG. 6B), Elf3 (FIG. 6C), Adamts4 (FIG. 6D), Adamts5 (FIG. 6E), Mmp9 (FIG. 6F), Acan (FIG. 6H), and Col2a1 (FIG. 6I) as measured by qRT-PCR to examine the effects of IL-1α treatment on engineered cartilage derived from either Il1r1+/+, Il1r1+/−, or Il1r1−/− cells. Fold changes were determined relative to a reference group cultured without IL-1α and by using 18 s rRNA as a reference gene. Bars represent group means of fold change±SEM (n=4). Groups not sharing the same letter are statistically different ($p<0.05$).
Figure 6B:
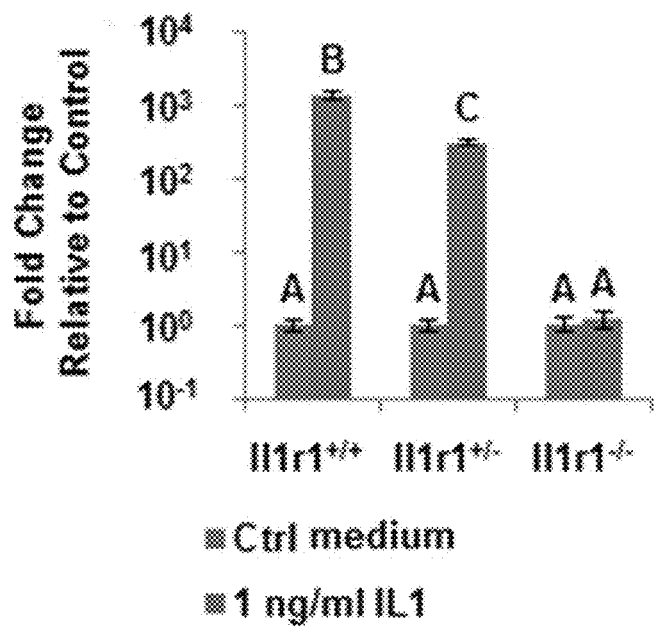
Figure 6C:
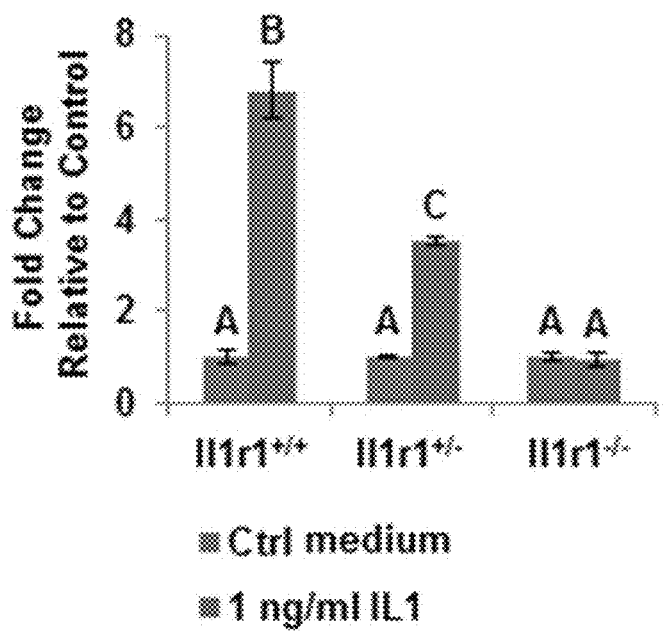
Figure 6D:
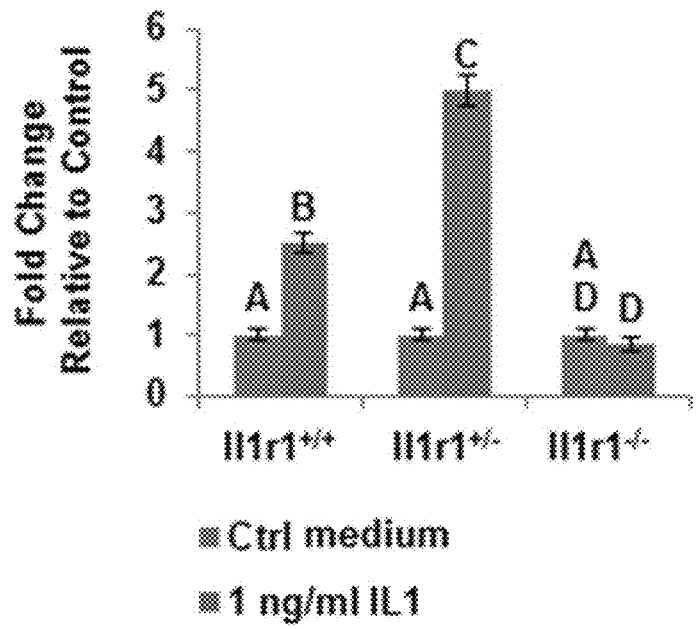
Figure 6E:
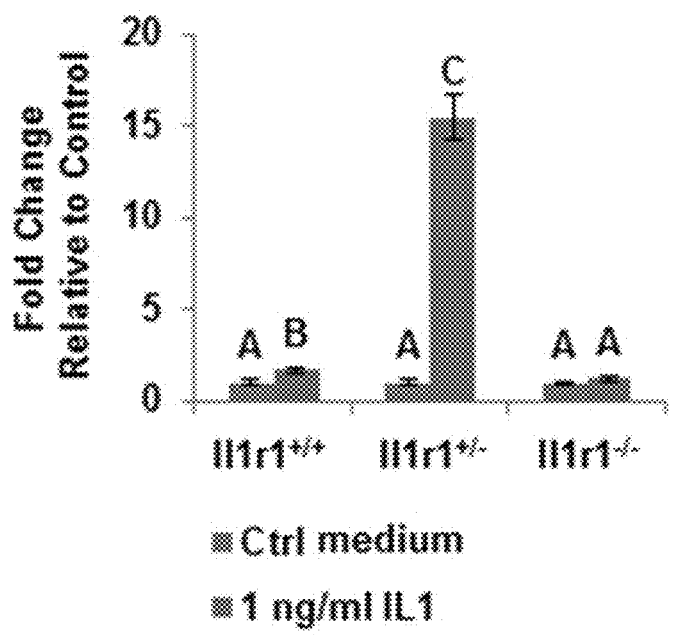
Figure 6F:
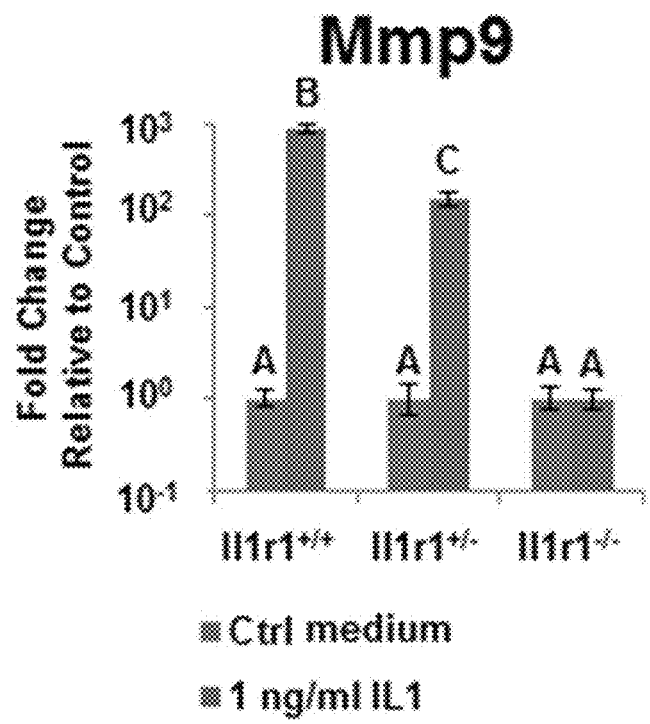
Figure 6G:
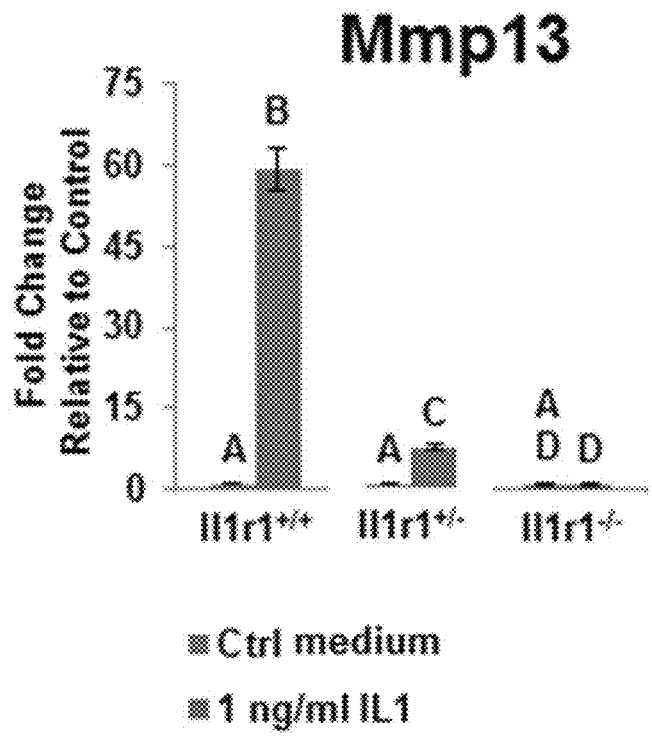
Figure 6H:
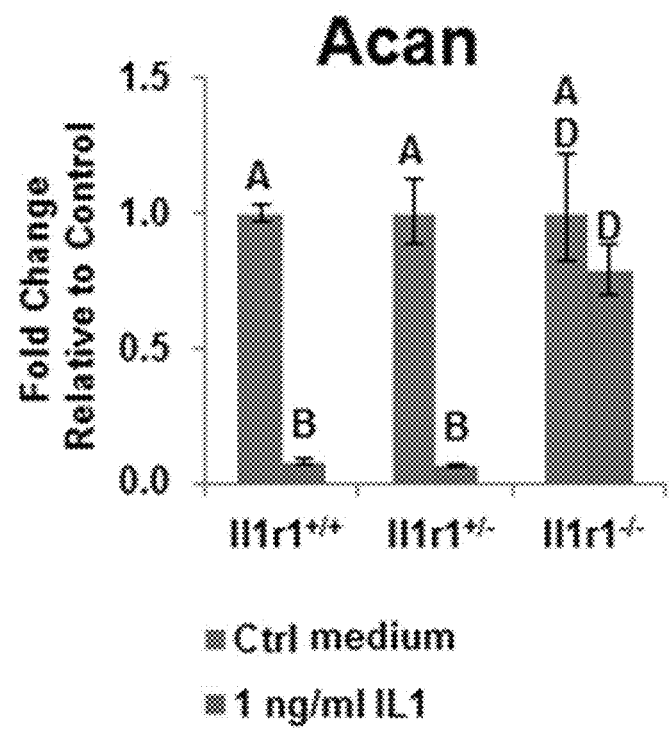
Figure 6I:
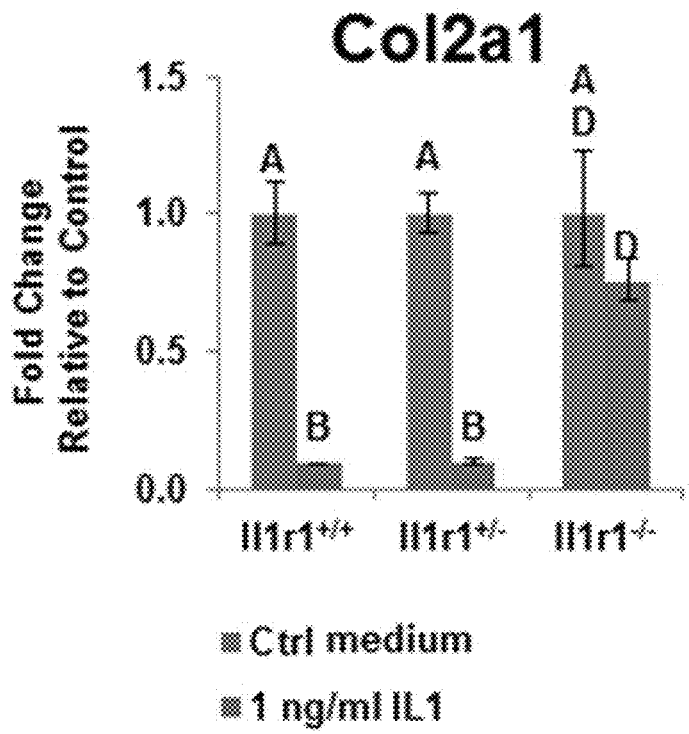

Forty-one clones were isolated and screened after single cell deposition. Of these, three were found to possess the Il1r1+/− genotype while four possessed the Il1r1−/− genotype (FIG. 5A). Sanger sequencing of the PCR product from the Il1r1−/− clones indicates the expected deletion of approximately 790 base pairs, resulting in excision of the signal peptide for both annotated Il1r1 isoforms (FIG. 5B). Flow cytometry demonstrated that wild-type cells in the pluripotent state do not express Il1r1 (FIG. 5C). However, in select clones that were chondrogenically differentiated, a uniform shift occurred in the wild-type (FIG. 5C) population after staining with the anti-Il1r1 antibody, suggesting low but consistent expression of Il1r1 on the cell surface. The Il1r1+/− population also displayed a uniform shift, with roughly half the intensity of Il1r1+/+ cells, demonstrating reduced expression of Il1r1 protein after loss of one functional allele. Cells possessing the Il1r1−/− genotype lacked any positive staining for Il1r1 (FIG. 5C). The absence of the Il1r1 receptor on the cell surface resulted in a functional deficiency, as indicated by an absence of NF-κB activity after IL-1α stimulation, whereas stimulated wild-type and Il1r1+/− cells exhibited a 6.3- and 4.8-fold induction, respectively (FIG. 5D).

Example 3

Cartilage Engineered from CRISPR/Cas9-Edited iPSCs is Protected from IL-1α

Gene expression assays demonstrated that IL-1α (1 ng/ml) induced significant upregulation of catabolic gene products and markers of inflammation in aggregates derived from cells with intact Il1r1 (FIG. 6). Ccl2 and Il6, soluble mediators of OA and sentinel markers of inflammation, were elevated over 50-fold at 72 hrs in the Il1r1+/+ and Il1r1+/− aggregates ($p<10e-6$). Expression of catabolic enzymes responsible for cartilage matrix degradation, such as Adamts4, Adamts5, Mmp9, and Mmp13, were significantly upregulated in aggregates generated with functional Il1r1 ($p<0.007$). Expression of Elf3, a transcription factor responsible for cytokine-induced suppression of type II collagen (Peng et al., 2008), was also upregulated in Il1r1+/+ and Il1r1+/− aggregates ($p<10e-6$). This corresponded to a concomitant reduction in Col2a1 expression in the same aggregates after IL-1α induction ($p<10e-6$). Furthermore, Acan expression was suppressed after IL-1α treatment in Il1r1+/+ and Il1r1+/− aggregates as well ($p<10e-6$). However, soluble markers of inflammation ($p>0.30$), catabolic enzymes ($p>0.12$), and pro-inflammatory transcription factors were not upregulated in Il1r1−/− aggregates ($p>0.64$). Moreover, Col2a1 and Acan expression were unaffected by IL-1α induction ($p>0.07$, FIG. 6).

Figure 7A:
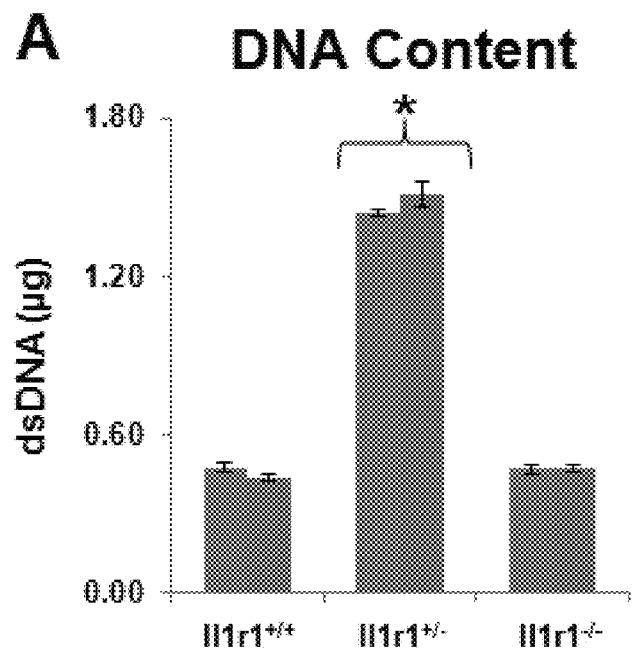
FIGS. 7A-7F show the biochemical analyses of engineered cartilage composition.
Figure 7B:
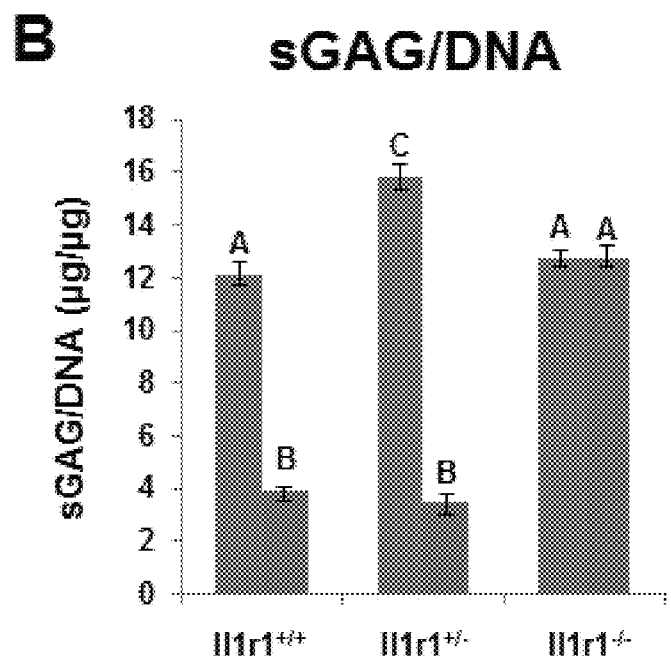
Figure 7C:
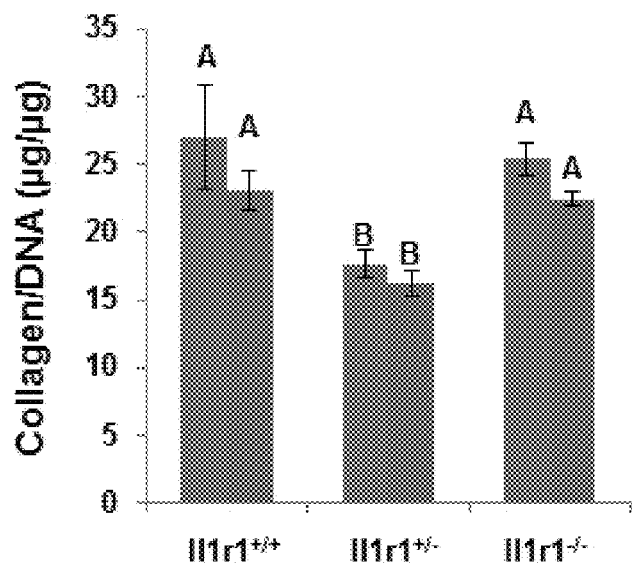
Figure 7D:
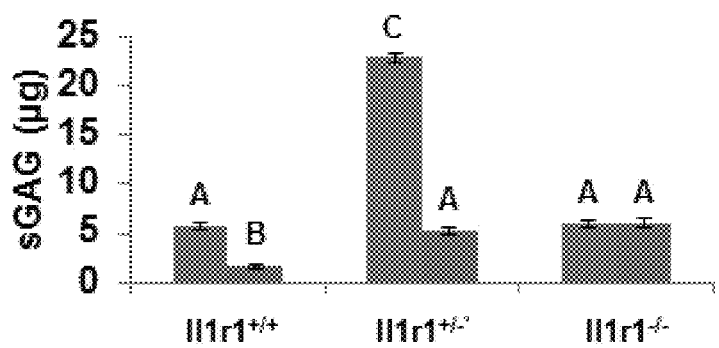
Figure 7E:
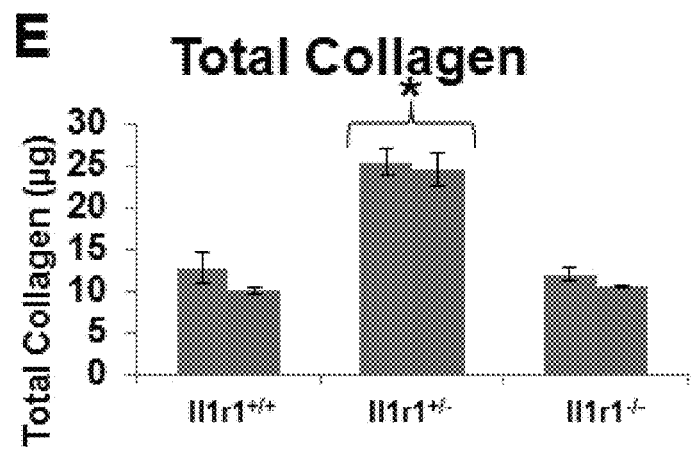

In accordance with the observed changes at the transcriptional level, treatment with IL-1α resulted in an altered biochemical composition of cartilage aggregates generated from the Il1r1+/+ and Il1r1+/− genotypes. Treatment with IL-1 had no effect on DNA content in aggregates (FIG. 7A). Interestingly, DNA content in Il1r1+/− pellets was significantly higher than DNA content in aggregates derived from Il1r1+/+ or Il1r1−/− cells, possibly due to a higher level of proliferation or cell survival in the clone chosen for these experiments. Concomitant with this increased DNA content, aggregates derived from Il1r1+/− displayed increased accumulation of sGAG and total collagen. Despite this increased accumulation, Il1r1+/−-derived cartilage remained highly responsive to IL-1α. Sulfated GAG was found to be significantly dependent on IL-1α treatment and genotype, with aggregates derived from Il1r1+/+ or Il1r1+/− clones losing over 65% of sGAG or sGAG/DNA (p<10e-6, FIG. 7B, FIG. 7D). Aggregates engineered from CRISPR/Cas9-edited Il1r1−/− cells were protected from the IL-1α treatment, with no significant difference in sGAG or sGAG/DNA content associated with IL-1α treatment (p>0.95). No significant differences due to IL-1α were found for total collagen or total collagen/DNA (FIG. 7C, FIG. 7E).

Figure 7F:
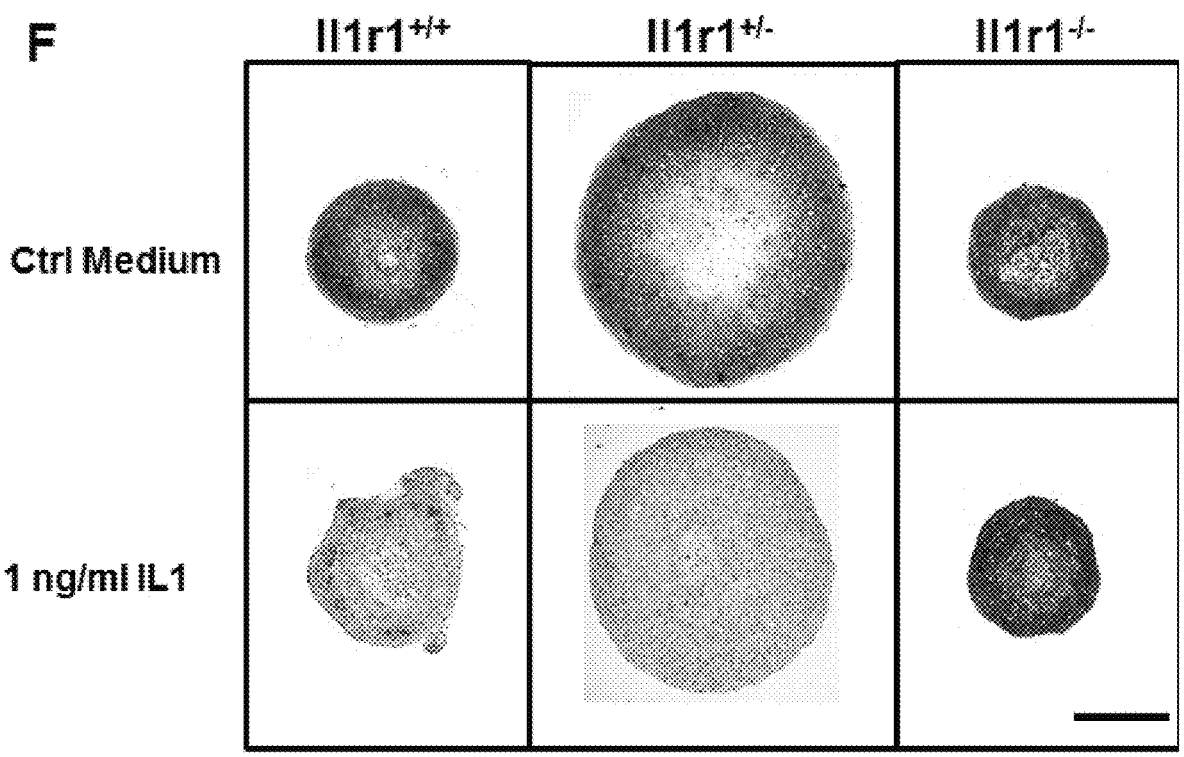

Histological findings support the changes observed in matrix composition from biochemical analyses (FIG. 7F). A GAG-rich matrix developed in all genotypes after maturation of engineered cartilage. As suggested by the biochemical data, larger aggregates developed from Il1r1+/− cells. However, a marked reduction of Safranin-O staining was observed in aggregates with intact Il1r1 after IL-1 treatment, consistent with the biochemical measurement of loss of sGAG for both Il1r1+/+ and Il1r1+/−-derived aggregates.

Figure 8A:
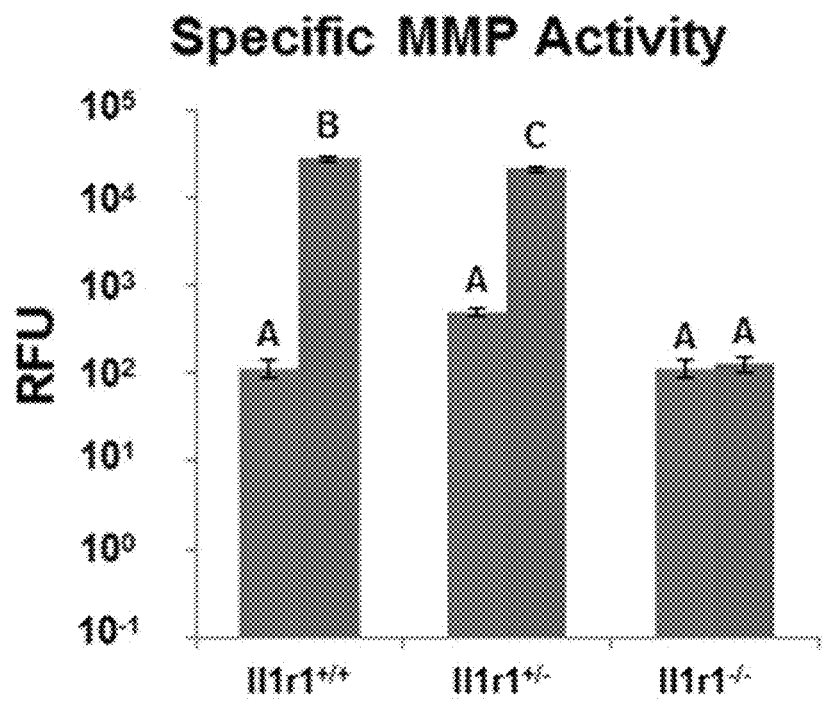
FIGS. 8A-8D show the analysis of media samples collected from engineered cartilage aggregates cultured with or without 1 ng/ml IL-1α for 72 hours.
Figure 8B:
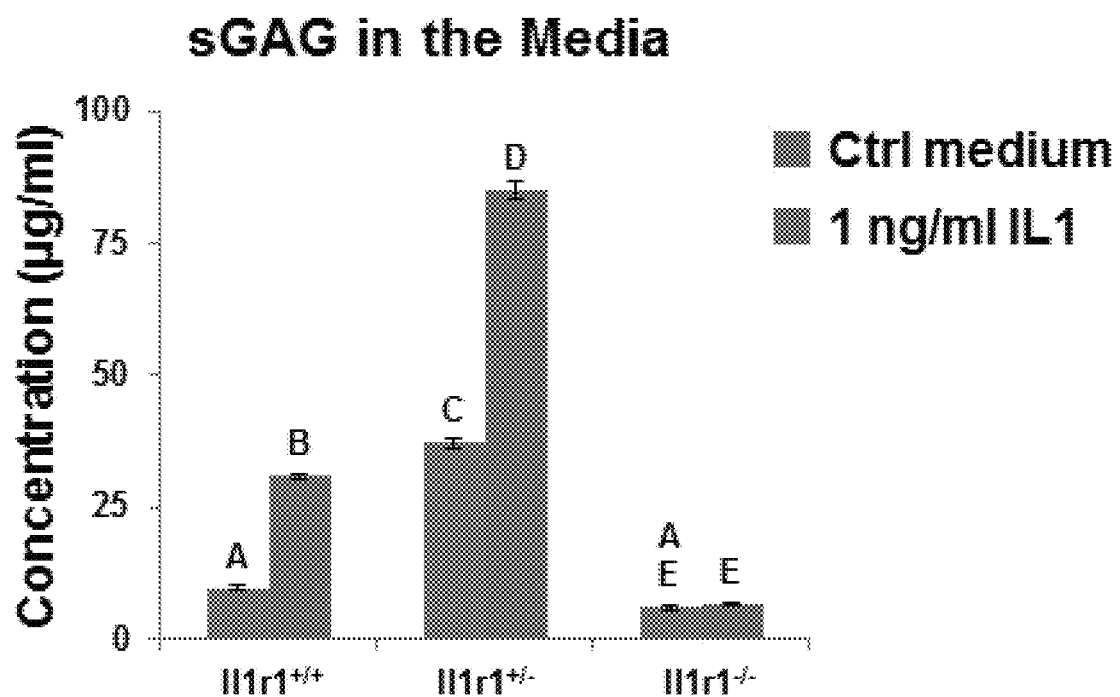
Figure 8C:
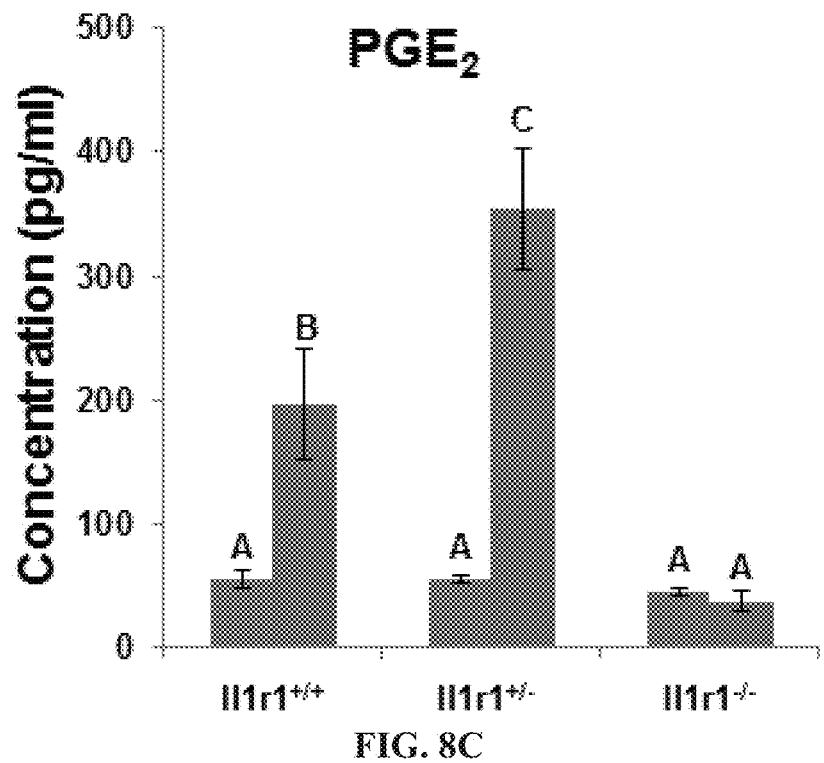
Figure 8D:
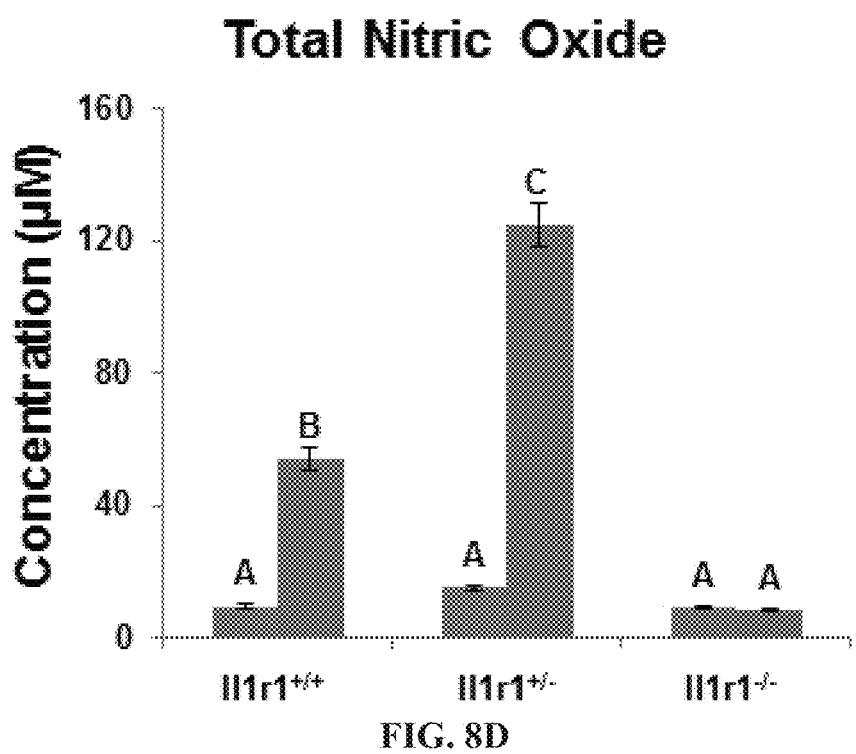
Figure 9A:
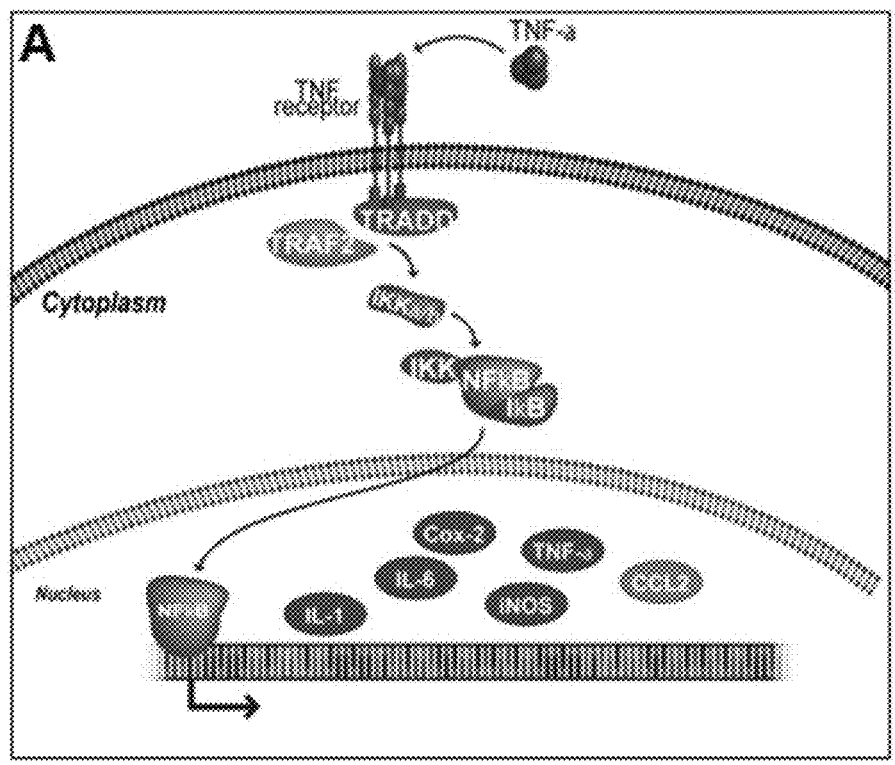
FIGS. 9A-9D show a depiction of the re-purposed inflammatory signaling pathway in CRISPR/Cas9-engineered cells.
Figure 9B:
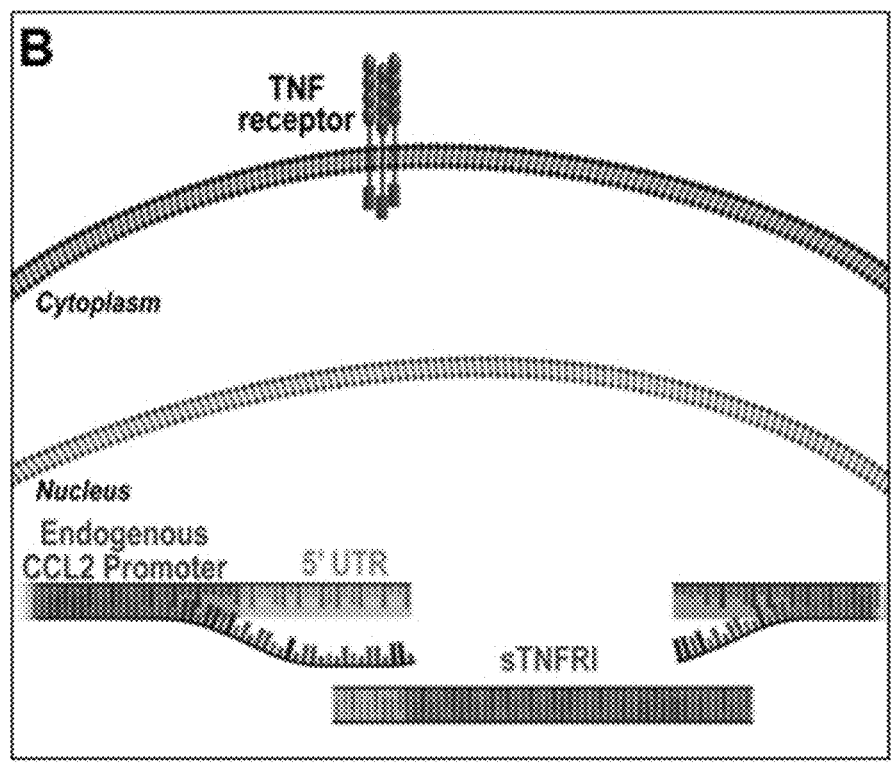
Figure 9C:
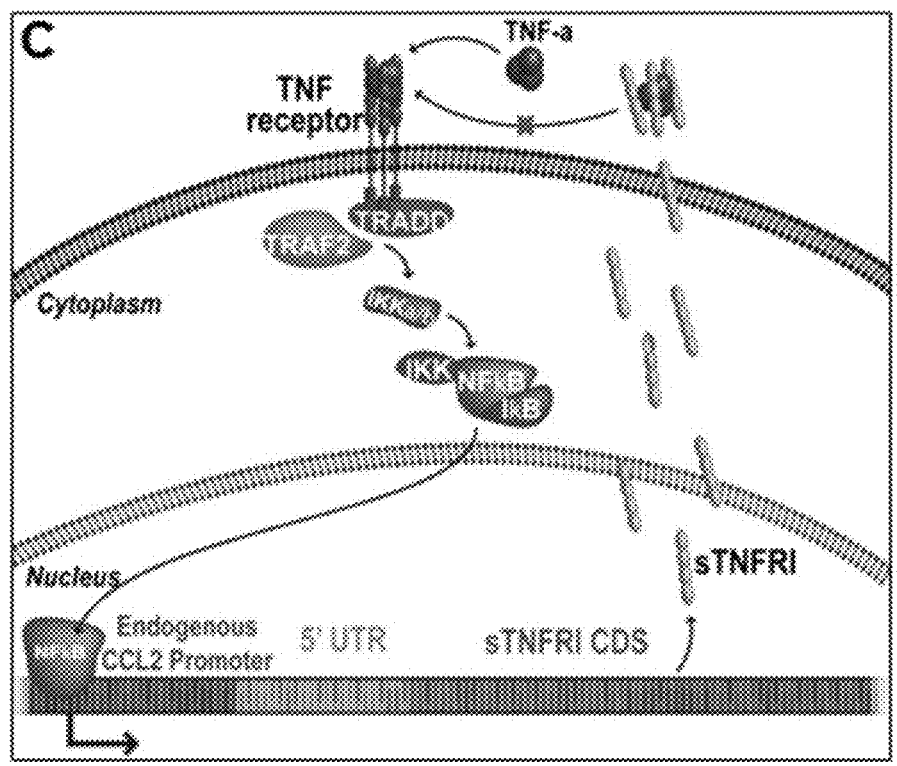
Figure 9D:
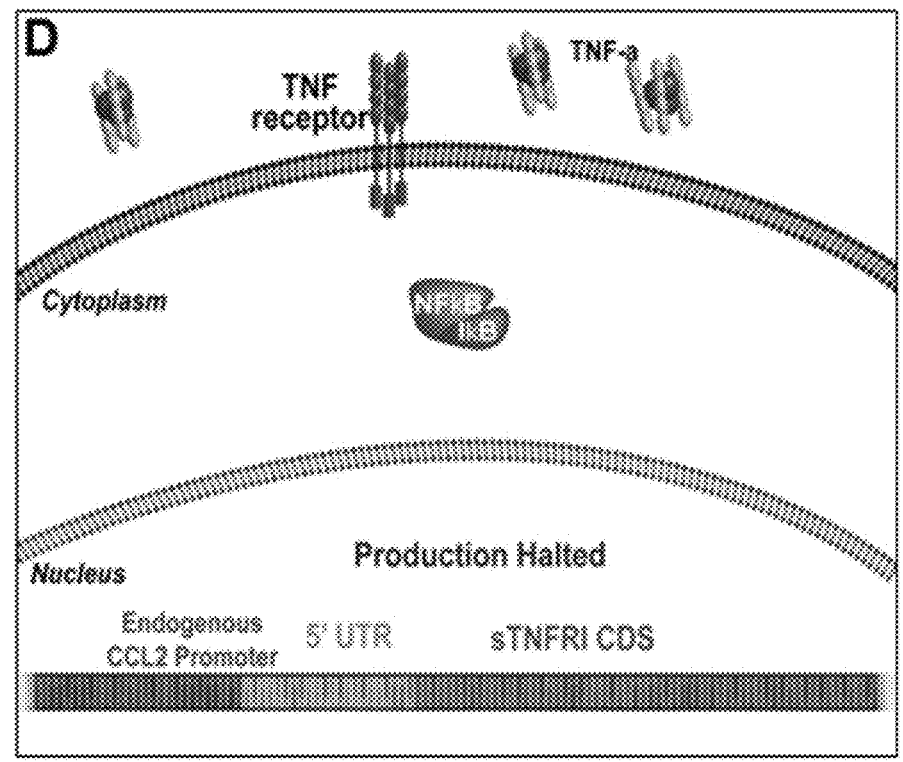

Culture media collected from Il1r1+/+ and Il1r1+/− samples displayed features characteristic of a degenerative environment after a 72-hour treatment with IL-1α, whereas media collected from Il1r1−/− samples exhibited no signs of IL-1α-responsiveness (FIGS. 8A-8D). Specific MMP activity was significantly elevated in media collected from IL-1α-treated Il1r1+/+ and Il1r1+/− aggregates (FIG. 8A), likely contributing to the elevated levels of sGAG detected in the same media samples (FIG. 8B). The accumulation of significantly higher levels of sGAG in these samples is consistent with the observed loss of sGAG in engineered cartilage derived from Il1r1+/+ and Il1r1+/− cells. Furthermore, the higher levels of PGE2 and total nitric oxide species found in Il1r1+/+ and Il1r1+/− samples (FIG. 8C and FIG. 8D) reflects the inflammatory state IL-1α was capable of inducing when Il1r1-competent cells were used to engineer cartilage, while IL-1α did not affect the of the Il1r1−/−-derived cartilage.

This work demonstrates the utility of programmable nucleases for applications in tissue engineering and regenerative medicine by developing stem cells with customized properties at the scale of the genome. Using targeted gene editing nucleases, pluripotent stem cells were engineered with the trait of IL-1-resistance by deleting the Il1r1 signal peptide sequence. CRISPR/Cas9-mediated editing of the Il1r1 locus resulted in complete loss of IL-1 signaling by all measures evaluated. Cartilage derived from CRISPR/Cas9-edited pluripotent stem cells displayed the capacity to withstand treatment with 1 ng/ml IL-1. Taken together, these results indicate that genome editing serves as an effective means for generating stem cells with application-specific features pertinent to tissue regeneration, maintenance, and repair. The pro-inflammatory environment generates a disruption of the collagenous network that normally resists swelling of the tissue and also results in catabolism of the intertwined proteoglycan mesh, leading to severe cartilage erosion.

Cartilage derived from either Il1r1+/+ or Il1r1+/− cells was highly susceptible to this in vitro model of OA, as shown by extreme loss of sGAG and production of degradative enzymes such as MMPs as well as pro-inflammatory mediators including PGE2 and NO. Furthermore, cartilage derived from Il1r1+/+ and Il1r1−/− cells showed a significant induction of a pro-inflammatory gene transcriptional program after IL-1 treatment. However, cartilage derived from CRISPR/Cas9-engineered cells lacking functional Il1r1 demonstrated complete protection from IL-1 treatment, including preservation of extracellular matrix constituents as observed histologically and biochemically, as well as a lack of induction of catabolic enzymes and pro-inflammatory mediators.

The results show that genome editing with CRISPR/Cas9 yielded the desired genomic modification in more than 10% of isolated clones in an unselected population. This method allows for site-specific gene deletion independent of targeting donor vectors that harbor gene traps or loxP sites that facilitate subsequent Cre-mediated excision. Thus, this approach overcomes the need for ectopic overexpression of selectable markers or Cre recombinase, and allows for direct, efficient gene editing.

The data suggests that the presence of IL-1Ra is sufficient to combat pathologic levels of IL-1, which may prove challenging if engineered tissues remain susceptible to high levels of IL-1 signaling. Cartilage engineered from cells rendered incapable of transducing the IL-1 signal may serve as an ideal cell-based drug delivery platform, which may remain intact in the presence of high levels of IL-1 while functioning to protect the surrounding, IL1R1-competent cells from IL-1 signaling by secreting IL-1Ra into the inflamed microenvironment.

Example 4

Methods—Ccl2

A treatment of chronic inflammatory diseases such as arthritis was developed with stem cells that can autonomously execute real-time, programmed responses to pro-inflammatory cytokines. Genome editing nucleases based on the CRISPR/Cas9 platform were used to introduce specific modifications to chromosomal gene sequences in iPSCs. Targeted addition of transgenes encoding cytokine antagonists was performed to create a closed-loop gene circuit based on the inflammation-inducible chemokine Ccl2 endogenous locus. Such targeted gene modification imparted self-regulated, feedback-controlled production of biologic therapy induced by the inflammatory transcriptional program controlled by cytokines such as IL-1 and TNF-α. Repurposing of degradative signaling pathways toward transient production of cytokine antagonists enabled engineered cartilage tissue to withstand the action of inflammatory cytokines and serve as a cell-based autoregulated drug delivery system. Treatment of genetically engineered iPSCs with either IL-1α or TNF-α resulted in upregulated transgene transcription in response to endogenous Ccl2 activation in a dose- and time-dependent manner. Expression profiles demonstrated rapid induction and subsequent decay of transgene expression concomitant with attenuation of cytokine signaling. Cartilage derived from cells autonomously expressing anti-cytokine biologics was protected from cytokine-mediated degradation as compared to cartilage engineered from control cells. This resulted in preservation of the cartilage ECM as measured by quantitative biochemical assays and histology. This work demonstrates the utility of genome engineering for the development of stem cells with properties customized for cell-based regenerative medicine strategies for the treatment of chronic inflammatory diseases Induced Pluripotent Stem Cell Derivation and Culture.

Murine induced pluripotent stem cells were derived and cultured as previously described (Diekman et al., (2012) Proc. Natl. Acad. Sci. 109:19172-19177). Briefly, tail fibroblasts from adult C57BL/6 mice were transduced with a lentiviral vector driving doxycycline-inducible expression of Oct4 (Pou5f1), Sox2, Klf4, and c-myc (Carey et al., (2009) Proc. Natl. Acad. Sci. 106:157-162). Pluripotent cells were maintained on mitomycin C-treated mouse embryonic feeders (MEFs; Millipore) in medium comprised of high glucose Dulbecco's modified Eagle's medium (DMEM) supplemented with L-glutamine, sodium pyruvate, 20% fetal bovine serum, 100 nM minimum essential medium non-essential amino acids (NEAA; Gibco), 55 µM β-mercaptoethanol (2-ME; Gibco), and 1,000 units of leukemia inhibitory factor (LIF; Millipore). A Col2a1-GFP reporter construct (Grant et al., 2000) was transfected into cells by Nucleofection, and a clone stably expressing the reporter upon chondrogenic induction was isolated after G418 selection.

Genome Editing and Clonal Isolation.

A plasmid encoding human codon optimized *Streptococcus pyogenes* Cas9 (hCas9) was obtained as a gift from George Church (Mali et al., 2013) (Addgene plasmid #41815). To target hCas9 to the Ccl2 locus, a protospacer targeting the start codon of the Ccl2 coding sequence was generated using the following complementary oligonucleotides: sgMcp1-4_S: 5'-cacc G CTCTTCCTCCACCAC-CATGC-3' (SEQ ID NO: 26) and sgMcp1-4_AS: 5'-aaac GCATGGTGGTGGAGGAAGAG C-3' (SEQ ID NO: 27), where lower case bases were used to clone into BbsI-generated overhangs in the expression vector, and the guanine upstream of the protospacer was included to promote efficient transcription from the U6 promoter in the expression vector. To produce a single chimeric guide RNA (sgRNA) expression vector, complementary oligonucleotides containing the protospacer sequence were hybridized, phosphorylated, and cloned into an expression vector (Perez-Pinera et al., 2013a) (Addgene plasmid #47108) employing an human U6 promoter to drive expression of a chimeric *Streptococcus pyogenes* crRNA/tracrRNA sequence containing the aforementioned protospacer. The gRNA sequence was sgRNA_Ccl2-4: G CTCTTCCTC-CACCACCATGC (SEQ ID NO: 45).

Targeting vectors were produced in which coding sequences for each transgene (luciferase, sTNFR1-IgG, or Il1ra) were cloned directly in place of the start codon of Ccl2. The left homology arm was generated by PCR amplifying the region flanked by the following oligonucleotides from murine genomic DNA isolated using the DNeasy Blood & Tissue Kit (Qiagen): 5'-AAATTTCTTCTGCAC-CATGAG-3' (SEQ ID NO: 28) and 5'-CATGGTGGTG-GAGGAAGAGAGAGC-3' (SEQ ID NO:29). The right homology arm was similarly generated and defined by the following oligonucleotides: 5'-CAGGTCCCTGT-CATGCTTCTG-3' (SEQ ID NO: 30) and 5'-ATCTGG-GATGTGATCTTTGACA-3' (SEQ ID NO: 31). Targeting vectors were produced by isothermal assembly using pGL3-Basic (Promega) as a backbone. First, PCR fragments including transgenes followed by a Simian virus 40 polyadenylation signal sequence (SV40 polyA) were ligated to the left and right homology arms. Template for the Luciferase transgene was pGL3-Basic. The template for the sTNFR1-IgG transgene was a vector as previously described (Bloquel et al., (2004) Human Gene Therapy 15:189-201). The template for Il1ra was cDNA from murine C57Bl/6 mice. The resulting vectors were sequence confirmed, then an expression cassette comprised of the CMV promoter, the hygromycin B phosphotransferase coding sequence, and a bovine growth hormone polyA was cloned into each vector between the 3' end of the SV40 polyA following the transgene and the 5' end of the right homology arm.

Prior to transfection, iPSCs were trypsinized and subjected to a 30-minute feeder subtraction. Lipofectamine 2000 (Life Technologies) was used following manufacturer's instructions to co-transfect 800 ng of each sgRNA and 800 ng hCas9 along with 1.5 µg of the appropriate targeting vector into iPSCs freshly plated on MEFs in complete, antibiotic-free iPSC medium in a 6-well plate. The following day, cells were subjected to selection using 100 µg/ml of hygromycin B (Life Technologies). Transfected cells were subcultured on MEFs for 2 weeks prior to clonal isolation.

Clones were isolated either by iterative mechanical picking or by single-cell deposition. Single cell deposition was performed using a FACSVantage sorter (Becton Dickson). In preparation for single cell deposition, iPSCs were feeder subtracted prior to culture on 0.1% gelatin for 2 days. Cells were then trypsinized and subjected to a final feeder subtraction and then suspended in calcium- and magnesium-free PBS, 1 mM EDTA, 25 mM HEPES, and 1% FBS. Individual cells were then deposited into MEF-containing wells of a 96-well plate. Clones were sub-cultured on MEFs throughout the screening process. Targeted integration was assayed by performing junction PCR using the oligonucleotides listed in Table 1 for each target. For the PCR, a subset of each clone was lysed using QuickExtract (Epicentre) according to the manufacturer's instructions. The cell lysate was then diluted 8-10 fold prior to use as template in a PCR using Q5 polymerase (NEB) according to manufacturer's instruction with the following cycling parameters: 98/30"|98/8";68/10";72/20"|×35;72/2'. Clones exhibiting unique and specific product from the junction PCR were propagated on MEFs and until further differentiation. Further analysis of targeting of the Ccl2 alleles in these clones were performed using the following oligonucleotide pair: Surv MCP1 F1: 5'-tcccaggagtggctagaaaa-3' (SEQ ID NO: 32); Surv MCP1 R1: 5'-ccacgacaattcaaaaatgg-3' (SEQ ID NO: 33).

TABLE 2

Primer pairs used in junction PCR to determine the presence of targeted integration events on Ccl2 alleles.

| Target | | SEQ ID NO: |
|---|---|---|
| | Forward Primer | |
| IL1ra | 5'-TCAGCTGCCTGATCTGAGAA-3' | 34 |
| Firefly Luciferase | 5'-TCAGCTGCCTGATCTGAGAA-3' | 34 |
| sTNFR1-IgG | 5'-TCAGCTGCCTGATCTGAGAA-3' | 34 |

TABLE 2-continued

Primer pairs used in junction PCR to determine the presence of targeted integration events on Ccl2 alleles.

| Target | Reverse Primer | SEQ ID NO: |
|---|---|---|
| IL1ra | 5'-AGGTCAATAGGCACCATGTCTA-3' | 35 |
| Firefly Luciferase | 5'-CAGCGTAAGTGATGTCCACCT-3' | 36 |
| sTNFR1-IgG | 5'-CACTCCCTGCAGTCCGTATC-3' | 37 |

Micromass Pre-Differentiation Culture.

Induced pluripotent stem cells were subjected to a 15-day, high-density micromass culture to achieve differentiation toward a mesenchymal state. Cells were cultured in serum-free differentiation medium consisting of high glucose DMEM, NEAA, 2-ME, ITS+(insulin, transferrin, selenium) premix supplement (BD), 25 ng/ml gentamicin, 50 µg/ml L-ascorbic acid-phosphate, and 40 µg/ml L-proline. On days 3-5 only, medium was supplemented with 100 nM dexamethasone (Sigma) and 50 ng/ml murine BMP-4 (R&D Systems). Micromasses were dissociated on day 15 with pronase and type II collagenase in order to attain a single cell suspension. Dissociated cells were plated in monolayer on gelatinized vessels and cultured in differentiation medium supplemented with 4 ng/ml bFGF (Roche) and 10% FBS. Cells were subsequently utilized in monolayer to probe the dynamical response of engineered cells to IL-1 or TNF treatment. Additionally, cells were used to derive engineered cartilage in order to evaluate the utility of these cells as a source for inflammation-protected tissue regeneration.

NF-κB activity assay. A lentiviral construct containing 4 putative NF-κB response elements upstream of firefly luciferase was generated by cloning the following sequence: 5'-CGGGAAATTCCGCTAGCACTAGTGGGACTTTCC-CACTAGTGGGAAATTAGCCCGGG ACTTTCCCGTCTCCTCGAGGGGACTTCCCA-3' (SEQ ID NO: 40) upstream of the minimal CMV promoter in pGL3Basic (Promega) and then sub-cloning the cassette including the luciferase transgene into a lentiviral expression vector. Additionally, an NF-κB negative regulatory element (NRE-5'-AATTCCTCTGA-3' (SEQ ID NO: 41)) (Nourbakhsh et al., (1993) EMBO J 12:451-459) was cloned upstream of the response elements in order to reduce background signal from the luciferase vector. Lentivirus was generated by co-transfecting 2 µg of the cloned transfer vector, 1.5 µg of psPAX2 (Addgene 12260) and 0.6 µg of pMD2G (Addgene 12259) into 293T cells cultured at confluence in the well of a 6-well plate using Lipofectamine 2000. The next day, medium from 293T lentivirus producer cells was changed and conditioned medium containing lentivirus was collected approximately 36 and 60 hours after transfection. The lentiviral supernatant was filtered through 0.45 um cellulose acetate filters and stored at −80° C. until use.

Pre-differentiated cells were transduced by supplementing culture medium 1:1 with viral supernatant as well as 4 µg/ml polybrene and incubating the cells in the presence of the virus overnight. Transduced cells were expanded, passaged, and then treated with IL-1. At the indicated time points, samples were lysed and assayed for luminescence using a Bright Glo (Promega) luminescence kit according to manufacturer's instructions. Luminescence normalized to background levels of no cytokine treatment was used to report induction of NF-κB transcriptional activity.

Chondrogenesis in Aggregate Culture System.

Multiple chondrogenesis experiments were performed using slightly varying experimental conditions. Each experiment comprised of matched controls cultured under the same conditions (e.g., passage number, starting cell number per sample, length of cartilage maturation period). Passage 2-3 pre-differentiated cells were trypsinized and resuspended in differentiation medium supplemented with 100 nM dexamethasone and 10 ng/ml TGF-β3 (R&D Systems) at a density of 1e6 cells/ml. Aggregate cultures were produced by placing cells in wells a u-bottom 96-well plate (125,000-250,000 cells per well, depending on the experiment) or in 15 ml conical tubes (500,000 cells per tube). Cells were pelleted by centrifugation at 200×g and cultured for three to four weeks prior to treatment with cytokine (0, 0.1-1 ng/ml IL-1α, or 20 ng/ml TNF-α) in the absence of dexamethasone and TGF-β3. Three days later, aggregate cultures and culture supernatant samples were harvested for gene expression, biochemical, and histological analyses.

Biochemical Analyses of Engineered Cartilage.

Samples used for biochemical analyses were harvested, rinsed with DPBS, and stored at −20° C. until testing. Aggregate culture samples were digested in papain (125 µg/ml; Sigma) at 65° C. overnight. Digested samples were then analyzed using the picogreen assay (Life Technologies) to measure double-stranded DNA, the ortho-hydroxyproline assay (Woessner, (1961) Arch. Biochem. Biophys. 93:440-447) for measuring total collagen content, and the dimethylmethylene blue assay (Farndale et al., (1986) Biochim. Biophys. Acta 883:173-177) for measuring the total sulfated glycosaminoglycan content of tissues (n=3-6 per group).

Gene expression. Samples for gene expression analysis were rinsed in DPBS, lysed in cell lysis reagent (Norgen Biotek) and frozen at −80° C. until further processing. Total RNA was isolated per manufacturer's recommendations (Norgen Biotek). Engineered cartilage samples were first homogenized with a pestle. Reverse transcription was performed using the superscript VILO cDNA synthesis kit (Life Technologies) per manufacturer's instructions. Quantitative RT-PCR was performed with n=3-4 samples per group on a StepOnePlus using Power Sybr (Applied Biosystems, Inc.) per manufacturer's instructions. Fold changes were determined relative to a reference group cultured without IL-1α and by using 18s rRNA as a reference gene. Gene expression was probed using the primer pairs listed in Table 3.

TABLE 3

Primer pairs used in qRT-PCR gene expression assays

| Target | Forward Primer | SEQ ID NO: |
|---|---|---|
| r18s | 5'-CGGCTACCACATCCAAGGAA-3' | 6 |
| Acan | 5'-GCATGAGAGAGGCGAATGGA-3' | 7 |
| Adamts4 | 5'-GACCTTCCGTGAAGAGCAGTGT-3' | 8 |
| Adamts5 | 5'-GCCCACCCAATGGTAAATCTTT-3' | 9 |

TABLE 3-continued

Primer pairs used in qRT-PCR gene expression assays

| Target | | SEQ ID NO: |
|---|---|---|
| Ccl2 | 5'-GGCTCAGCCAGATGCAGTTAA-3' | 10 |
| Col2a1 | 5'-TCCAGATGACTTTCCTCCGTCTA-3' | 11 |
| IL1rn | 5'-GTCCAGGATGGTTCCTCTGC-3' | 40 |
| IL6 | 5'-GAGGATACCACTCCCAACAGACC-3' | 13 |
| Mmp9 | 5'-CGAACTTCGACACTGACAAGAAGT-3' | 14 |
| Mmp13 | 5'-GGGCTCTGAATGGTTATGACATTC-3' | 15 |
| sTNFR1 | 5'-ATTGGACTGGTCCCTCACCT-3' | 41 |
| Reverse Primer | | |
| r18s | 5'-GGGCCTCGAAAGAGTCCTGT-3' | 16 |
| Acan | 5'-CTGATCTCGTAGCGATCTTTCTTCT-3' | 17 |
| Adamts4 | 5'-CCTGGCAGGTGAGTTTGCAT-3' | 18 |
| Adamts5 | 5'-TGACTCCTTTTGCATCAGACTGA-3' | 19 |
| Ccl2 | 5'-CCTACTCATTGGGATCATCTTGCT-3' | 20 |
| Col2a1 | 5'-AGGTAGGCGATGCTGTTCTTACA-3' | 21 |
| IL1rn | 5'-TCTTCCGGTGTGTTGGTGAG-3' | 42 |
| IL6 | 5'-AAGTGCATCATCGTTGTTCATACA-3' | 23 |
| Mmp9 | 5'-GCACGCTGGAATGATCTAAGC-3' | 24 |
| Mmp13 | 5'-AGCGCTCAGTCTCTTCACCTCTT-3' | 25 |
| sTNFR1 | 5'-CACTCCCTGCAGTCCGTATC-3' | 37 |

Enzyme-Linked Immunosorbent Assays.

Media samples used in ELISAs were collected from wells and stored at −20° C. or −80° C. until used. Reagents for ELISAs were purchased from R&D and used according to manufacturer's recommendations.

Histological Processing.

Samples for histology were rinsed in DPBS upon harvest, fixed in 4% paraformaldehyde for 24 hours, paraffin embedded, and sectioned at 10 μm thickness. Samples were stained with Safranin-O/fast green/hematoxylin using standard protocols.

Statistical Analysis.

Statistical analysis was performed in the Statistica 7 software package using ANOVA with Fisher's protected least significance difference post-hoc test with α=0.05. For qRT-PCR comparisons, fold change values were log-transformed prior to statistical analysis. Average group values and standard errors of the means were calculated in the logarithmic space prior to transforming data to linear values for reporting fold changes.

Example 5

Clonal Isolation and Screening

Figure 10:
FIG. 10 shows ethidium bromide-stained agarose gel demonstrating the result of junction PCR probing for targeted integration of transgenes to the Ccl2 locus. Numbers after abbreviations indicate clone number (e.g., sTNFR23=clone 23 in which the sTNFR1 transgene was targeted to Ccl2). In each reaction, wild-type (WT), Ccl2-Il1ra, Ccl2-Luc, or Ccl2-sTNFR1 genomic DNA was used as a template. A 2 Log Ladder (NEB) was run along with samples and is shown in the right-most lane.

The goal was to reprogram iPSCs with the capacity to respond to an inflammatory transcription stimulant with potent and autonomously regulated anti-cytokine production (FIG. 9). As such, transgenes encoding a firefly luciferase transcriptional reporter or a cytokine antagonist, either Il1ra or sTNFR1-IgG, were targeted to the Ccl2 locus using the CRISPR/Cas9 gene editing platform. After hygromycin selection and junction PCR screening, multiple clones were identified to possess targeted integration events at the Ccl2 locus. For the luciferase transgene, 2 out of 11 clones initially screened after mechanical isolation displayed evidence of targeted integration. Afterwards, one of these clones was subcloned, and 6 out of 10 subclones displayed clear evidence of targeted integration (2 of these are displayed in FIG. 10). For Il1ra, 4 out of 34 clones were positive and for sTNFR1-IgG, 3 out of 44 possessed the targeted integration event (FIG. 10). Subsequent PCR analyses were performed to probe whether one or both Ccl2 alleles were targeted in these clones of interest. In all cases, only one allele contained the targeted integration event. Furthermore, Sanger sequencing was performed on PCR products to determine whether the remaining Ccl2 allele lacking targeted integration was disrupted by CRISPR/Cas9 at the start codon. At least one clone for each transgene group (luciferase, Il1ra, and sTNFR-IgG) was identified with an intact Ccl2 start codon.

Example 6

Characterization of Responsiveness

Figure 11A:
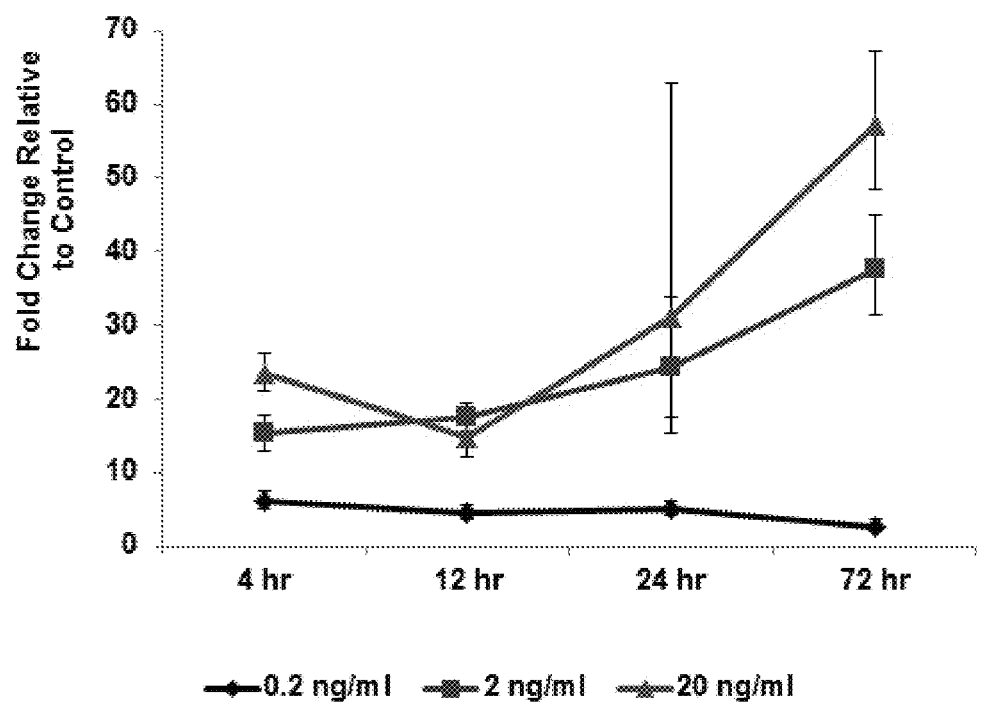
FIG. 11A shows Ccl2 gene expression profile from Wild-type cells. qRT-PCR data showing the expression profile of Ccl2 after treatment of WT cells with various concentrations of TNF-α (n=3).

Clones of interest (referred to as Ccl2-Luc, Ccl2-Il1ra, or Ccl2-sTNFR1 lines as appropriate for each integrated transgene) were culture expanded on MEFs and then pre-differentiated in micromass culture. First, whether targeted transgene at the Ccl2 start codon would enable cytokine-inducible transgene expression was evaluated. As a point of reference, wild-type (WT) cells were treated with a range of TNF-α concentrations (0.2-20 ng/ml), and mRNA samples were collected at 4, 12, 24, and 72 hours (FIG. 11A). Ccl2 gene expression was evaluated by qRT-PCR. At all TNF-α concentrations tested, Ccl2 gene expression was elevated at each time point. In the 2 and 20 ng/ml groups, Ccl2 gene expression continued to increase through the 72 hour TNF-α treatment window.

Figure 11B:
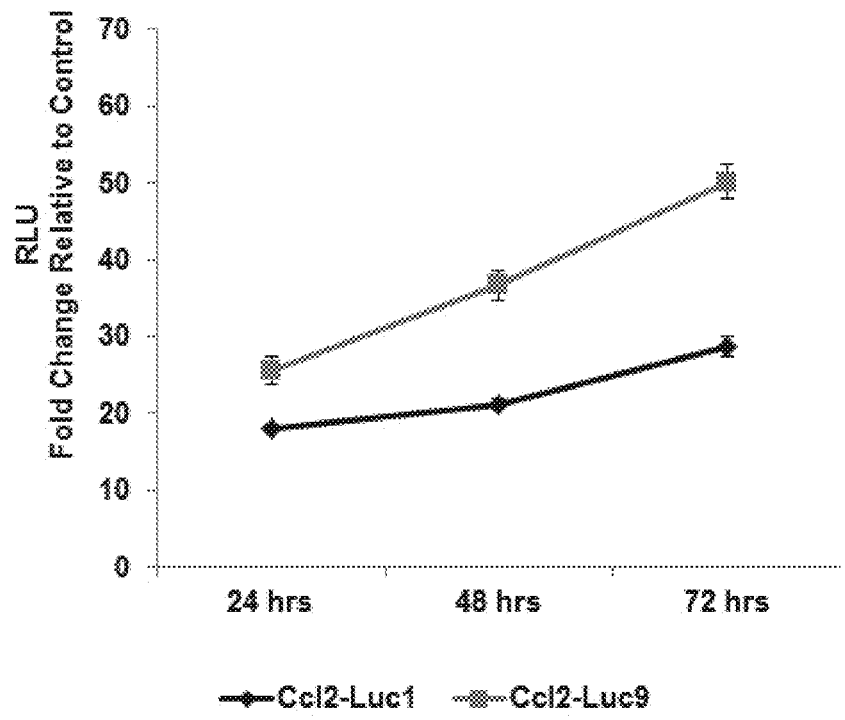
FIG. 11B shows cytokine-induced expression of luciferase from endogenous Ccl2 Locus (20 ng/mL TNF). Two cell lines were engineered to express luciferase from the endogenous Ccl2 locus and were then stimulated with 20 ng/ml of TNF-α. Cells were lysed at the indicated time after TNF treatment and luminescence was measured as a readout for Ccl2-driven transgene expression (n=6).

Next, using two Ccl2-luciferase cell lines, luciferase expression was induced by stimulating cells with 20 ng/ml TNF-α to evaluate whether transgene expression reflected endogenous Ccl2 expression in WT cells. Relative luminescence measurements indicated that transgene expression in both clones was indeed stimulated by cytokine and increased across the 72-hour TNF-α treatment period (FIG. 11B), consistent with findings from TNF-induced Ccl2 expression in WT cells.

The responsiveness of the engineered cells endowed with Ccl2-driven anti-cytokine transgenes as probed. The experiments were performed by evaluating gene expression and transgene production in the Ccl2-sTNFR1 group, as lack of this human transcript and protein in the murine cell populations would allow for direct conclusions regarding production from the Ccl2 locus, whereas murine Il1ra can be produced from its own endogenous gene as well as the Ccl2 locus in the engineered cells.

Initially, a time course and dose response experiment were performed, in which Ccl2-sTNFR1 and wild-type cells were treated with a range of TNF-α concentrations (0.2-20 ng/ml) for a variety of times (4, 12, 24, and 72 hours). The responsiveness of the engineered cells was evaluated by measuring the expression of the sTNFR1 transgene at both the mRNA and protein levels by qRT-PCR and ELISA, respectively. Furthermore, the expression of Il6 at the mRNA level by qRT-PCR was measured to characterize the state of inflammation the WT and engineered Ccl2-sTNFR1 cells experienced.

Figure 12A:
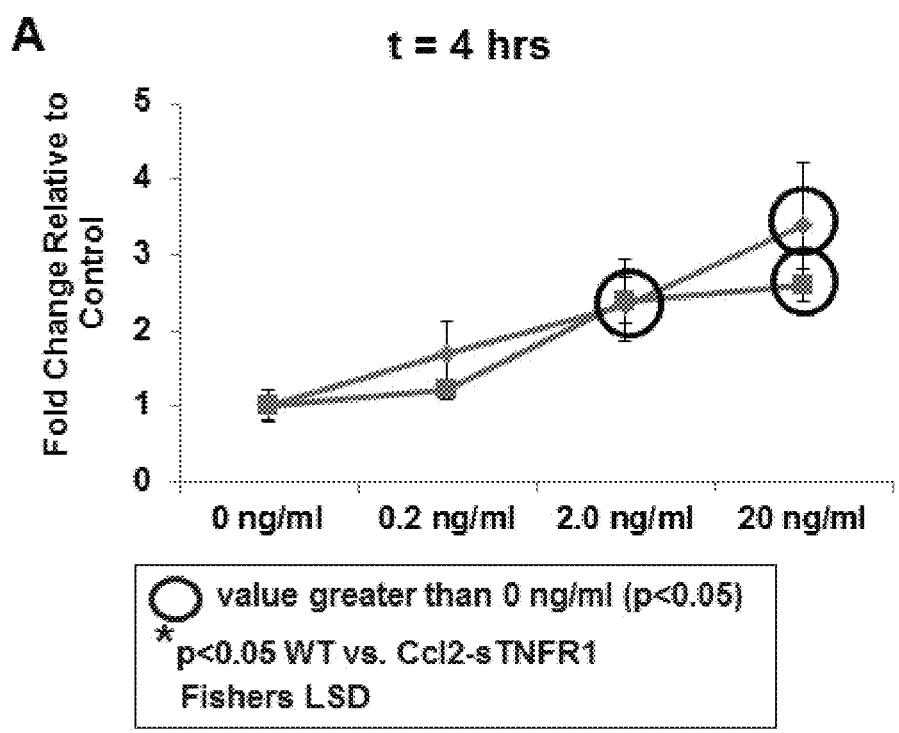
FIGS. 12A-12D show the profile of Il6 expression in response to various doses (X-axes) of TNF and across the indicated time points of 4 hrs (FIG. 12A), 12 hrs (FIG. 12B), 24 hrs (FIG. 12C), and 72 hrs (FIG. 12D). Values plotted represent the mean fold change in expression±SEM (n=3) as compared to matched cells of the same genotype treated with 0 ng/ml TNF and as normalized by the r18S reference gene.
Figure 12B:
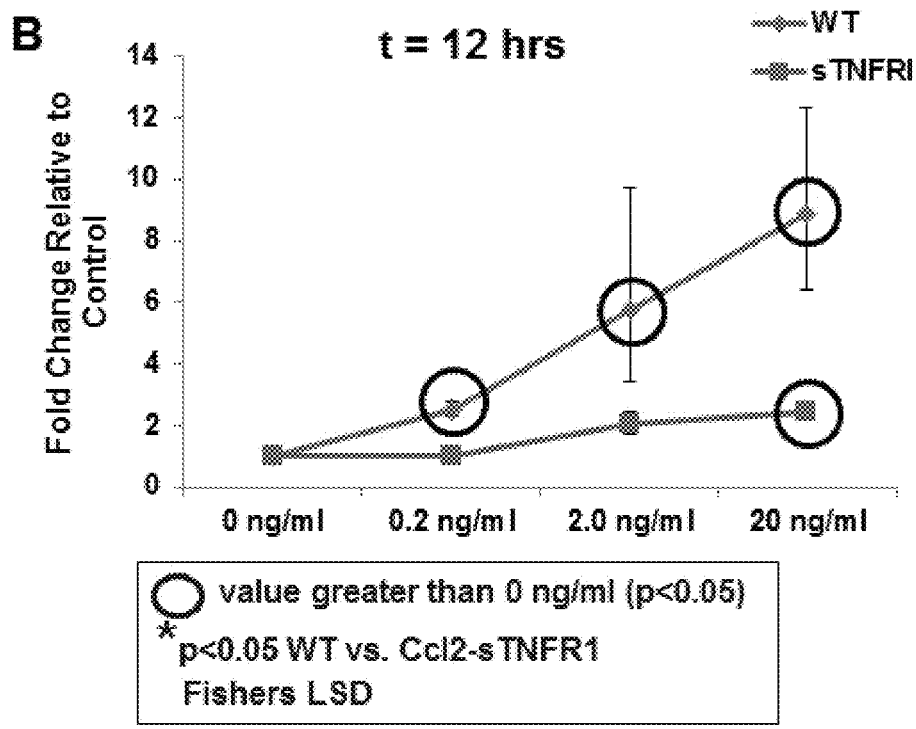
Figure 12C:
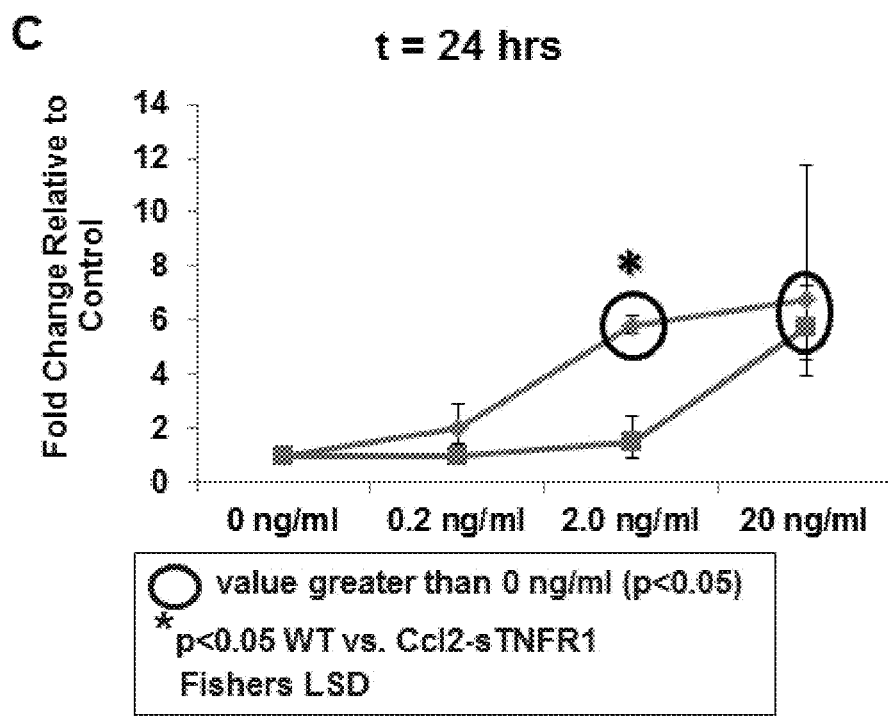
Figure 12D:
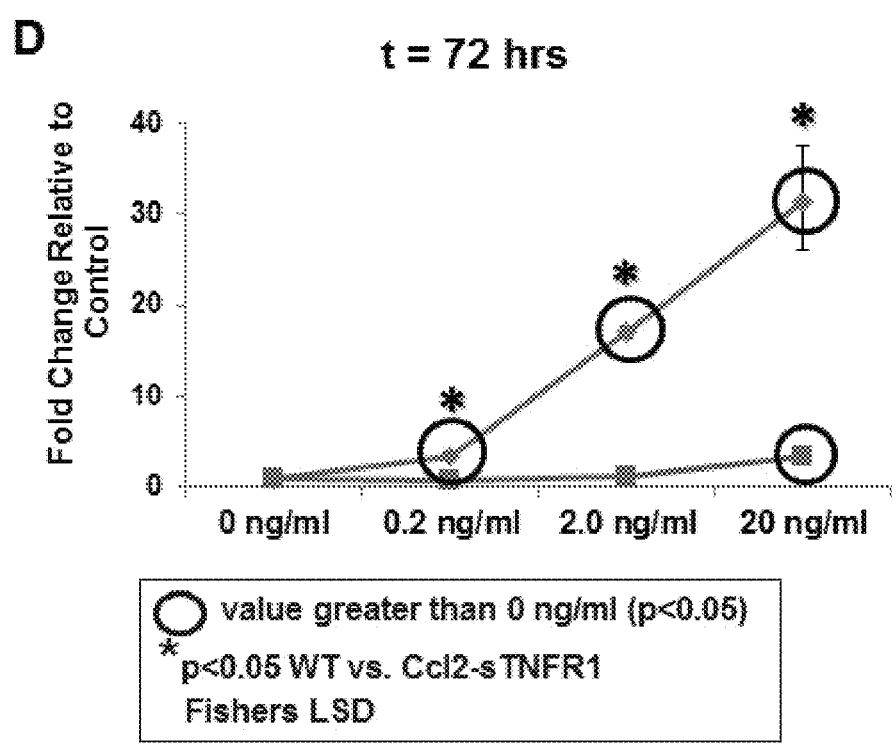

As early as 4 hours after TNF-α treatment, the 2 and 20 ng/ml treatments resulted in significant upregulation of Il6 transcription in both the WT and Ccl2-sTNFR1 cells, while 0.2 ng/ml did not render significant upregulation (FIG. 12A). At the 12 hour time point, Il6 expression was significantly elevated at all TNF-α concentrations in WT cells; however, Il6 was only significantly upregulated in the Ccl2-sTNFR1 engineered cells at the 20 ng/ml level of TNF-α treatment (FIG. 12B). Even at the 20 ng/ml level of treatment, engineered cells showed a significantly lower level of Il6 induction than WT cells. At the 24 hour time point, the medium and high concentrations of TNF-α drove an upregulation of Il6 in WT cells, but only the high 20 ng/ml concentration resulted in significant upregulation of Il6 in the sTNFR1 engineered cells (FIG. 12C). By the 72 hour time point, all three doses of TNF-α resulted in significant upregulation of Il6 in the WT cells, while TNF-α treatment only induced an upregulation of Il6 in the Ccl2-sTNFR1 cells at the 20 ng/ml treatment level (FIG. 12D).

Figure 13A:
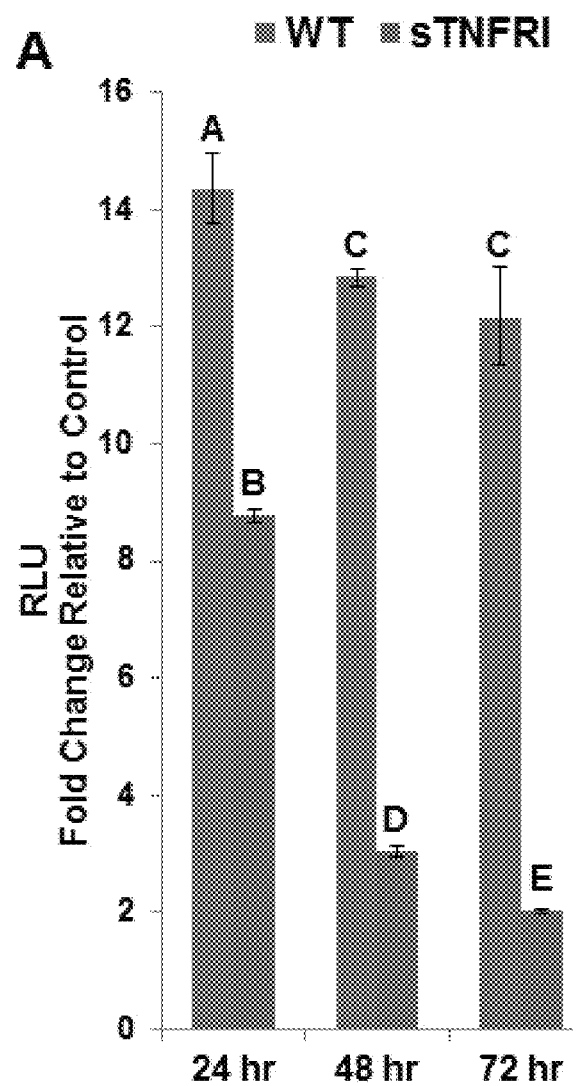
FIG. 13A shows fold change in NF-κB transcriptional activity as measured by the luminescence signal from NF-κB-dependent firefly luciferase expression. Bars represent the mean fold change in relative luminescence units (RLU)±SEM of cells treated with 20 ng/ml TNF-α for the indicated time as compared to controls cultured with 0 ng/ml TNF-α (n=4-6).

To evaluate whether the observations of Il6 gene expression reflect the general state of inflammation in these cells, WT and Ccl2-sTNFR1 cells were transduced with a lentiviral vector delivering an NF-κB luminescence reporter. These cells were treated with 0 or 20 ng/ml TNF-α and after 24, 48, and 72 hours, lysed cells to measure luminescence as an output for NF-κB transcriptional activity. At the 24 hour time point, the NF-κB transcriptional activity was upregulated in both WT and Ccl2-sTNFR1 cells. However, at the 48 and 72 hour time points, a sharp decline in NF-κB transcriptional activity was observed in engineered cells expressing sTNFR1 under control of the Ccl2 locus (FIG. 13A). Taken together with the Il6 mRNA qRT-PCR results, these data indicate that the Ccl2-sTNFR1 cells are capable of attenuating the TNF-α-induced regulation of Il6 as well as a more general inflammatory state. Furthermore, these results suggest that, after three days of TNF-α treatment, the cells are capable of antagonizing even a high (20 ng/ml) concentration of TNF-α, while control WT cells remain in a state of inflammation even after treatment with only 0.2 ng/ml TNF-α.

Figure 13B:
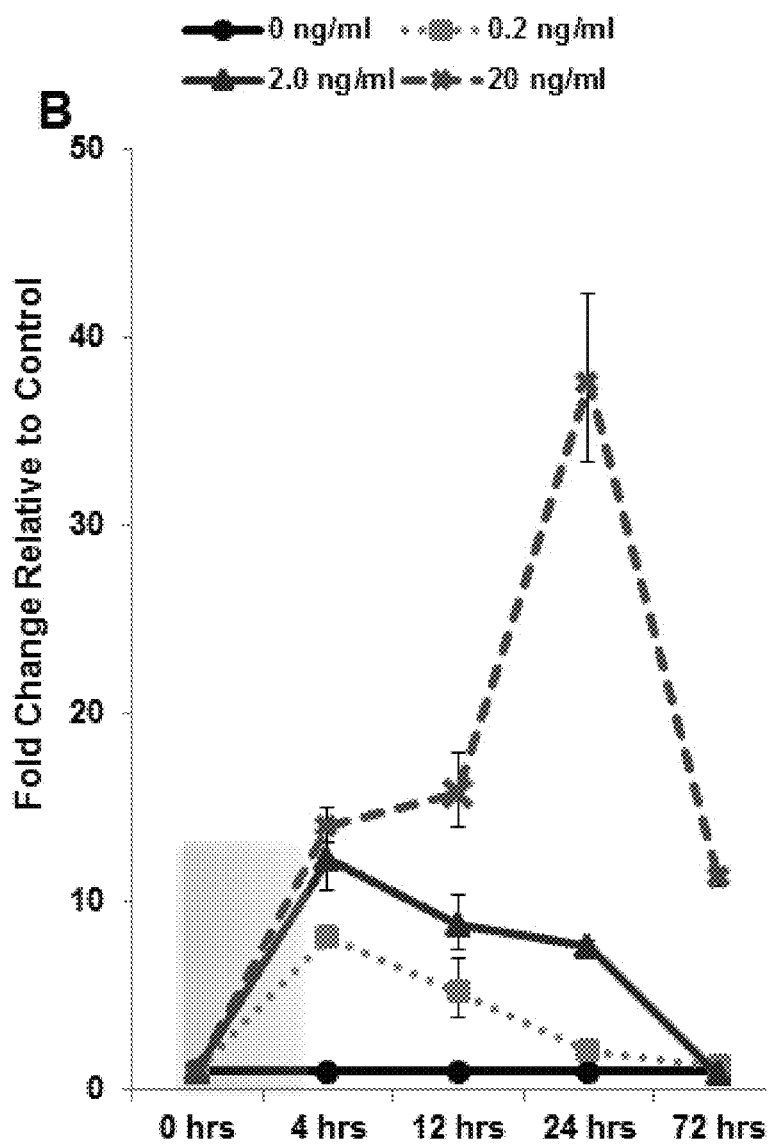
FIG. 13B shows changes in Ccl2-driven expression of the sTNFR1 transgene over time as measured by qRT-PCR. Values plotted represent the mean fold change in expression±SEM (n=3) as compared to matched cells of the same genotype treated with 0 ng/ml TNF-α and as normalized by the r18S reference gene. The 0 hr time point (shaded) was not measured and is shown for illustration purposes only, as all samples at 0 hrs measure 1 by definition.
Figure 13C:
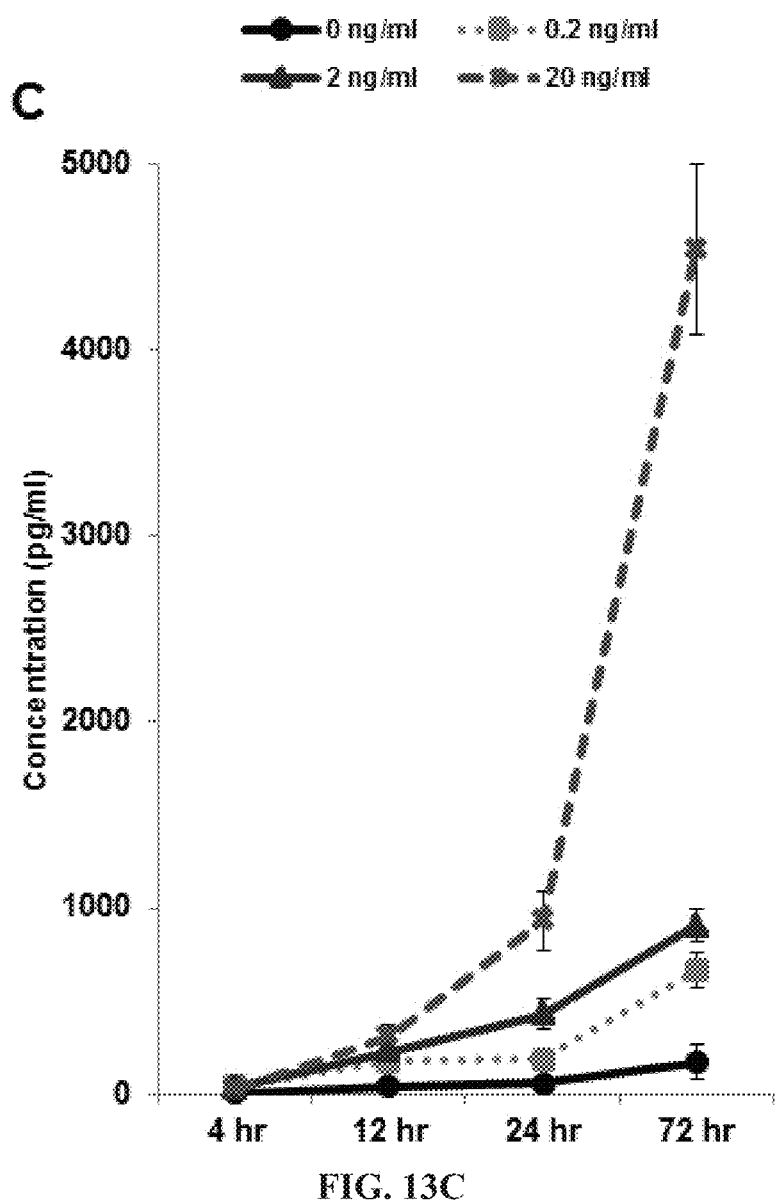
FIG. 13C shows ELISA data showing the concentration of sTNFR1 protein in culture media in samples treated with the indicated concentrations of TNF-α. Samples were collected at the indicated time. Values represent mean±SEM (n=3).

To ascertain whether this attenuation could be mediated by cytokine-inducible production of the TNF-α antagonist sTNFR1 from the engineered cells, the expression of sTNFR1 transgene was measured in parallel with Il6 expression. sTNFR1 expression was rapidly upregulated at the 4 hour time point (FIG. 13B). In the groups treated with 0.2 and 2 ng/ml of TNF-α, transgene expression began to decline between the 4 and 12 hour time points, in accordance with the decreased Il6 expression (FIG. 12A, FIG. 12B). This transition likely reflects an attenuated state of inflammation after low and medium treatment of TNF-α. Ccl2-driven sTNFR1 expression continued to increase through the 24 hour time point at the high TNF-α treatment, but this level declined rapidly toward baseline values at the 72 hour time point, consistent with the persistent state of inflammation at 24 hours that largely resolved by 72 hours as suggested by the Il6 and NF-κB transcription data FIG. 12C, FIG. 12D and FIG. 13A). In accordance with these qRT-PCR data, increased accumulation of sTNFR1 was measured in culture media over time in a dose-dependent fashion (FIG. 13C).

From this, even a low concentration of TNF-α is capable of inducing sTNFR1 expression, indicating that low in vitro doses of TNF-α can induce transgene expression in the engineered cell population. This suggests that cells remain attuned to low levels of TNF-α in the microenvironment, indicating that basal expression of sTNFR1 does not abolish the cell's ability to detect low concentrations of the cytokine. These data also demonstrate that the engineered cells are capable of modulating therapeutic output of sTNFR1 in a cytokine dose-dependent manner, spanning a dynamic range across at least three orders of magnitude. Furthermore, the anti-cytokine therapy appears to be auto-regulated, as expression of sTNFR1 mRNA declined as the inflammatory state of the engineered cells resolved in response to sTNFR1 production.

Figure 14A:
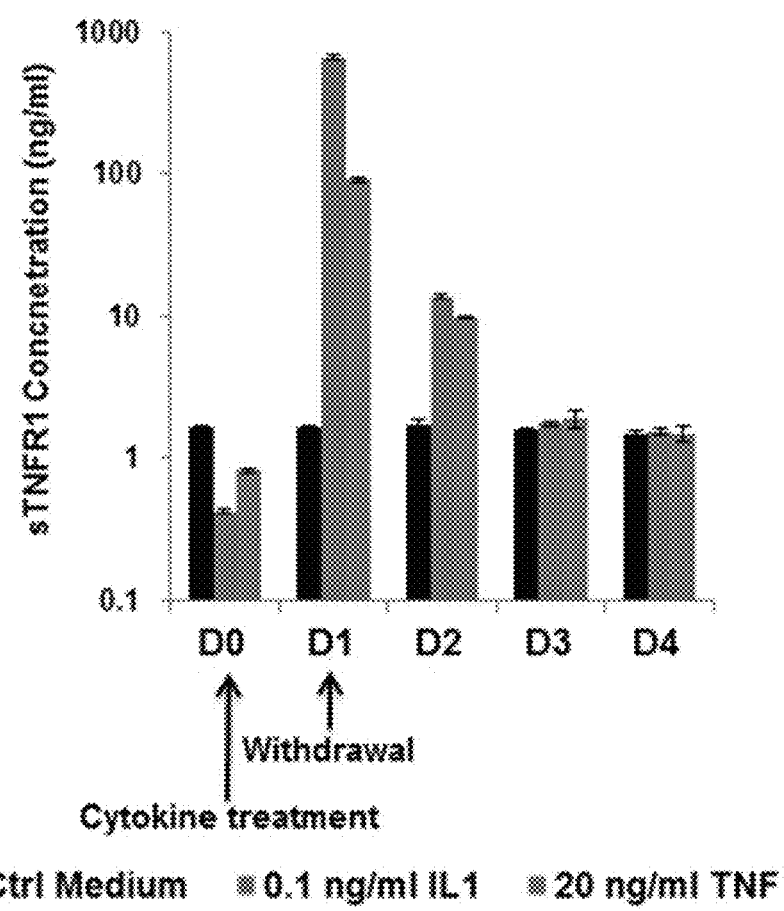
FIGS. 14A-14C show ELISA measurement of transgene product measured in culture media sampled at various 24-hour intervals relative to treatment with no cytokine, 0.1 ng/ml IL-1, or 20 ng/ml TNF.
Figure 14B:
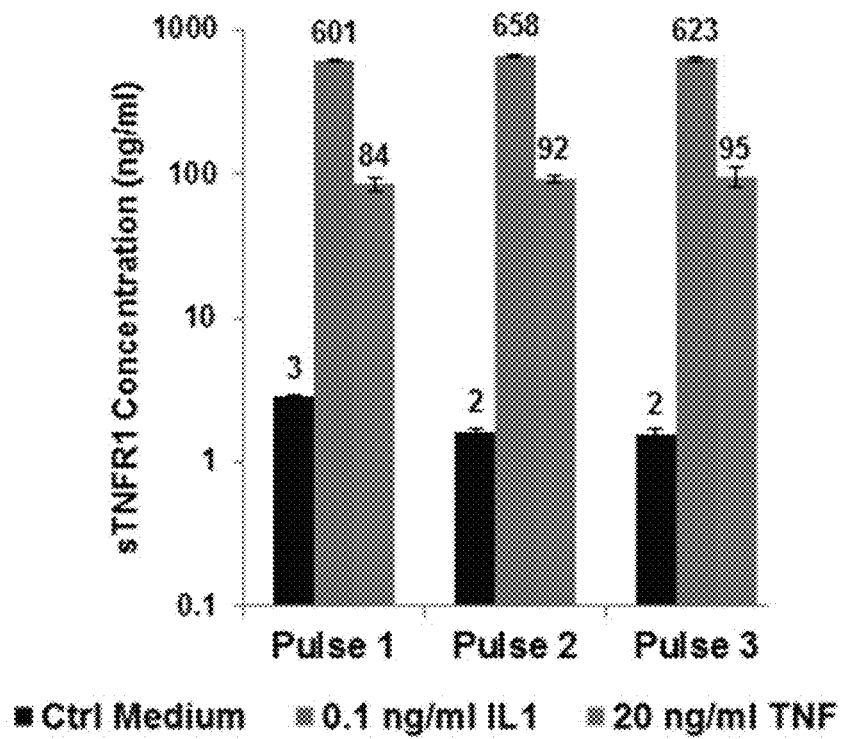

As a follow-up to these analyses, iterative stimulation of Ccl2-driven sTNFR1 and Il1ra cells in monolayer were performed with either 0 ng/ml cytokine, 0.1 ng/ml IL-1α or 20 ng/ml TNF-α. After 24 hours, the cytokine-containing medium was exchanged for cytokine-free medium, and samples were collected. Three days later, cells were stimulated with cytokine again to establish the capacity of the cells to respond to recurrent stimulation with cytokine. sTNFR1-engineered cells displayed a basal level of production of less than 3 ng/ml (FIG. 14A, FIG. 14B). Engineered cells displayed the capacity to rapidly secrete sTNFR1 after either IL-1α or TNF-α stimulation (FIG. 14A).

Withdrawal of cytokine-containing medium resulted in a rapid decline in sTNFR1 accumulation over subsequent collection periods, irrespective of whether IL-1α or TNF-α served as the stimulant. In both cases, production of sTNFR1 decreased to basal levels within 48 hours of removing cytokines (FIG. 14A).

Figure 14C:
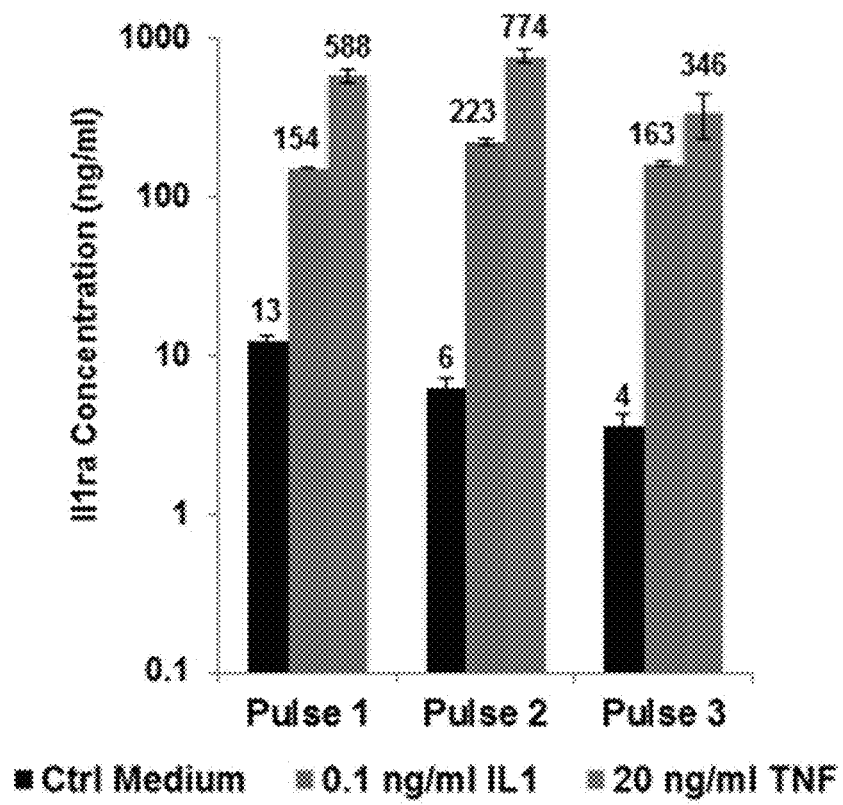
Figure 15A:
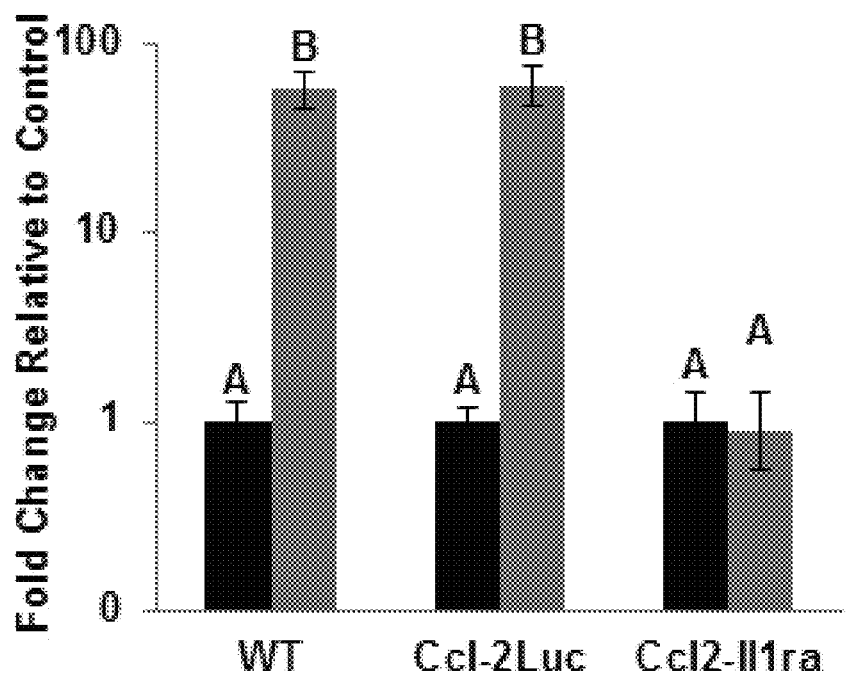
FIGS. 15A-15H show relative gene expression data for Ccl2 (FIG. 15A), Il6 (FIG. 15B), Adamts4 (FIG. 15C), Adamts5 (FIG. 15D), Mmp9 (FIG. 15E), Mmp13 (FIG. 15F), Acan (FIG. 15G), and Col2a1 (FIG. 15H) as measured by qRT-PCR to examine the effects of 1 ng/ml IL-1 treatment on engineered cartilage derived from either WT, Ccl2-Il1ra, Ccl2-Luc, or Ccl2-sTNFR1 cells. Fold changes were determined relative to a reference group cultured without IL-1α and by using 18s rRNA as a reference gene. Bars represent group means of fold change±SEM (n=3). Groups not sharing the same letter are statistically different (p<0.05). Notation of n.s. implies no significance for the evaluated gene.
Figure 15B:
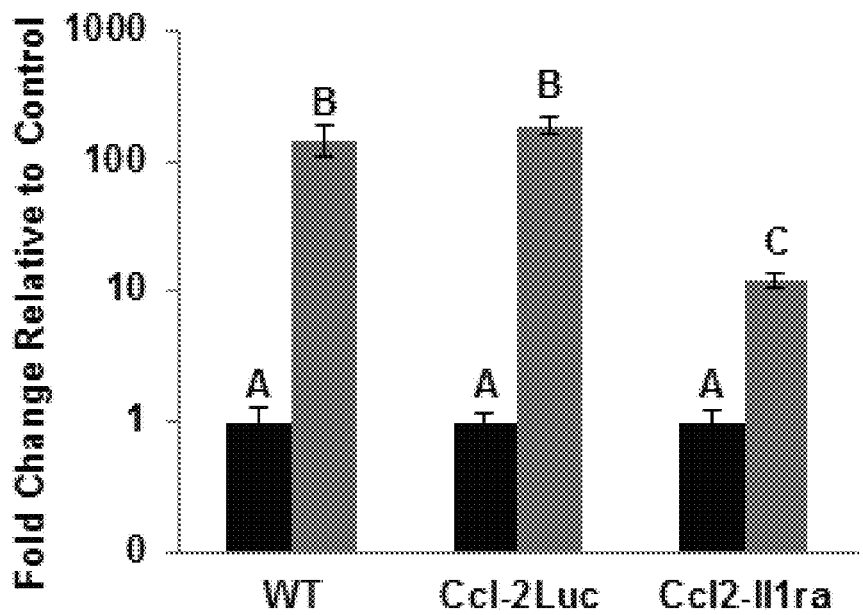
Figure 15C:
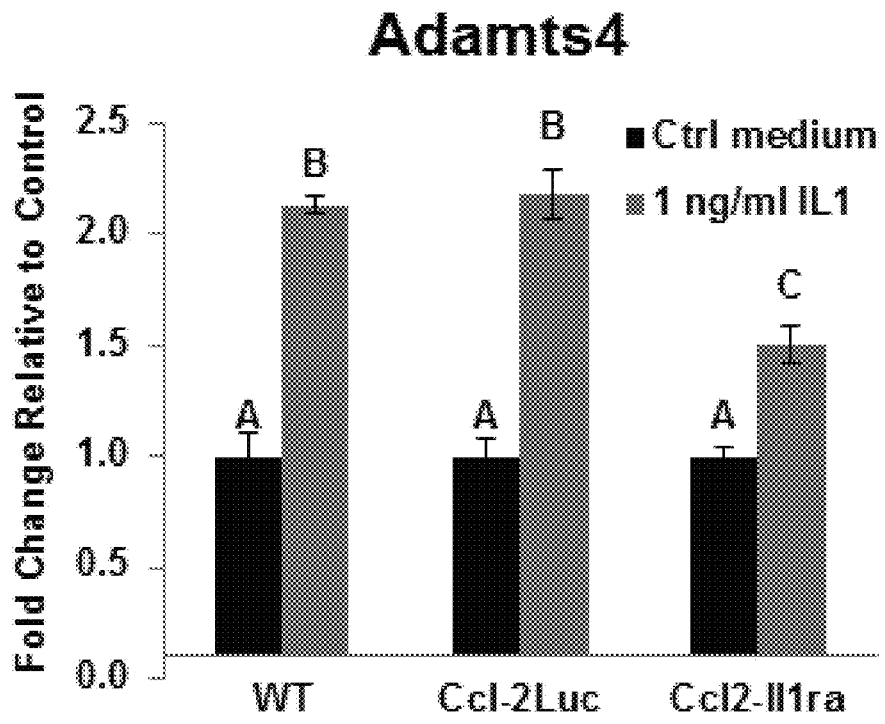
Figure 15D:
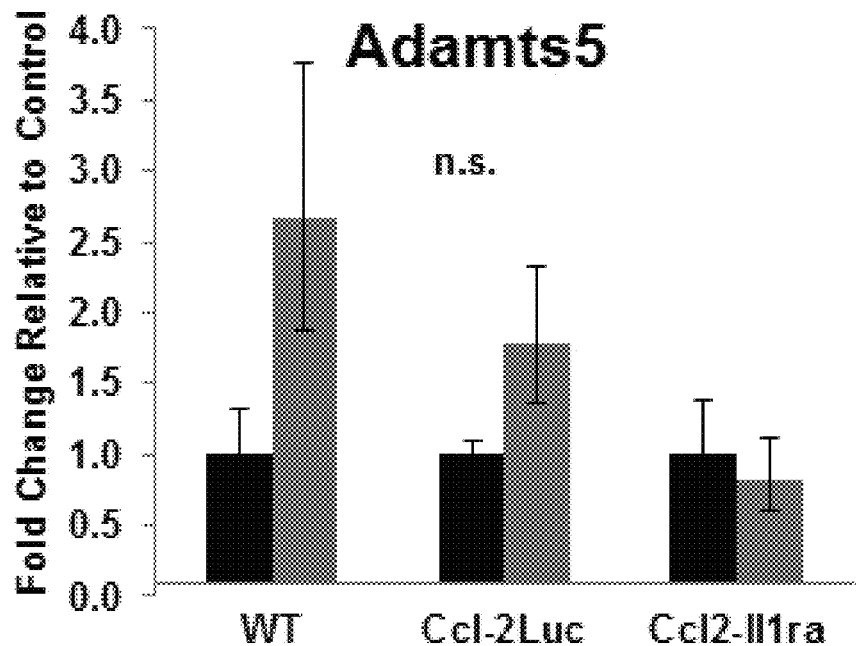
Figure 15E:
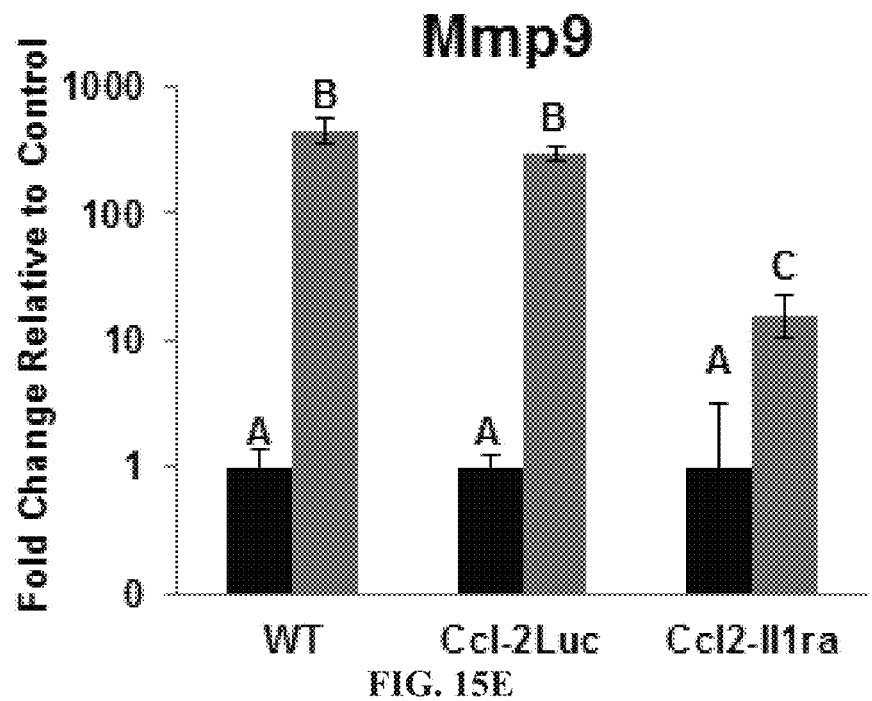
Figure 15F:
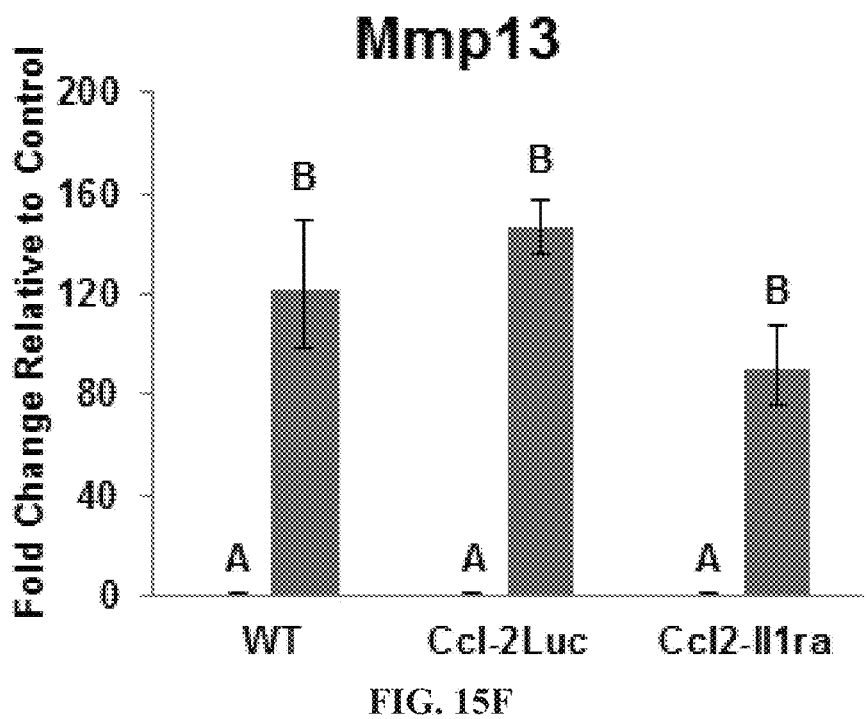
Figure 15G:
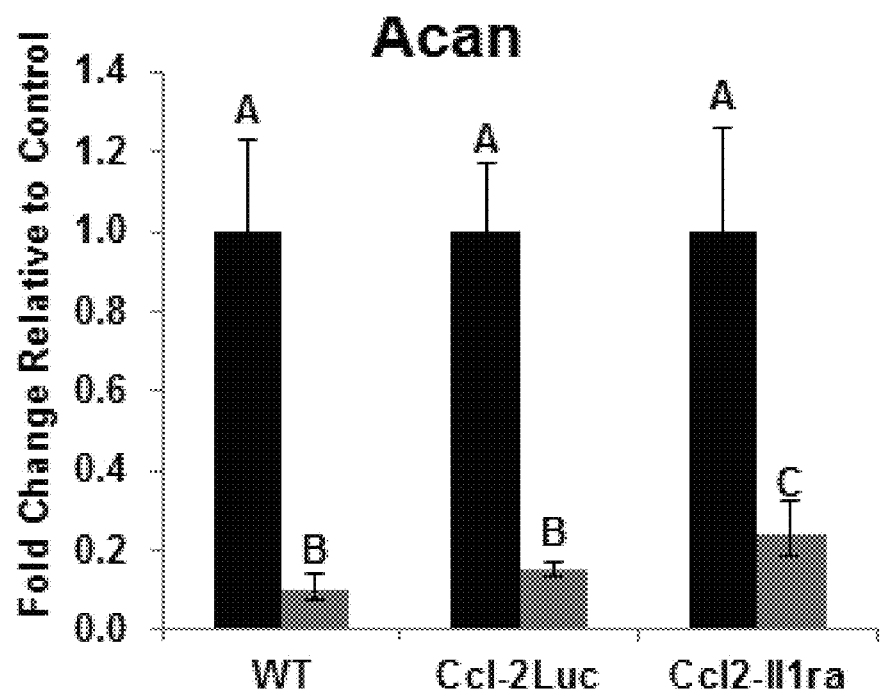
Figure 15H:
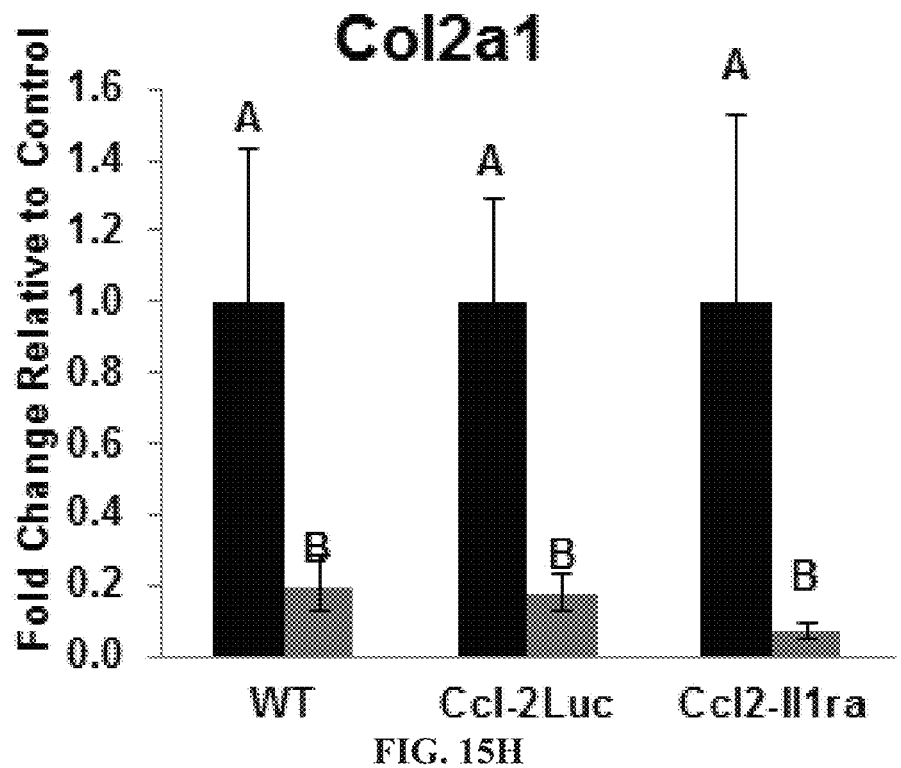
Figure 16A:
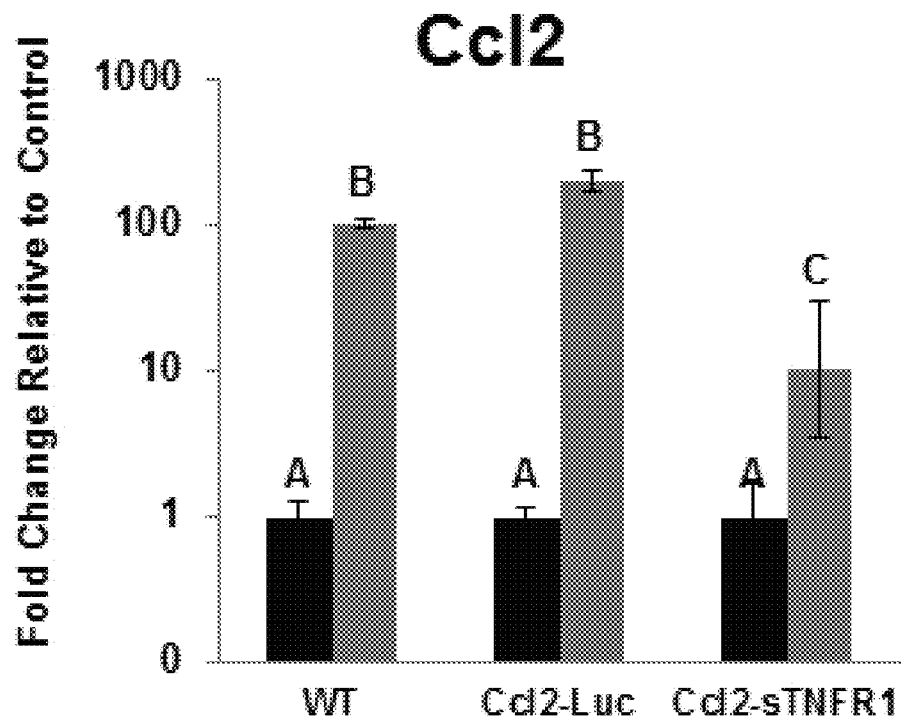
FIGS. 16A-16H show relative gene expression data for Ccl2 (FIG. 16A), Il6 (FIG. 16B), Adamts4 (FIG. 16C), Adamts5 (FIG. 16D), Mmp9 (FIG. 16E), Mmp13 (FIG. 16F), Acan (FIG. 16G), and Col2a1 (FIG. 16H) as measured by qRT-PCR to examine the effects of 20 ng/ml TNF treatment on engineered cartilage derived from either WT, Ccl2-Luc, or Ccl2-sTNFR1 cells. Fold changes were determined relative to a reference group cultured without IL-1α and by using 18s rRNA as a reference gene. Bars represent group means of fold change±SEM (n=3). Groups not sharing the same letter are statistically different (p<0.05).
Figure 16B:
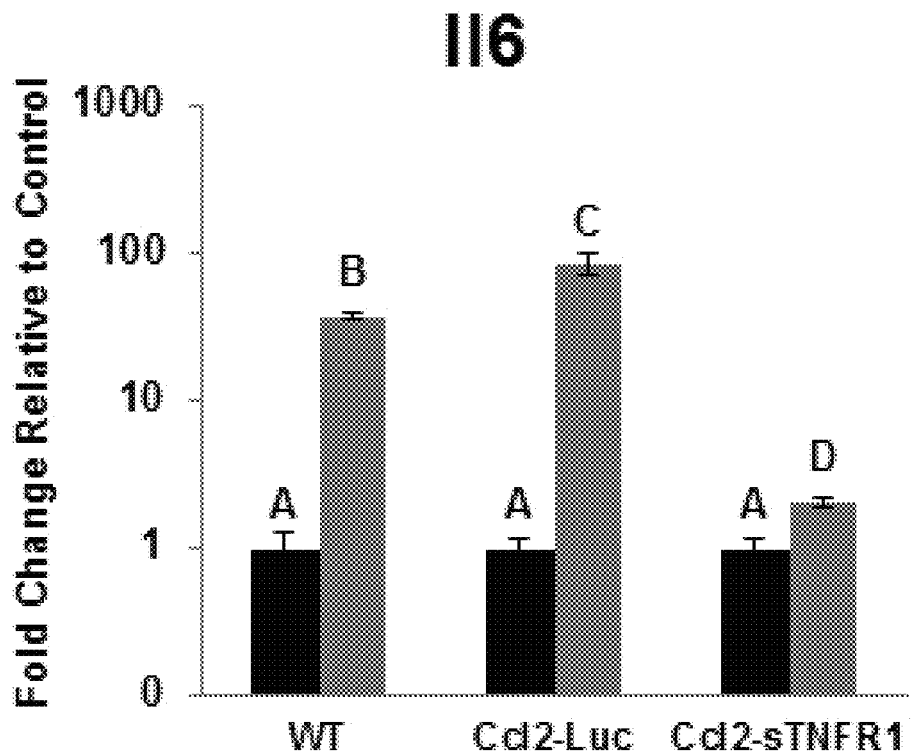
Figure 16C:
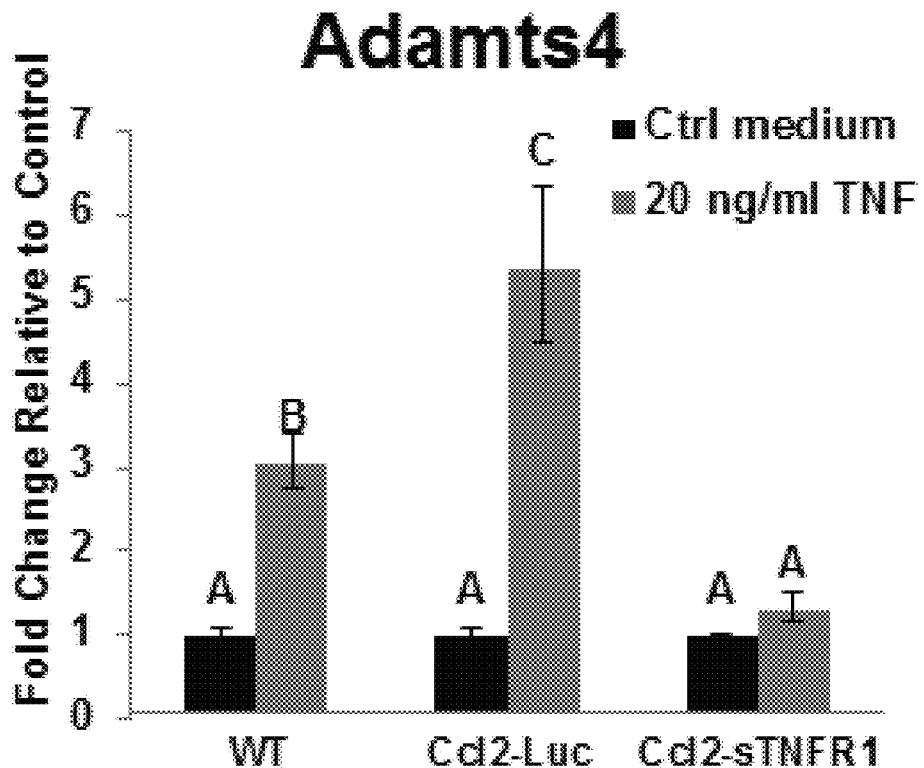
Figure 16D:
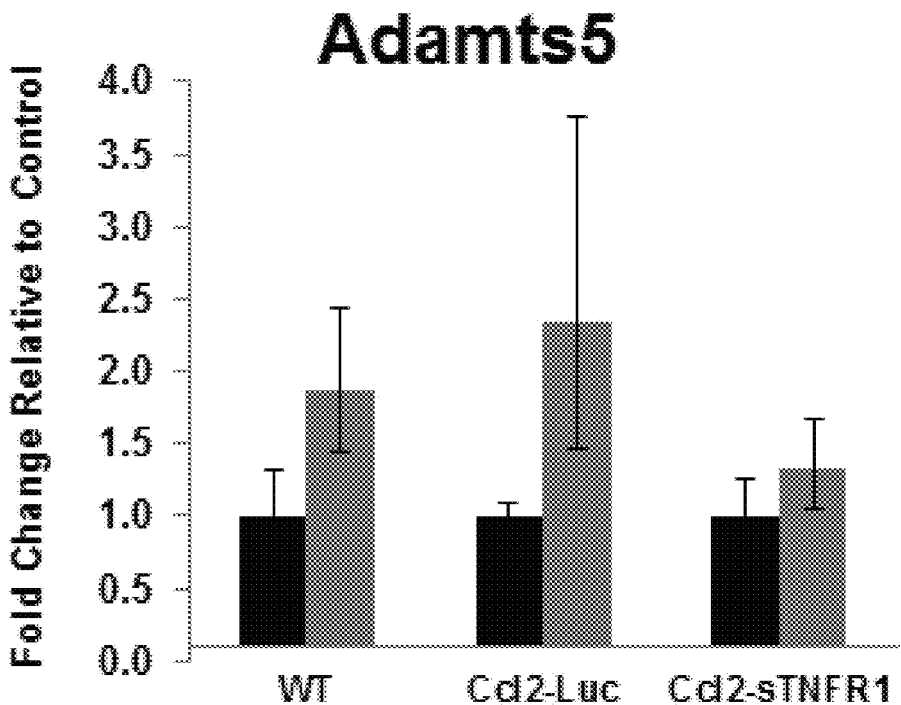
Figure 16E:
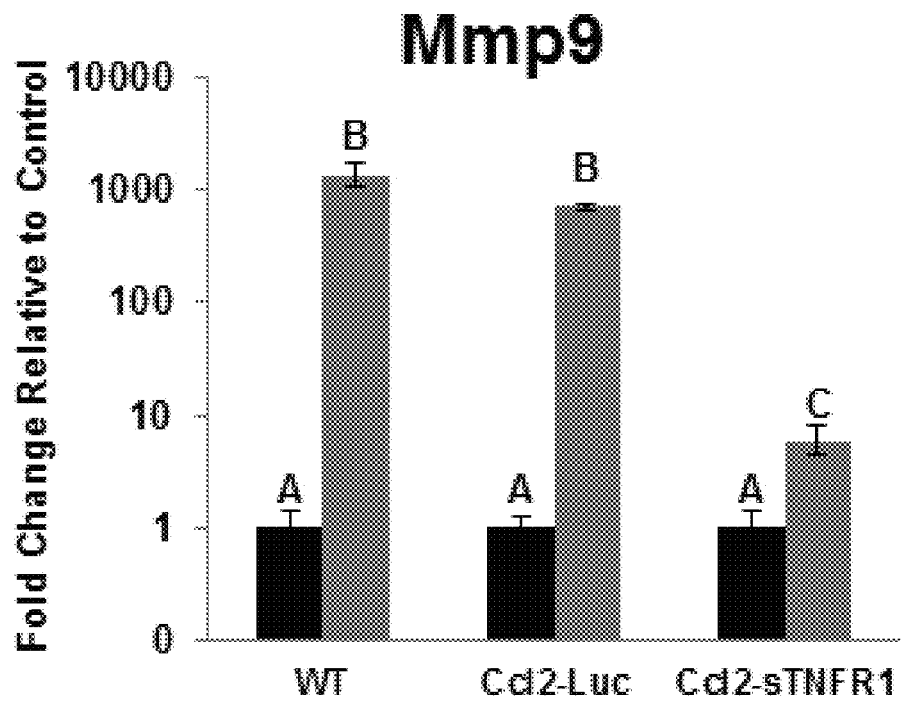
Figure 16F:
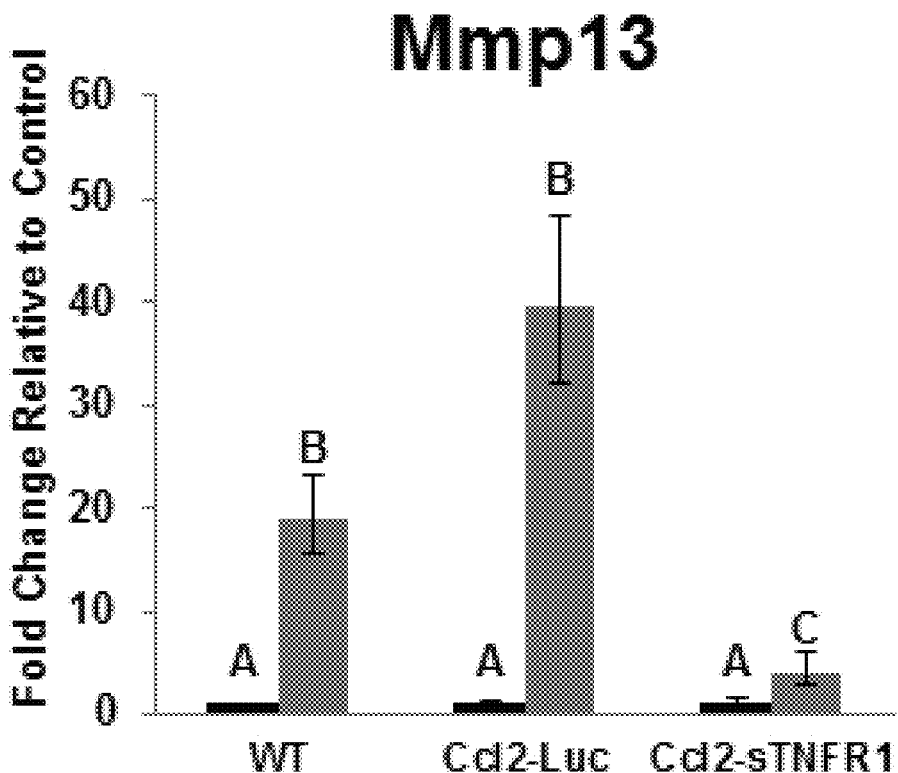
Figure 16G:
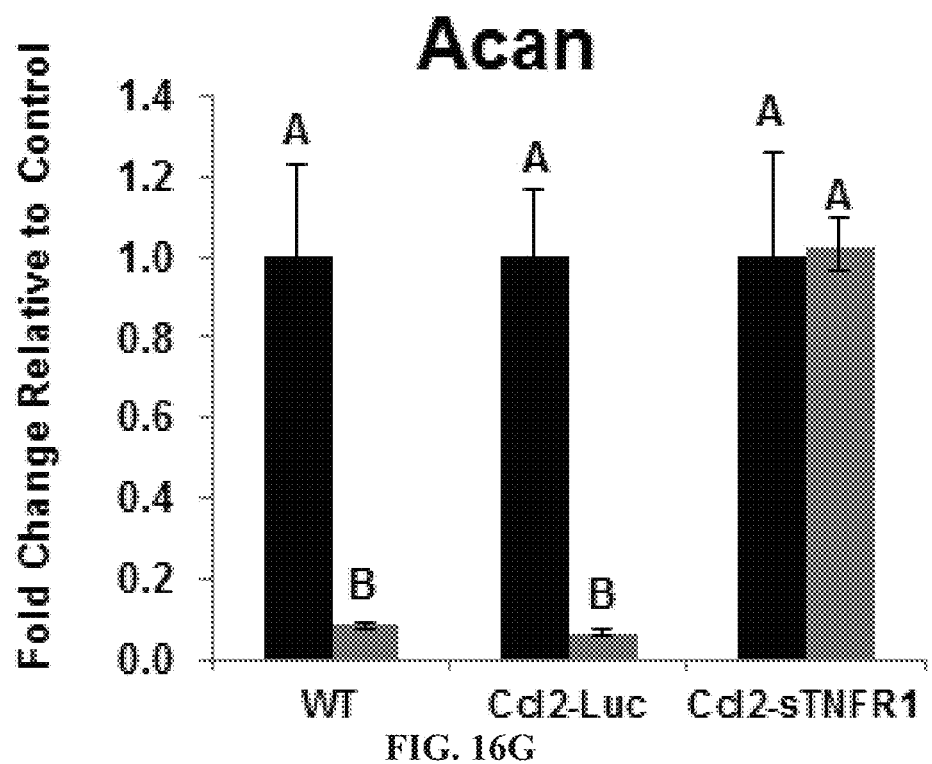
Figure 16H:
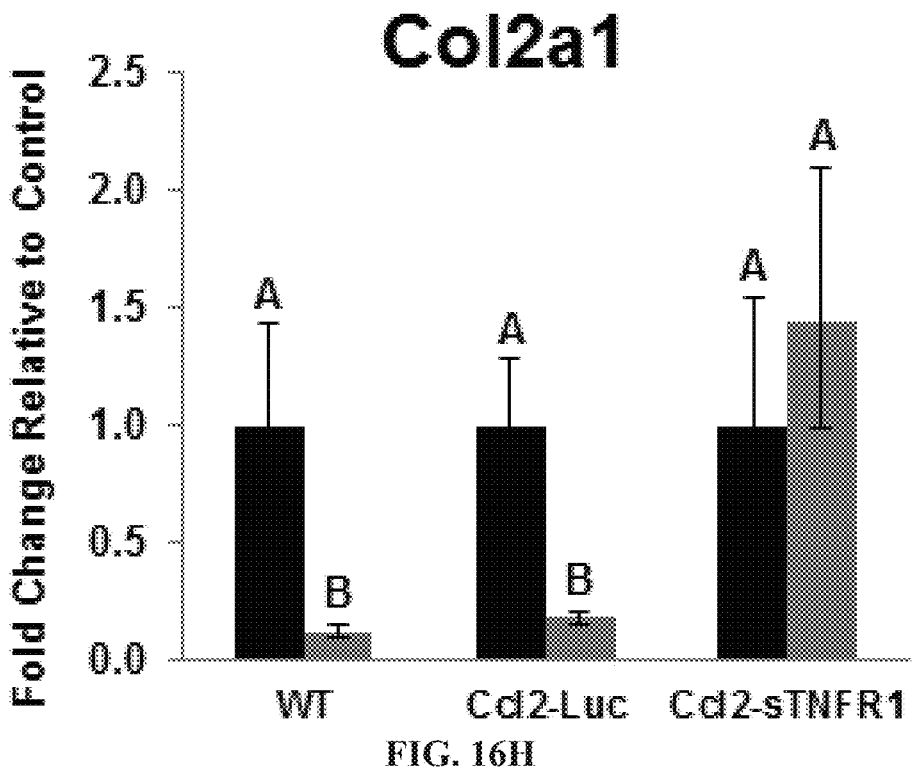

When treated with 0.1 ng/ml IL-1α, which sTNFR1 would not be expected to antagonize, there was approximately 300-fold stimulation of sTNFR1 production (FIG. 14B) to ~630 ng/ml. When treated with 20 ng/ml TNF-α, production of sTNFR1 increased only approximately 50-fold over basal levels to ~90 ng/ml. In a similar vein, treatment of Ccl2-Il1ra cells with IL-1α resulted in an increase of Il1ra protein in the medium of approximately 30-fold over basal levels of expression to ~180 ng/ml, whereas treatment with TNF-α resulted in an increase of approximately 88-fold to ~570 ng/ml (FIG. 14C). Thus, in the case of both Il1ra- and sTNFR1-expressing cells, either IL-1α or TNF-α are capable of potently inducing transgene expression. However, a lower fold induction is achieved when an effective, antagonizing therapy is produced in response to the stimulatory cytokine. The expression of transgenes may be auto-regulated in response to attenuation of the inducing signal. Cells can continue to respond to cytokines by producing additional therapy after previous exposure in a robust manner at the 24 hour timescale.

Example 7

Auto-Regulated Production of Cytokine Antagonists Protects Engineered Cartilage from IL-1- and TNF-Mediated Catabolism After establishing that the engineered cells indeed express transgenes in a cytokine-inducible manner and that Ccl2-driven sTNFR1 mounts a tunable and effective response against even a high dose of TNF-α in monolayer experiments, whether tissues engineered from the genome edited, designer stem cells could overcome the degenerative effects of TNF-α and IL-1α was investigated. Toward this end, pre-differentiated cells from WT, Ccl2-Luc, Ccl2-Il1ra, and Ccl2-sTNFR1 clones were further differentiated toward the chondrocyte lineage for the production of engineered cartilage tissue. Engineered tissues from WT and Ccl2-Luc cell lines were treated with 0 ng/ml cytokine, 0.1-1 ng/ml IL-1α or 20 ng/ml TNF-α. Engineered tissues from Ccl2-Il1ra and Ccl2-sTNFR1 cell lines were treated with only IL-1α or TNF-α, respectively, at the same concentrations as WT and Ccl2-Luc tissues.

The cartilage derived from WT and Luc cell lines was severely deteriorated in response to this 72 hour cytokine treatment after cartilage maturation. The changes in gene expression induced by 1 ng/ml IL-1α or 20 ng/ml TNF-α were measured by qRT-PCR (FIG. 15 and FIG. 16, respectively) and observed significant upregulation of a variety of markers of inflammation, such as Ccl2 and Il6, as well as degradative enzymes, such as matrix metalloproteinases and aggrecanases. Furthermore, significant suppression of collagen type 2α1 (Col2a1) and aggrecan (Acan), is noted in cartilage engineered from either WT or Ccl2-Luc cells. Biochemically cartilage derived from these control cell lines reflected a loss of sulfated glycosaminoglycan (sGAG), a major component of articular cartilage critical to proper tissue function, in response to both concentrations of IL-1α and to 20 ng/ml TNF-α (FIG. 17A, FIG. 17B, FIG. 17C, and FIG. 17D).

Figure 17A:
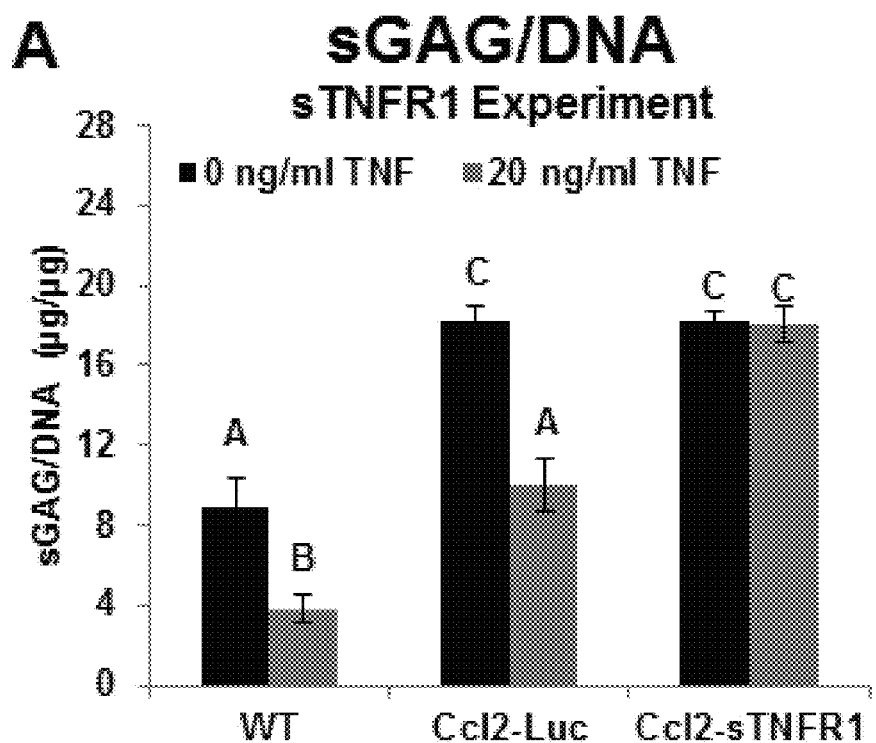
FIG. 17A shows sulfated glycosaminoglycan (sGAG) per double-stranded DNA as measured via the dimethylmethylene blue assay in cartilage aggregates engineered from WT, Ccl2-Luc, or Ccl2-sTNFR1 cells and maintained in control medium or medium supplemented with 20 ng/ml TNF-α for 3 days after maturation.
Figure 18:
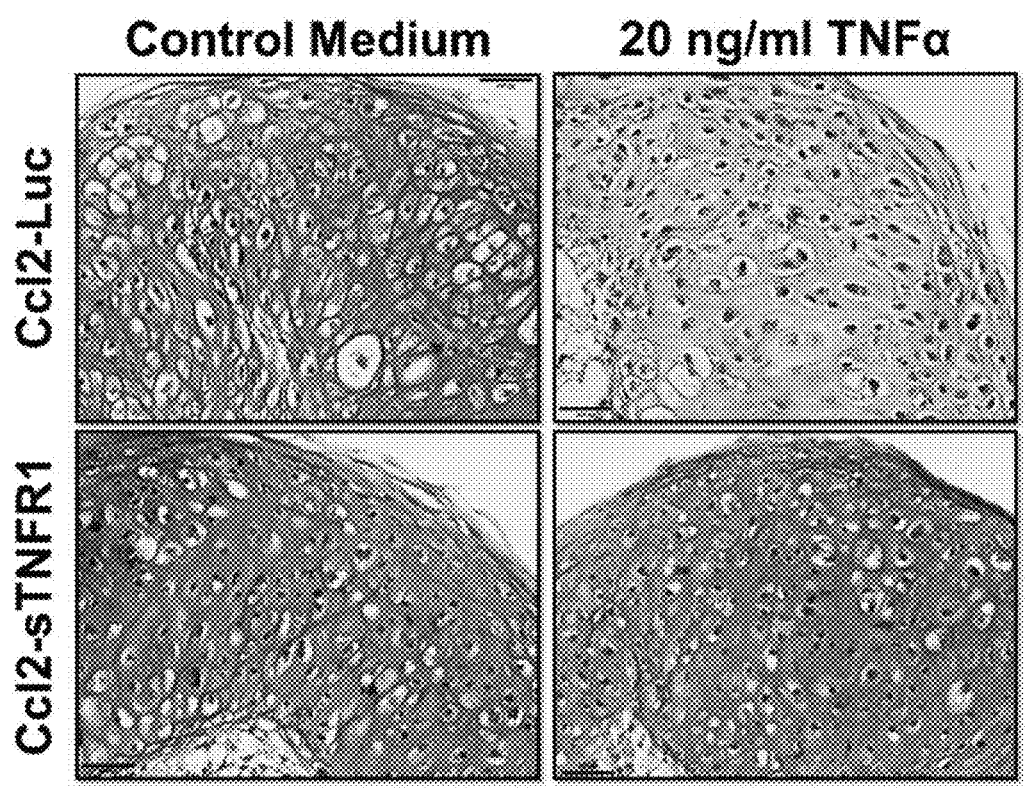
FIG. 18 shows photomicrographs from Safranin-O/Fast Green/Hematoxylin-stained tissue sections from engineered cartilage samples. Scale bar=50 μm.

Cartilage derived from Ccl2-Il1ra or Ccl2-sTNFR1 cells displayed a markedly different response to cytokine treatment at the gene expression level. Tissue generated from both the Ccl2-Il1ra and Ccl2-sTNFR1 cell lines demonstrated lower induction levels of inflammatory and degradative gene products as compared to cartilage engineered from WT or Ccl2-Luc cell lines (FIG. 15 and FIG. 16, respectively). In some cases, these genes were still significantly upregulated relative to tissues treated with 0 ng/ml cytokine. In the case of Ccl2-sTNFR1, cartilage aggregates displayed resilience after the 72 hours of treatment with TNF-α, with no suppression of collagen type 2α1 or aggrecan. The preservation of a more homeostatic gene expression profile was found to be consistent with the biochemical composition of cartilage aggregates engineered from the Ccl2-sTNFR1 cell line, which demonstrated preservation of sGAG in the tissue even after treatment with 20 ng/ml TNF-α, as reflected from biochemical and histologic data (FIG. 17A, FIG. 18). TNF-α was shown to have induced secretion of sTNFR1, as samples treated with 20 ng/ml TNF-α produced 18.45±0.17 ng/ml sTNFR1 and those cultured in the absence of TNF-α produced only 3.31±0.17 ng/ml sTNFR1.

Figure 17B:
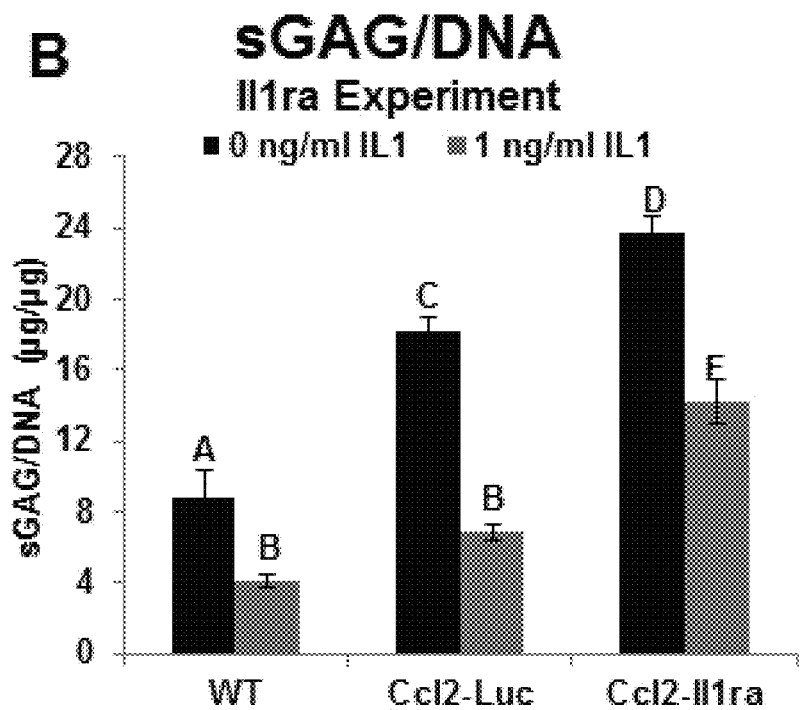
FIG. 17B shows sGAG/DNA in cartilage aggregates engineered from WT, Ccl2-Luc, or Ccl2-Il1ra cells and maintained in control medium or medium supplemented with 1 ng/ml IL-1α for 3 days after maturation.
Figure 17C:
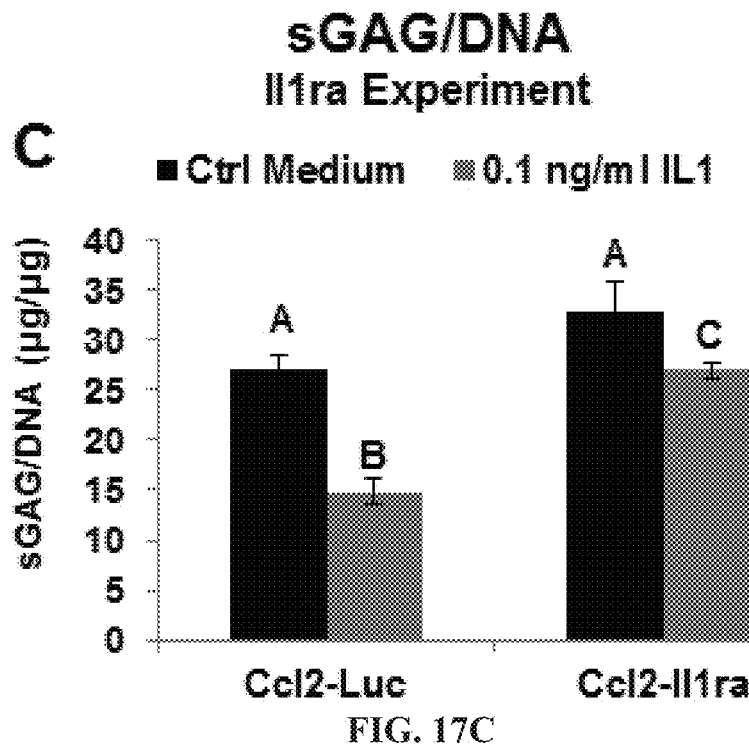
FIG. 17C shows sGAG/DNA in cartilage aggregates engineered from either Ccl2-Luc or Ccl2-Il1ra cells and maintained in control medium or medium supplemented with 0.1 ng/ml IL-1α for 3 days after maturation.
Figure 17D:
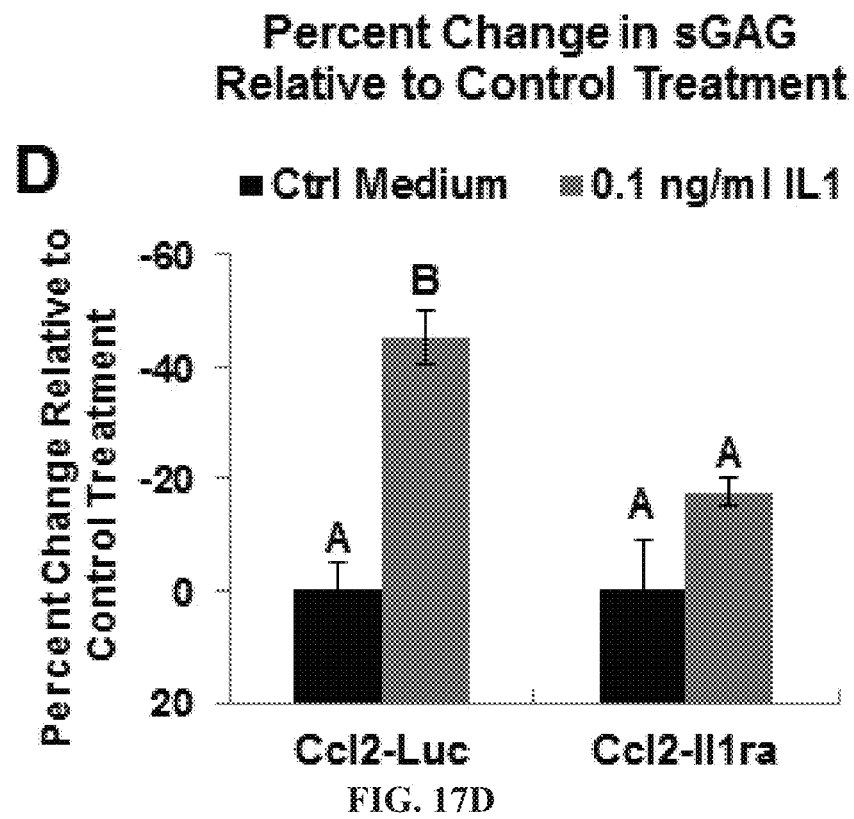
FIG. 17D shows Percent change in sGAG content upon treatment with 0.1 ng/ml IL-1α relative to 0 ng/ml IL-1α control samples. Bars represent the mean±SEM (n=3-6). Groups not sharing the same letter are statistically different (p<0.05).

However, Ccl2-driven expression of Il1ra was not sufficient to protect against the suppression of the extracellular matrix constituents Col2a1 and Acan by 1 ng/ml IL-1α, and this, coupled with the increased expression of degradative enzymes, resulted in loss of a significant fraction of sGAG in the engineered tissue (FIG. 17B, FIG. 17C, and FIG. 17D). At the 0.1 ng/ml IL-1α level, cartilage derived from engineered Ccl2-Il1ra cells were less susceptible to degradation than tissue derived from control Ccl2-Luc cells, though sGAG loss normalized to total DNA content was still statistically significant after cytokine treatment in both tissue types (FIG. 17). This protection was imparted by the cytokine induced expression of 20.50±0.67 ng/ml Il1ra, which was higher than the basal expression of 1.82±0.24 ng/ml observed in the engineered cells or 0.88±0.25 ng/ml observed in Ccl2-Luc cells. The effect of 0.1 ng/ml IL-1α on cartilage derived from WT cells was not tested.

Treatment with a range of TNF concentrations spanning three orders of magnitude resulted in differential induction of transgene transcription. The concomitant decay in transgene expression and transcription of markers of inflammation such as 11-6 suggests that cells were capable of autonomously tuning expression of the transgene. The AU-rich elements in the 3'-UTR were uncoupled by insertion of the transgene cassette, which included a drug-selectable marker as well as polyadenylation sequences. Expression of the transgenes did decay after resolution of cytokine stimulation, which came about by transgene therapy or simple withdrawal of cytokine. In some embodiments, reservation of the AU-rich elements in the transgene cassette may provide a means whereby even more rapid declines in transgene expression may be achieved.

Example 8

ADAMTS-5

Figure 2:
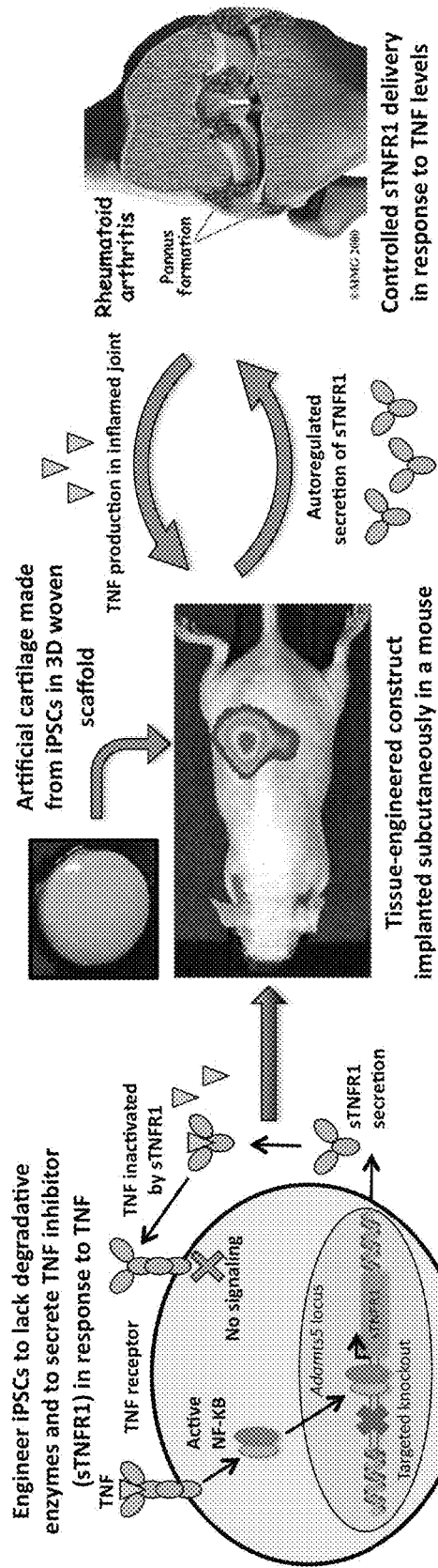
FIG. 2 shows an approach for the development of a "smart" drug delivery system for the treatment of arthritis. Induced pluripotent stem cells (iPSCs) are genetically modified to respond to the pro-inflammatory cytokine TNF-α by producing the soluble TNF receptor (sTNFR1), an inhibitor of TNF-α, instead of the degradative enzyme aggrecanase (ADAMTS-5). This tissue-engineered construct can be implanted subcutaneously, providing an autoregulated factory for anti-inflammatory drug delivery.

Customized iPSCs are generated where the chromosomal loci of catabolic genes that are activated by TNF via NF-κB are edited. In particular, functional deficiencies of the enzyme Adamts5 prevent cartilage degeneration in mouse models of osteoarthritis, and ADAMTS-5 inhibitors are a primary area of pharmaceutical research for arthritis therapies. Synthetic gene-editing nucleases are custom-designed to edit the chromosomal locus of Adamts5 by inducing a targeted double-strand break at a specific site within that locus. The chromosomal locus of Adamts5 is disrupted, and a synthetic expression cassette driving TNF-inducible transcription of sTNFR1 is inserted into the locus (see FIG. 2). The sTNFR1 expression cassette is integrated into the iPSC chromosomal DNA via either lentiviral transduction or targeted genome editing of the Adamts5 locus. Genome engineering with different gene targeting vectors provided as templates for homology-directed repair facilitate the integration of the synthetic expression cassette into the Adamts5 locus.

ADAMTS-5-deficient iPSCs are engineered to possess the NF-κB responsive transcriptional control system driving expression of either luciferase or sTNFR1 from the Adamts5 locus. iPSC clones are screened via genomic PCR and Southern Blot, and successful targeting is confirmed via sequencing of the edited locus. After stimulation with various concentrations and durations of TNF, luciferase reporter assays characterize the real-time responsiveness of the system. sTNFR1 gene and protein expression are measured via qRT-PCR and ELISA. To assess the ability of the cells to modulate inflammation, gene and protein levels of NF-κB targets, such as pro-inflammatory cytokines, MMPs, and ADAMTS family members, are analyzed in parallel. These methods are applied to human iPSCs or adult stem cells.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A composition for treating a subject having or suspected of having a disease, the composition comprising a modified cell comprising a modified endogenous gene, wherein an endogenous gene or fragment thereof is replaced with a transgene using a CRISPR/Cas9 system to generate the modified endogenous gene, the modified cell having an altered response to a cell signal or stimulus.

Clause 2. The composition of clause 1, wherein the altered response to the cell signal or stimulus comprises an activation of the transgene.

Clause 3. The composition of clause 1 or 2, wherein the transgene encodes a transcription factor or a therapeutic molecule.

Clause 4. The composition of clause 3, wherein the transgene encodes a transcription factor and the activation of the transcription factor activates or downregulates a signaling pathway in response to the cell signal or stimulus as compared to the response to the cell signal or stimulus by the unmodified endogenous gene.

Clause 5. The composition of clause 4, wherein the activation of the transcription factor activates an anti-inflammatory response and the unmodified endogenous gene activates an inflammatory response.

Clause 6. The composition of clause 5, wherein the coding region of the endogenous gene is replaced with the coding region of a transgene and the coding region of the transgene is operably linked to the promoter of the endogenous gene.

Clause 7. The composition of clause 6, wherein the modified cell comprises self-regulated feedback control of anti-cytokine therapy to a subject.

Clause 8. The composition of any one of clauses 1 to 7, wherein the endogenous gene is Ccl2 or ADAMTS-5.

Clause 9. The composition of any one of clauses 1 to 8, wherein the transgene is sTNFR1 or IL-1Ra.

Clause 10. The composition of clause 3, wherein the transgene encodes a therapeutic molecule.

Clause 11. The composition of clause 10, wherein the modified cell produces therapeutic molecules in response to the cell signal or stimulus.

Clause 12. The composition of any one of clauses 1 to 11, wherein the cell signal or stimulus comprises TNF-α and IL-1α.

Clause 13. A composition for treating a subject having or suspected of having a disease or disorder, the composition comprising a modified cell comprising a modified endogenous gene, wherein an endogenous gene or fragment thereof comprises a signal peptide and the signal peptide is deleted or knocked out using a CRISPR/Cas9 system to generate the modified endogenous gene, the modified cell having an altered response to a cell signal or stimulus.

Clause 14. The composition of clause 13, wherein the altered response to the cell signal or stimulus comprises a decrease in responsiveness of the modified endogenous gene to the cell signal or stimuli compared to an unmodified endogenous gene.

Clause 15. The composition of clause 13 or 14, wherein the modified cell is resistant to IL-1 induced inflammation Clause 16. The composition of any one of clauses 13 to 15, wherein the endogenous gene is IL1r1.

Clause 17. The composition of any one of clauses 13 to 16, wherein the cell signal or stimulus comprises IL-1.

Clause 18. The composition of any one of clauses 1 to 17, wherein the disease is a chronic disease.

Clause 19. The composition of clause 18, wherein the chronic disease is osteoarthritis.

Clause 20. The composition of any one of clauses 1 to 17, wherein the disease is cancer.

Clause 21. The composition of any one of clauses 1 to 20, wherein the modified cell is a modified induced pluripotent stem cell or a modified T-cell.

Clause 22. A method of preventing, treating or ameliorating a disease in a subject, the method comprising administering to the subject a therapeutically effective amount of the composition of any one of clauses 1 to 21 to the subject.

Clause 23. A method of generating a modified cell comprising a modified endogenous gene, the modified cell having an altered response to a cell signal or stimulus, the method comprising replacing an endogenous gene or fragment thereof with a transgene using a CRISPR/Cas9 system to generate the modified endogenous gene.

Clause 24. The method of clause 23, wherein the altered response to the cell signal or stimulus comprises an activation of the transgene.

Clause 25. The method of clause 23 or 24, wherein the transgene encodes a transcription factor or a therapeutic molecule.

Clause 26. The method of clause 25, wherein the transgene encodes a transcription factor and the activation of the transcription factor activates or downregulates a signaling pathway in response to the cell signal or stimulus as compared to the response to the cell signal or stimulus by the unmodified endogenous gene.

Clause 27. The method of clause 26, wherein the activation of the transcription factor activates an anti-inflammatory response and the unmodified endogenous gene activates an inflammatory response.

Clause 28. The method of clause 27, wherein the coding region of the endogenous gene is replaced with the coding region of a transgene and the coding region of the transgene is operably linked to the promoter of the endogenous gene.

Clause 29. The method of clause 28, wherein the modified cell comprises self-regulated feedback control of anti-cytokine therapy to a subject.

Clause 30. The method of any one of clauses 23 to 29, wherein the endogenous gene is Ccl2 or ADAMTS-5.

Clause 31. The method of any one of clauses 23 to 30, wherein the transgene is sTNFR1.

Clause 32. The method of clause 25, wherein the transgene encodes a therapeutic molecule.

Clause 33. The method of clause 32, wherein the modified cell produces therapeutic molecules in response to the cell signal or stimulus.

Clause 34. The method of any one of clauses 23 to 33, wherein the cell signal or stimulus comprises TNF-α and IL-1α.

Clause 35. A method of generating a modified cell comprising a modified endogenous gene comprising a signal peptide, the modified cell having an altered response to a cell signal or stimulus, the method comprising deleting or knocking out the signal peptide using a CRISPR/Cas9 system to generate the modified endogenous gene.

Clause 36. The method of clause 35, wherein the altered response to the cell signal or stimulus comprises a decrease in responsiveness of the modified endogenous gene to the cell signal or stimuli compared to an unmodified endogenous gene.

Clause 37. The method of clause 35 or 36, wherein the modified cell is resistant to IL-1 induced inflammation Clause 38. The method of any one of clauses 35 to 37, wherein the endogenous gene is IL1r1.

Clause 39. The composition of any one of clauses 35 to 38, wherein the cell signal or stimulus comprises IL-1.

Clause 40. The method of any one of clauses 23 to 39, wherein the disease is a chronic disease.

Clause 41. The method of clause 40, wherein the chronic disease is osteoarthritis Clause 42. The method of any one of clauses 23 to 39, wherein the disease is cancer.

Clause 43. The method of any one of clauses 23 to 42, wherein the modified cell is a modified induced pluripotent stem cell or a modified T-cell. .

What is claimed is:

1. A composition for treating a subject having or suspected of having an inflammatory disease, the composition comprising an isolated modified mammalian cell; the modified cell comprising a modified genome having a type I soluble tumor necrosis factor receptor antagonist (sTNFR1) transgene or an interleukin-1 receptor antagonist (IL-1 Ra) transgene under the transcriptional control of the endogenous C-C Motif Chemokine Ligand 2 (Ccl2) promoter or a disintegrin and metalloproteinase with thrombospondin motifs 5 (ADAMTS-5) promoter at the endogenous Ccl2 or ADAMTS-5 locus, wherein the endogenous gene encoding Ccl2 or ADAMTS-5 has been replaced by the sTNFR1 transgene or IL-1 Ra transgene and the coding region of the transgene is operably linked to the promoter of the endogenous Ccl2 or ADAMTS-5 gene, and wherein IL-1α or TNF-α stimulation drives transcriptional expression of the transgene.

2. The composition of claim 1, wherein the modified cell is an induced pluripotent stem cell or an adult stem cell.

3. The composition of claim 1, wherein expression of the sTNFR1 or a interleukin-1 receptor antagonist protects the subject from inflammation by reducing IL-1 or TNF signaling levels.

4. The composition of claim 1, wherein the modified cell is a modified T-cell.

* * * * *

SEQUENCE LISTING

<160> NUMBER OF SEQ ID NOS: 47

<210> SEQ ID NO 1
<211> LENGTH: 20
<212> TYPE: DNA
<213> ORGANISM: Artificial sequence
<220> FEATURE:
<223> OTHER INFORMATION: Synthetic

<400> SEQUENCE: 1
gcttctgtgt tgaagactca                                                    20

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
gtagctgtgg gcccacaacc                                                    20

<210> SEQ ID NO 3
<211> LENGTH: 25
<212> TYPE: DNA
<213> ORGANISM: Artificial sequence
<220> FEATURE:
<223> OTHER INFORMATION: Synthetic

<400> SEQUENCE: 3
tcatctcctg gttagttatg gtatc                                              25

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
ccgaggccaa tgagattaag                                                    20

<210> SEQ ID NO 5
<211> LENGTH: 52
<212> TYPE: DNA
<213> ORGANISM: Artificial sequence
<220> FEATURE:
<223> OTHER INFORMATION: Synthetic

<400> SEQUENCE: 5
ggaaattccc ggaaagtccc cggaaattcc cggaaagtcc ccggaaattc cc                52

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
cggctaccac atccaaggaa                                                    20

<210> SEQ ID NO 7
<211> LENGTH: 20
<212> TYPE: DNA
<213> ORGANISM: Artificial sequence

```
<220> FEATURE:
<223> OTHER INFORMATION: Synthetic

<400> SEQUENCE: 7
gcatgagaga ggcgaatgga                                                   20

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
gaccttccgt gaagagcagt gt                                                22

<210> SEQ ID NO 9
<211> LENGTH: 22
<212> TYPE: DNA
<213> ORGANISM: Artificial sequence
<220> FEATURE:
<223> OTHER INFORMATION: Synthetic

<400> SEQUENCE: 9
gcccacccaa tggtaaatct tt                                                22

<210> SEQ ID NO 10
<211> LENGTH: 21
<212> TYPE: DNA
<213> ORGANISM: Artificial sequence
<220> FEATURE:
<223> OTHER INFORMATION: Synthetic

<400> SEQUENCE: 10
ggctcagcca gatgcagtta a                                                 21

<210> SEQ ID NO 11
<211> LENGTH: 23
<212> TYPE: DNA
<213> ORGANISM: Artificial sequence
<220> FEATURE:
<223> OTHER INFORMATION: Synthetic

<400> SEQUENCE: 11
tccagatgac tttcctccgt cta                                               23

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
ggccctcatg gctgccacct                                                   20

<210> SEQ ID NO 13
<211> LENGTH: 23
<212> TYPE: DNA
<213> ORGANISM: Artificial sequence
<220> FEATURE:
<223> OTHER INFORMATION: Synthetic

<400> SEQUENCE: 13
gaggatacca ctcccaacag acc                                               23
```

```
<210> SEQ ID NO 14
<211> LENGTH: 24
<212> TYPE: DNA
<213> ORGANISM: Artificial sequence
<220> FEATURE:
<223> OTHER INFORMATION: Synthetic

<400> SEQUENCE: 14
cgaacttcga cactgacaag aagt                                              24

<210> SEQ ID NO 15
<211> LENGTH: 24
<212> TYPE: DNA
<213> ORGANISM: Artificial sequence
<220> FEATURE:
<223> OTHER INFORMATION: Synthetic

<400> SEQUENCE: 15
gggctctgaa tggttatgac attc                                              24

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
gggcctcgaa agagtcctgt                                                   20

<210> SEQ ID NO 17
<211> LENGTH: 25
<212> TYPE: DNA
<213> ORGANISM: Artificial sequence
<220> FEATURE:
<223> OTHER INFORMATION: Synthetic

<400> SEQUENCE: 17
ctgatctcgt agcgatcttt cttct                                             25

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
cctggcaggt gagtttgcat                                                   20

<210> SEQ ID NO 19
<211> LENGTH: 23
<212> TYPE: DNA
<213> ORGANISM: Artificial sequence
<220> FEATURE:
<223> OTHER INFORMATION: Synthetic

<400> SEQUENCE: 19
tgactccttt tgcatcagac tga                                               23

<210> SEQ ID NO 20
<211> LENGTH: 24
<212> TYPE: DNA
<213> ORGANISM: Artificial sequence
<220> FEATURE:
<223> OTHER INFORMATION: Synthetic
```

```
<400> SEQUENCE: 20
cctactcatt gggatcatct tgct                                              24

<210> SEQ ID NO 21
<211> LENGTH: 23
<212> TYPE: DNA
<213> ORGANISM: Artificial sequence
<220> FEATURE:
<223> OTHER INFORMATION: Synthetic

<400> SEQUENCE: 21
aggtaggcga tgctgttctt aca                                               23

<210> SEQ ID NO 22
<211> LENGTH: 25
<212> TYPE: DNA
<213> ORGANISM: Artificial sequence
<220> FEATURE:
<223> OTHER INFORMATION: Synthetic

<400> SEQUENCE: 22
ttgggatctt gtctgaggtc ctgga                                             25

<210> SEQ ID NO 23
<211> LENGTH: 24
<212> TYPE: DNA
<213> ORGANISM: Artificial sequence
<220> FEATURE:
<223> OTHER INFORMATION: Synthetic

<400> SEQUENCE: 23
aagtgcatca tcgttgttca taca                                              24

<210> SEQ ID NO 24
<211> LENGTH: 21
<212> TYPE: DNA
<213> ORGANISM: Artificial sequence
<220> FEATURE:
<223> OTHER INFORMATION: Synthetic

<400> SEQUENCE: 24
gcacgctgga atgatctaag c                                                 21

<210> SEQ ID NO 25
<211> LENGTH: 23
<212> TYPE: DNA
<213> ORGANISM: Artificial sequence
<220> FEATURE:
<223> OTHER INFORMATION: Synthetic

<400> SEQUENCE: 25
agcgctcagt ctcttcacct ctt                                               23

<210> SEQ ID NO 26
<211> LENGTH: 25
<212> TYPE: DNA
<213> ORGANISM: Artificial sequence
<220> FEATURE:
<223> OTHER INFORMATION: Synthetic

<400> SEQUENCE: 26
caccgctctt cctccaccac catgc                                             25

<210> SEQ ID NO 27
```

```
<211> LENGTH: 25
<212> TYPE: DNA
<213> ORGANISM: Artificial sequence
<220> FEATURE:
<223> OTHER INFORMATION: Synthetic

<400> SEQUENCE: 27
aaacgcatgg tggtggagga agagc                                          25

<210> SEQ ID NO 28
<211> LENGTH: 25
<212> TYPE: DNA
<213> ORGANISM: Artificial sequence
<220> FEATURE:
<223> OTHER INFORMATION: Synthetic

<400> SEQUENCE: 28
aaacgcatgg tggtggagga agagc                                          25

<210> SEQ ID NO 29
<211> LENGTH: 24
<212> TYPE: DNA
<213> ORGANISM: Artificial sequence
<220> FEATURE:
<223> OTHER INFORMATION: Synthetic

<400> SEQUENCE: 29
catggtggtg gaggaagaga gagc                                           24

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
caggtccctg tcatgcttct g                                              21

<210> SEQ ID NO 31
<211> LENGTH: 22
<212> TYPE: DNA
<213> ORGANISM: Artificial sequence
<220> FEATURE:
<223> OTHER INFORMATION: Synthetic

<400> SEQUENCE: 31
atctgggatg tgatctttga ca                                             22

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
tcccaggagt ggctagaaaa                                                20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
```

```
ccacgacaat tcaaaaatgg                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
tcagctgcct gatctgagaa                                              20

<210> SEQ ID NO 35
<211> LENGTH: 22
<212> TYPE: DNA
<213> ORGANISM: Artificial sequence
<220> FEATURE:
<223> OTHER INFORMATION: Synthetic

<400> SEQUENCE: 35
aggtcaatag gcaccatgtc ta                                           22

<210> SEQ ID NO 36
<211> LENGTH: 21
<212> TYPE: DNA
<213> ORGANISM: Artificial sequence
<220> FEATURE:
<223> OTHER INFORMATION: Synthetic

<400> SEQUENCE: 36
cagcgtaagt gatgtccacc t                                            21

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
cactccctgc agtccgtatc                                              20

<210> SEQ ID NO 38
<211> LENGTH: 86
<212> TYPE: DNA
<213> ORGANISM: Artificial sequence
<220> FEATURE:
<223> OTHER INFORMATION: Synthetic

<400> SEQUENCE: 38
cgggaaattc cgctagcact agtgggactt tcccactagt gggaaattag cccgggactt   60
tcccgtctcc tcgagggggac ttccca                                      86

<210> SEQ ID NO 39
<211> LENGTH: 11
<212> TYPE: DNA
<213> ORGANISM: Artificial sequence
<220> FEATURE:
<223> OTHER INFORMATION: Synthetic

<400> SEQUENCE: 39
aattcctctg a                                                       11

<210> SEQ ID NO 40
```

```
<211> LENGTH: 20
<212> TYPE: DNA
<213> ORGANISM: Artificial sequence
<220> FEATURE:
<223> OTHER INFORMATION: Synthetic

<400> SEQUENCE: 40
gtccaggatg gttcctctgc                                                   20

<210> SEQ ID NO 41
<211> LENGTH: 20
<212> TYPE: DNA
<213> ORGANISM: Artificial sequence
<220> FEATURE:
<223> OTHER INFORMATION: Synthetic

<400> SEQUENCE: 41
attggactgg tccctcacct                                                   20

<210> SEQ ID NO 42
<211> LENGTH: 21
<212> TYPE: DNA
<213> ORGANISM: Artificial sequence
<220> FEATURE:
<223> OTHER INFORMATION: Synthetic

<400> SEQUENCE: 42
gctcttcctc caccaccatg c                                                 21

<210> SEQ ID NO 43
<211> LENGTH: 20
<212> TYPE: DNA
<213> ORGANISM: Artificial sequence
<220> FEATURE:
<223> OTHER INFORMATION: Synthetic

<400> SEQUENCE: 43
gcttctgtgt tgaagactca                                                   20

<210> SEQ ID NO 44
<211> LENGTH: 20
<212> TYPE: DNA
<213> ORGANISM: Artificial sequence
<220> FEATURE:
<223> OTHER INFORMATION: Synthetic

<400> SEQUENCE: 44
gtagctgtgg gcccacaacc                                                   20

<210> SEQ ID NO 45
<211> LENGTH: 20
<212> TYPE: DNA
<213> ORGANISM: Artificial sequence
<220> FEATURE:
<223> OTHER INFORMATION: Synthetic

<400> SEQUENCE: 45
gcttctgtgt tgaagactca                                                   20

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
```

```
gtagctgtgg gcccacaacc                                              20
```

<210> SEQ ID NO 47
<211> LENGTH: 21
<212> TYPE: DNA
<213> ORGANISM: Artificial sequence
<220> FEATURE:
<223> OTHER INFORMATION: Synthetic

<400> SEQUENCE: 47

```
gctcttcctc caccaccatg c                                            21
```